United States Patent
Nakayama

(10) Patent No.: US 9,964,518 B2
(45) Date of Patent: May 8, 2018

(54) ELECTROPLATING SOLUTION ANALYZING APPARATUS

(71) Applicant: HIOKI DENKI KABUSHIKI KAISHA, Nagano (JP)

(72) Inventor: Naoto Nakayama, Nagano (JP)

(73) Assignee: HIOKI DENKI KABUSHIKI KAISHA, Nagano (JP)

(*) Notice: Subject to any disclaimer, the term of this patent is extended or adjusted under 35 U.S.C. 154(b) by 281 days.

(21) Appl. No.: 14/939,240

(22) Filed: Nov. 12, 2015

(65) Prior Publication Data

US 2016/0146757 A1 May 26, 2016

(30) Foreign Application Priority Data

Nov. 21, 2014 (JP) ................................. 2014-236183
Nov. 21, 2014 (JP) ................................. 2014-236185
Aug. 20, 2015 (JP) ................................. 2015-162997
Aug. 20, 2015 (JP) ................................. 2015-163000

(51) Int. Cl.
  *G01N 27/42* (2006.01)
  *G01N 27/48* (2006.01)
  *C25D 21/12* (2006.01)

(52) U.S. Cl.
  CPC .............. *G01N 27/48* (2013.01); *G01N 27/42* (2013.01); *C25D 21/12* (2013.01)

(58) Field of Classification Search
  CPC .......... G01N 27/42; G01N 27/48; G01N 33/20
  See application file for complete search history.

(56) References Cited

FOREIGN PATENT DOCUMENTS

JP          10-98268          4/1998

*Primary Examiner* — Alexander S Noguerola
(74) *Attorney, Agent, or Firm* — Greenblum & Bernstein, P.L.C.

(57) ABSTRACT

An electroplating solution analyzing apparatus measures a first current that flows between a counter electrode and a working electrode placed in electroplating solution while depositing metal on the working electrode by applying a set first voltage between a reference electrode and the working electrode and then measures a second current that flows between the counter electrode and the working electrode with a cycle set in advance while dissolving the metal deposited on the working electrode into the electroplating solution by applying a second voltage, which changes at a rate set in advance, between the reference electrode and the working electrode. During measurement, the first voltage is changed in a range set to produce a current density within a current density range set in advance. An analysis process then analyzes the state of the electroplating solution based on the values acquired by measurement.

8 Claims, 6 Drawing Sheets

F I G. 4
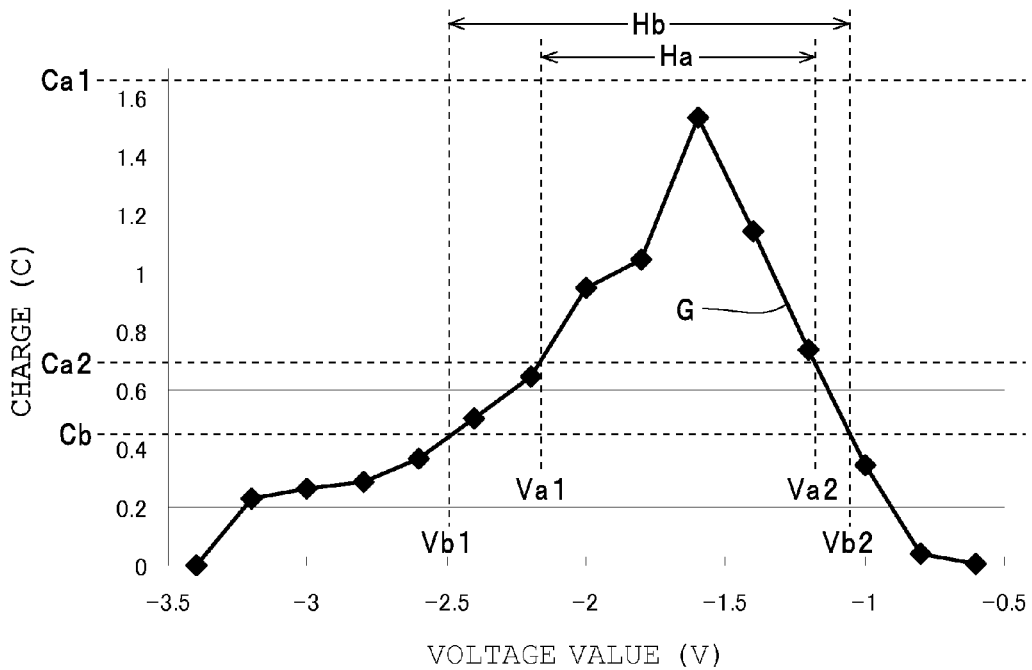
F I G. 5
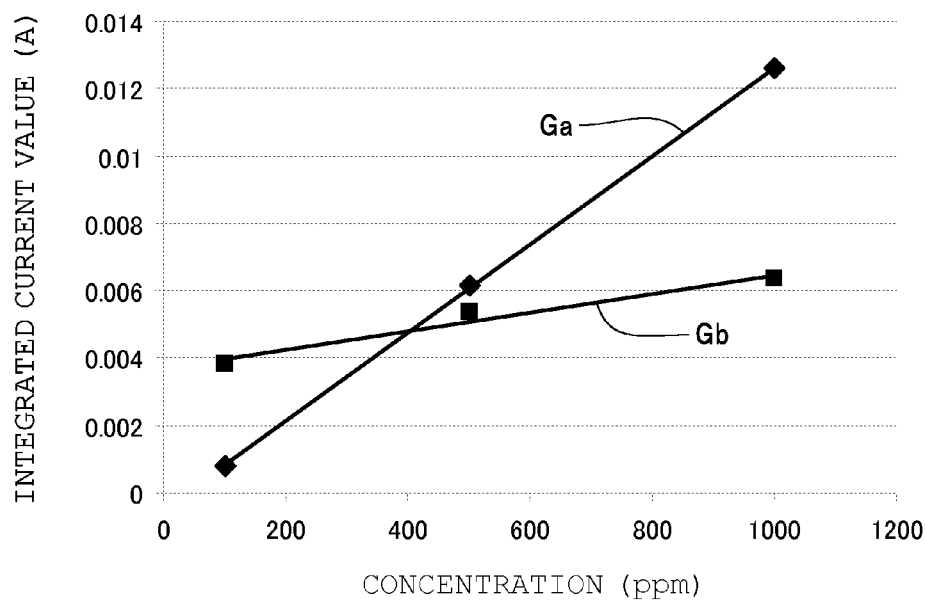

F I G. 1 0
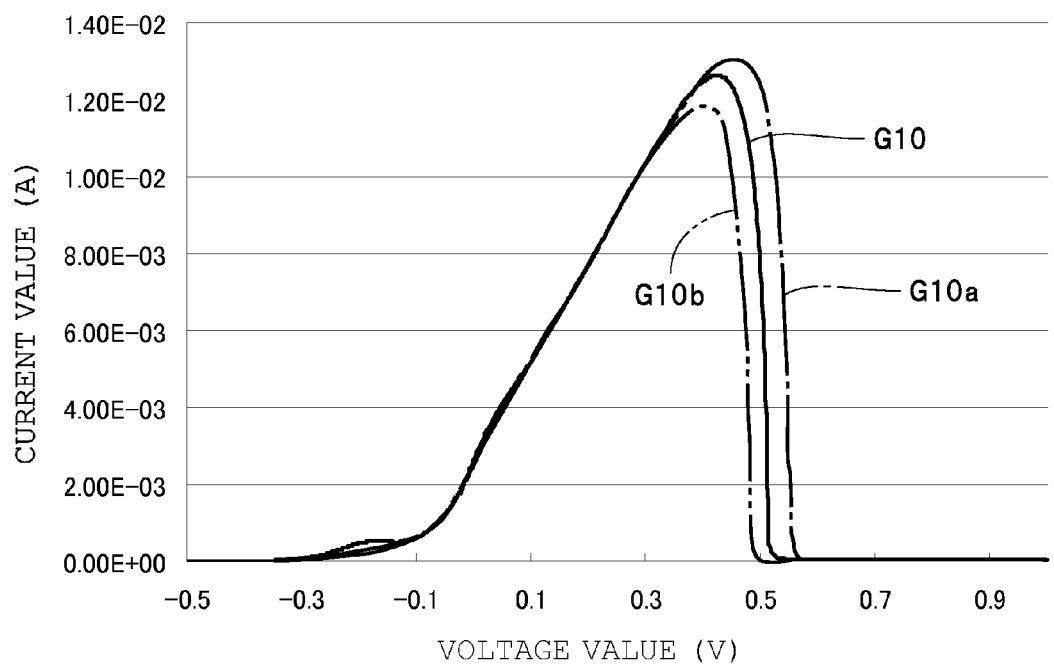

ELECTROPLATING SOLUTION ANALYZING APPARATUS

1. FIELD OF THE INVENTION

The present invention relates to an electroplating solution analyzing apparatus that analyzes the state of electroplating solution.

2. DESCRIPTION OF THE RELATED ART

When manufacturing a multilayer printed circuit board or the like, a method that performs an electroplating process to form column-shaped conductors (through-holes, vias, or the like) to connect the circuit layers (conductive patterns) to each other is widely used.

As one example, the patent document indicated below discloses a method of manufacturing a printed circuit board that forms column-shaped conductors by an electroplating process which uses a copper sulfate plating solution as a plating bath (electroplating solution). In this method of manufacturing, first a current film to be used as a feeder film is formed by an electroless copper plating process on lower-layer wiring that has been formed in advance on the circuit board. Next, after a resist has been applied and then dried, a plating resist pattern for forming column-shaped conductors on the circuit board is formed by exposing to ultraviolet light using a mask for forming the column-shaped conductors and then developing. After this, an electrolytic copper plating process is carried out using the circuit board (current film) as a negative electrode. When doing so, column-shaped conductors are formed by the copper deposited inside the openings in the plating resist pattern (i.e., on the current film at positions where the column-shaped conductors are to be formed). Next, after the plating resist pattern has been separated and any unnecessary current film has been removed, an insulating material is applied and dried to form a resin layer as an inter-layer insulating layer. By repeatedly carrying out the above process for the number of iterations that are required for the multilayer structure, a multilayer printed circuit board is completed.

SUMMARY OF THE INVENTION

However, the method of manufacturing a multilayer printed circuit board described above has the following problem to be solved. That is, with the conventional method of manufacturing, the conductor layers (conductor patterns) are connected to one another by forming column-shaped conductors using an electroplating process (copper electroplating process) that uses a copper sulfate plating solution as the plating bath (electroplating solution).

Here, to deposit a sufficient amount of metal on a base using an electroplating process, it is necessary to adjust the voltage value of the voltage applied between the base (cathode) and the electrode (anode) and the period for which the voltage is applied so as to produce a favorable current density at the base. Also, as the electroplating solution for forming column-shaped conductors or the like by an electroplating process, a variety of types of product are provided by various manufacturers, and the amount of metal deposited per unit time when applying a voltage so as to produce the same current density will differ between products. In addition, even with the same product (electroplating solution), depending on the usage time (the time for which a plating process has been carried out) and the usage environment (such as whether impurities have been mixed in), the amount of metal deposited per unit time when a voltage is applied so as to produce the same current density will change.

Accordingly, when forming column-shaped conductors or the like by an electroplating process, it is necessary to analyze the state of the electroplating solution actually used in a process that manufactures products and to decide, based on the analysis results, the voltage value and the like of the voltage to be applied between the product (cathode) and the anode when forming the column-shaped conductors. More specifically, as one example, a process that immerses a sample in the electroplating solution to be analyzed and carries out the electroplating process before taking the sample out of the electroplating solution, washing and drying the sample, and measuring the amount (i.e., thickness or the like) of the metal deposited on the sample by the electroplating process is executed a plurality of times while changing the voltage value of the voltage applied between the sample and the anode in the electroplating process. By doing so, analysis is performed into the state of the electroplating solution to be analyzed, i.e., what amount of metal can be deposited by what voltage value of the voltage applied between the sample and the anode.

In this case, the area that contacts the electroplating solution will differ between the samples used during analysis and the positions (in the above example, the current film inside the openings in the plating resist pattern) where a metal film is to be formed when manufacturing products. For this reason, the amount of metal deposited per unit time when a voltage with the same voltage value is applied will differ between an electroplating process that uses a sample and an electroplating process during the manufacturing of products. Accordingly, when specifying favorable manufacturing conditions (such as the voltage value of the voltage to be applied), the current density during an electroplating process that was capable of depositing the required amount of metal per unit time during analysis that uses samples is calculated, and the voltage value of the voltage to be applied to the product (cathode) and anode during the electroplating process and the like are determined based on the calculated current density and the area of the product on which metal is to be deposited.

In this way, with the conventional method of manufacturing, to decide the voltage value of the voltage applied between the printed circuit board (current film: cathode) and the anode during an electroplating process for forming column-shaped conductors, it is necessary to execute an electroplating process that uses a sample, washing and drying of the sample, and measurement of the amount of metal deposited on the sample a plurality of times while changing the voltage value of the voltage applied during the electroplating process. This means that there is a problem in that such analysis operations are extremely complicated.

In addition, during the electroplating process, the amount of metal included in the electroplating solution falls as the number of processes (the total usage time of the electroplating solution) increases. Also, even if an electroplating solution to be used during this type of electroplating process is in a state where the same number of electroplating processes have been carried out on the same processed objects, due to differences such as the presence or absence of mixed-in impurities and differences in the evaporated amount of electrolyte, the amount of metal deposited per unit time when a voltage with a predetermined voltage value is applied to the plated object (cathode) and the anode will differ.

For this reason, when repeatedly forming column-shaped conductors or the like a plurality of times using an electroplating process as in the conventional method of manufacturing, it is necessary to regularly analyze the state of the electroplating solution in use and, based on the analysis result, necessary to change the processing conditions such as the voltage value of the voltage to be applied between the product (cathode) and the anode (i.e., the current density at the cathode) and/or to replace with new electroplating solution before a state where it is difficult to deposit a sufficient amount of metal is reached. Accordingly, at a processing site where column-shaped conductors or the like are formed by an electroplating process, as one example, every time the electroplating process has been carried out a number of times set in advance, the state of the electroplating solution held in the plating solution tank is analyzed and the processing conditions are changed, the electroplating solution is replaced, or the like.

More specifically, as one example, after a sample has been immersed in the electroplating solution to be analyzed and the actual electroplating process has been carried out, the sample is taken out of the electroplating solution and washed and dried, and the state of the electroplating solution to be analyzed is grasped by measuring the amount of metal (the thickness or the like) deposited on the sample by the electroplating process and/or observing the state of the deposited metal. By doing so, the state of the electroplating solution to be analyzed, i.e., how and what amount of metal can be deposited, is analyzed and it is possible as necessary to change the processing conditions (of the electroplating process on the plated object) when manufacturing products and/or to replace with the new electroplating solution. However, it is extremely complicated to carry out an analysis process like that described above every time the electroplating process has been carried out a set number of times.

Also, since it is difficult to reuse samples (i.e., samples on which metal has been deposited) used to analyze electroplating solution, there is also the problem of an increase in the cost of analyzing the electroplating solution.

The present invention was conceived in view of the problems described above and has a principal object of providing an electroplating solution analyzing apparatus capable of analyzing the state of an electroplating solution to be analyzed easily and at low cost.

To achieve the stated object, the electroplating solution analyzing apparatus according to the present invention comprises a measuring unit capable of executing a measurement process that measures a current value of a current flowing between a counter electrode and a working electrode that have been placed in contact with an electroplating solution to be analyzed while applying a voltage to a reference electrode and the working electrode that have been placed in contact with an electroplating solution; and a processing unit that executes a measurement value acquiring process which controls the measuring unit to execute the measurement process and acquires measurement values and an analysis process that analyzes a state of the electroplating solution based on the acquired measurement values, wherein the processing unit executes, as the measurement value acquiring process, a deposition-dissolution process that executes: a process 1A that measures a current value of a first current that flows between the counter electrode and the working electrode as the measurement values while depositing metal on the working electrode by applying a first voltage with a voltage value set in advance between the reference electrode and the working electrode for a first period set in advance; and a process 2A that measures, as the measurement values, a current value of a second current that flows between the counter electrode and the working electrode with a cycle set in advance while dissolving the metal that was deposited on the working electrode in the process 1A into the electroplating solution by applying a second voltage whose voltage value changes with a rate of change set in advance between the reference electrode and the working electrode for a second period set in advance, in that order a plurality of times while changing the voltage value of the first voltage in a voltage value range set so as to produce a current density within a current density range set in advance, and the processing unit analyzes, in the analysis process, the state of the electroplating solution based on the measurement values acquired by the measurement value acquiring process.

According to the electroplating solution analyzing apparatus according to the present invention, unlike a convention analysis method that analyzes the state of electroplating solution by executing a deposition process a plurality of times with different voltage values of the voltage applied between the sample and the electrode and measures the deposited state of metal on each sample, it is possible, in the same way as when fabricating a plurality of samples while changing the voltage value of the voltage applied when depositing metal, to acquire measurement values in keeping with the deposited state of metal in each deposition process and analyze the state of the electroplating solution. When doing so, by dissolving the metal deposited on the working electrode during the process 1A in the electroplating solution during the process 2A of each deposition-dissolution process, it is possible to produce a state where metal is not deposited on the working electrode by the time the next deposition-dissolution process starts, which means that it is possible to continuously execute the deposition-dissolution process a plurality of times without replacing the working electrode numerous times and/or removing metal deposited on the working electrode. By doing so, it is possible, compared to the conventional analysis method where it is necessary to provide a plurality of samples and to execute the deposition process and the measurement process a plurality of times, to analyze the state of the electroplating solution easily and at low cost.

Also, the electroplating solution analyzing apparatus according to the present invention, as the analysis process, the processing unit executes at least one of: a process Aa that calculates, for each deposition-dissolution process, a second charge applied to the electroplating solution during the process 2A based on the current value of the second current and a second period for which the second current flowed between the counter electrode and the working electrode in the process 2A, calculates, for each deposition-dissolution process, a first current density based on the electrode area of the working electrode and the current value of the first current, and concludes from analysis, based on the calculated second charge and first current density, that the electroplating solution is in a state where the amount of metal deposited on the plated object per unit time increases as a plating process is carried out under conditions that produce the first current density in a deposition-dissolution process for which the second charge is large and where the amount of metal deposited on the plated object per unit time decreases as the plating process is carried out under conditions that produce the first current density in a deposition-dissolution process for which the second charge is small; a process Ba that calculates, for each deposition-dissolution process, a first charge applied to the electroplating solution during the process 1A based on the current value of the first current and the first period, calculates, for each deposition-dissolution process, the second charge based on the current value of the second current and the second period, calculates a difference between the first charge and the second charge for each deposition-dissolution process, calculates the first current density for each deposition-dissolution process based on an electrode area of the working electrode and the current value of the first current, and concludes from analysis, based on the calculated first charge, second charge, and first current density, that the electroplating solution is in a state where charge that does not contribute to deposition of metal on the plated object decreases as a plating process is carried out under conditions that produce the first current density in a deposition-dissolution process where the difference in charge is small and where the charge that does not contribute to the deposition of metal on the plated object increases as the plating process is carried out under conditions that produce the first current density in a deposition-dissolution process where the difference in charge is large; a process Ca that calculates, for each deposition-dissolution process, the second charge based on the current value of the second current and the second period, calculates, for each deposition-dissolution process, the amount of metal deposited on the working electrode during the process 1A based on the second charge, calculates, for each deposition-dissolution process, the first current density based on the electrode area of the working electrode and the current value of the first current, specifies, based on the calculated amount of metal and first current density, a current density lower limit value for the first current density capable of depositing at least an amount of metal set in advance on the working electrode, and concludes from analysis that the electroplating solution is in a state where it is not possible to deposit at least the amount of metal set in advance on the plated object when a plating process is carried out under conditions that produce a first current density that falls below the current density lower limit value; a process Da that calculates, for each deposition-dissolution process, the second charge based on the current value of the second current and the second period, calculates, for each deposition-dissolution process, the amount of metal deposited on the working electrode during the process 1A based on the second charge, calculates, for each deposition-dissolution process, the first current density based on the electrode area of the working electrode and the current value of the first current, specifies, based on the calculated amount of metal and first current density, a current density upper limit value for the first current density capable of depositing at least an amount of metal set in advance on the working electrode, and concludes from analysis that the electroplating solution is in a state where it is not possible to deposit at least the amount of metal set in advance on the plated object when a plating process is carried out under conditions that produce a first current density that exceeds the current density upper limit value; a process Ea that concludes from analysis, based on the current value of the second current in each deposition-dissolution process, that impurities are included in the electroplating solution when the current value of the second current is at least a reference current value set in advance; and a process Fa that calculates, for each deposition-dissolution process, the first charge based on the current value of the first current and the first period, calculates, for each deposition-dissolution process, a third charge that does not contribute to dissolution of the metal out of the second charge, based on the current value of the second current and a state of changes in the current value of the second current in the second period, calculates, for each deposition-dissolution process, the first current density based on the electrode area of the working electrode and the current value of the first current, and concludes from analysis, based on the first current density, the first charge, and the third charge, that the electroplating solution is in a state where charge that contributes to the deposition of metal on the plated object increases as a plating process is carried out under conditions that produce the first current density during a deposition-dissolution process for which the ratio of the third charge to the first charge is large and where the charge that contributes to the deposition of metal on the plated object decreases as the plating process is carried out under conditions that produce the first current density during a deposition-dissolution process for which the ratio of the third charge to the first charge is small.

According to the electroplating solution analyzing apparatus according to the present invention, unlike the conventional analysis method that fabricates a plurality of samples with different conditions (carries out a plating process) and measures the amount of metal or the like deposited on the respective materials, it is possible, by executing a process (any of the processes Aa to Fa) in keeping with the desired factors to be analyzed, to accurately and easily analyze the state of the electroplating solution, even for a user unused to analyzing electroplating solution.

Also, the electroplating solution analyzing apparatus according to the present invention, as the measurement value acquiring process, the processing unit executes: a measurement value acquiring process 1a that uses, as the working electrode, a first electrode with at least an electrode surface formed of a first material with at least a preset level of insolubility in the electroplating solution; and a measurement value acquiring process 2a that uses, as the working electrode, a second electrode with at least an electrode surface formed by a second material that is the same as the plated object on which metal is to be deposited by the plating process and is configured such that an area of the electrode surface is the same as an area of the electrode surface of the first electrode, and sets the first period and the voltage value of the first voltage in the process 1A, and the second period, the voltage value and rate of change of the voltage value of the second voltage in the process 2A equal to the measurement value acquiring process 1a, and executes, as the analysis process, a process Ga that calculates, for each deposition-dissolution process, a fourth charge applied to the electroplating solution during the process 2A in the measurement value acquiring process 1a based on the current value of the second current and the second period for which the second current flowed in the measurement value acquiring process 1a, calculates, for each deposition-dissolution process, a fifth charge that contributes to dissolution of the metal during the process 2A in the measurement value acquiring process 2a based on the current value of the second current and a state of changes in the current value in the second period during the measurement value acquiring process 2a, calculates a sixth charge that is a difference between the fourth charge and the fifth charge for each deposition-dissolution process for which the voltage value of the first voltage applied during the process 1A is equal, calculates, for each deposition-dissolution process, the first current density based on the current value of the first current and the electrode area of a predetermined electrode out of the first electrode and the second electrode, and concludes from analysis, based on the calculated first current density and sixth charge, that the electroplating solution is in a state where a rate of dissolution per unit time of the plated object decreases as the plating process is carried out under conditions that produce a first current density for which the sixth charge is small and where the rate of dissolution per unit time of the plated object increases as the plating process is carried out under conditions that produce a first current density for which the sixth charge is large.

According to the electroplating solution analyzing apparatus according to the present invention, it is possible to easily and accurately analyze the extent to which the electroplating solution to be analyzed will dissolve the plated object due to an oxidation reaction during the plating process.

Also, the electroplating solution analyzing apparatus according to the present invention comprises a measuring unit capable of executing a measurement process that measures a current value of a current flowing between a counter electrode and a working electrode that have been placed in contact with an electroplating solution to be analyzed while applying a voltage to a reference electrode and the working electrode that have been placed in contact with an electroplating solution; and a processing unit that executes a measurement value acquiring process which controls the measuring unit to execute the measurement process and acquires measurement values and an analysis process that analyzes a state of the electroplating solution based on the acquired measurement values, wherein the processing unit executes, as the measurement value acquiring process, a process 1B that measures a current value of a first current that flows between the counter electrode and the working electrode as the measurement values while depositing metal on the working electrode by applying a first voltage with a voltage value set in advance between the reference electrode and the working electrode for a first period set in advance; and a process 2B that measures, as the measurement values, a current value of a second current that flows between the counter electrode and the working electrode with a cycle set in advance while dissolving the metal that was deposited on the working electrode in the process 1B into the electroplating solution by applying a second voltage whose voltage value changes with a rate of change set in advance between the reference electrode and the working electrode for a second period set in advance, in that order and analyzes, in the analysis process, the state of the electroplating solution based on the measurement values acquired by the measurement value acquiring process and reference values set in advance.

According to the electroplating solution analyzing apparatus according to the present invention, unlike the conventional analysis method where a deposition process is carried out on samples for analysis purposes using the electroplating solution to be analyzed and the state of the electroplating solution is analyzed by measuring the deposited state of the metal on such samples, it is possible to easily analyze the state of changes in the electroplating solution based on reference values that are values showing the state of the electroplating solution before the changes and measurement values that are values showing the state of changes in the electroplating solution, and when doing so, it is possible, by dissolving the metal that was deposited on the working electrode during the process 1B into the electroplating solution during the process 2B, to produce a state where no metal is deposited on the working electrode at the start of the next deposition-dissolution process. This means that it is possible to immediately start the next deposition-dissolution process and analyze the state of changes in the electroplating solution without replacing the working electrode or removing the metal deposited on the working electrode. By doing so, compared to the conventional analysis method where it is necessary to discard samples every time the state of changes in the electroplating solution is analyzed, it is possible to analyze the state of changes in the electroplating solution easily and at low cost.

Also, the electroplating solution analyzing apparatus according to the present invention, as the analysis process, the processing unit executes at least one of: a process Ab that calculates a second charge applied to the electroplating solution during the process 2B based on the current value of the second current and a second period for which the second current flowed between the counter electrode and the working electrode during the process 2B, and concludes from analysis, when the second charge is larger than a reference value A as the reference values, that the electroplating solution has changed to a state where the amount of metal deposited per unit time in a plating process is larger than a reference state A for which the measurement value acquiring process is capable of acquiring the reference value A, and when the second charge is smaller than the reference value A, that the electroplating solution has changed to a state where the amount of metal deposited per unit time in the plating process is less than the reference state A; a process Bb that calculates a first charge applied to the electroplating solution during the process 1B based on the current value of the first current and the first period, calculates the second charge based on the current value of the second current and the second period, and concludes from analysis, when a difference between the first charge and the second charge is smaller than a reference value B as the reference values, that the electroplating solution has changed to a state where charge that does not contribute to deposition of metal during the plating process is smaller than a reference state B for which the measurement value acquiring process is capable of acquiring the reference value B, and when the difference between the first charge and the second charge is larger than the reference value B, that the electroplating solution has changed to a state where charge that does not contribute to deposition of metal during the plating process is larger than a reference state B; a process Cb that concludes from analysis, when the current value of the second current is larger than a reference value C as the reference values, that an amount of impurities included in the electroplating solution has changed to a larger amount than a reference state C for which the measurement value acquiring process is capable of acquiring the reference value C, and when the current value of the second current is smaller than the reference value C, that the amount of impurities included in the electroplating solution has changed to a smaller amount than the reference state C; and a process Db that calculates the first charge based on the current value of the first current and the first period, calculates a third charge that contributes to dissolution of the metal out of the second charge based on the current value of the second current and a state of changes in the current value of the second current during the second period, concludes from analysis, when the ratio of the third charge to the first charge is larger than a reference value D as the reference values, that the electroplating solution has changed to a state where charge that contributes to deposition of metal during the plating process is larger than a reference state D where the measurement value acquiring process is capable of acquiring the reference value D, and when the ratio of the third charge to the first charge is smaller than the reference value D, that the electroplating solution has changed to a state where charge that contributes to deposition of metal during the plating process is smaller than the reference state D.

According to the electroplating solution analyzing apparatus according to the present invention, unlike the conventional analysis method that executes an analysis process on samples for analysis purposes and measures the deposited state of metal, by executing a process (any of the processes Ab to Db) in keeping with the desired factors to be analyzed, it is possible, even for a user who is unused to analysis of the electroplating solution, to easily and accurately analyze the state of changes in the electroplating solution.

Also, the electroplating solution analyzing apparatus according to the present invention, as the measurement value acquiring process, the processing unit executes: a measurement value acquiring process 1$b$ that uses, as the working electrode, a first electrode with at least an electrode surface formed of a first material with at least a preset level of insolubility in the electroplating solution; and a measurement value acquiring process 2$b$ that uses, as the working electrode, a second electrode with at least an electrode surface formed by a second material that is the same as the plated object on which metal is to be deposited by the plating process and is configured such that an area of the electrode surface is the same as an area of the electrode surface of the first electrode, and sets the first period and the voltage value of the first voltage in the process 1B, and the second period, the voltage value and rate of change of the voltage value of the second voltage in the process 2B equal to the measurement value acquiring process 1$b$, and executes, as the analysis process, a process Eb that calculates a fourth charge applied to the electroplating solution during the process 2B in the measurement value acquiring process 1$b$ based on the current value of the second current and the second period for which the second current flowed in the measurement value acquiring process 1$b$, calculates a fifth charge that contributes to dissolution of the metal during the process 2B in the measurement value acquiring process 2$b$ based on the current value of the second current and a state of changes in the current value during the second period in the measurement value acquiring process 2$b$, calculates a sixth charge that is a difference between the fourth charge and the fifth charge, and concludes from analysis, when the sixth charge is smaller than a reference value E as the reference values, that the electroplating solution has changed to a state where a rate of dissolution per unit time of the plated object is lower than a reference state E capable of calculating the sixth charge that is equal to the reference value E based on the measurement values acquired by the measurement value acquiring process 1$b$ and the measurement value acquiring process 2$b$, and when the sixth charge is larger than the reference value E, that the electroplating solution has changed to a state where a rate of dissolution per unit time of the plated object is higher than the reference state E.

According to the electroplating solution analyzing apparatus according to the present invention, it is possible to easily and accurately analyze the extent to which the electroplating solution to be analyzed has changed to a state that dissolves the plated object due to an oxidation reaction during the plating process.

It should be noted that the disclosure of the present invention relates to the contents of Japanese Patent Applications 2014-236183 and 2014-236185 that were filed on Nov. 21, 2014 and Japanese Patent Applications 2015-162997 and 2015-163000 that were filed on Aug. 20, 2015, the entire contents of which are herein incorporated by reference.

BRIEF DESCRIPTION OF THE DRAWINGS

These and other objects and features of the present invention will be explained in more detail below with reference to the attached drawings, wherein:

FIG. 4 is a diagram useful in explaining the relationship between a voltage value of a voltage applied between the reference electrode and the working electrode during processes 1A and 1B and charge applied to an electroplating solution during the processes 2A and 2B;

FIG. 5 is a diagram useful in explaining the relationship between an integrated current value of the current flowing between the counter electrode and the working electrode during the processes 2A and 2B and the concentration of impurities included in an electroplating solution;

FIG. 10 is a diagram useful in explaining an example of changes in the relationship between the voltage value of the voltage applied between the reference electrode and the working electrode during the process 2B and the current value of the current flowing between the counter electrode and the working electrode during the process 2B.

DESCRIPTION OF THE PREFERRED EMBODIMENTS

Figure 1:
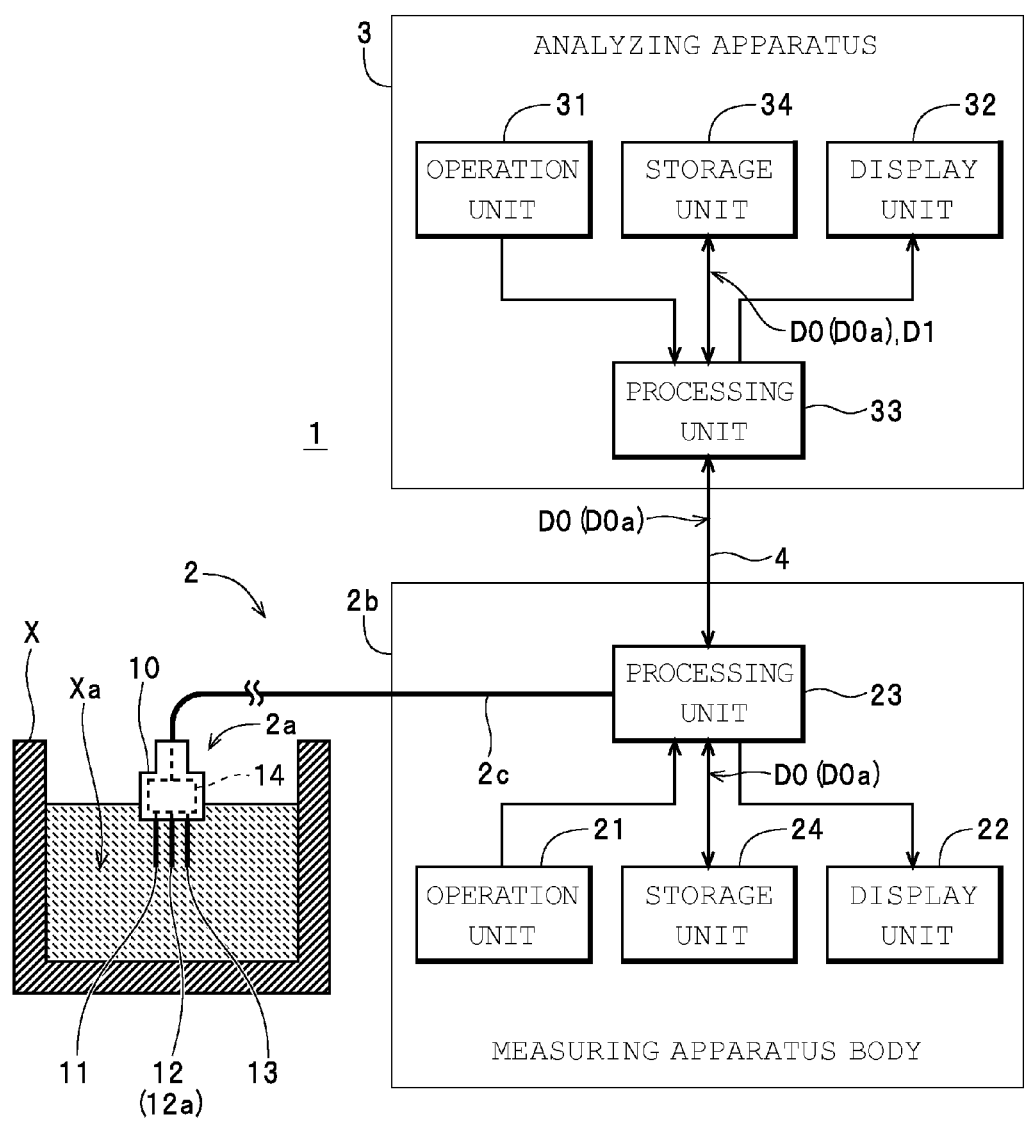
FIG. 1 is a schematic diagram of an electroplating solution analyzing system.

Embodiments of an electroplating solution analyzing apparatus are described below with reference to the attached drawings.

The electroplating solution analyzing system 1 is one example of an "electroplating solution analyzing apparatus" capable of analyzing the state of an electroplating solution (plating bath) Xa held within a plating solution tank X, and is equipped with an electrochemical measuring apparatus 2 and an analyzing apparatus 3.

The electrochemical measuring apparatus 2 is one example of a "measuring unit" and includes an electrochemical sensor 2a and a measuring apparatus body 2b. The electrochemical sensor 2a is a sensor apparatus for carrying out an electrochemical measurement process via three-electrode measurement, and includes a casing 10, a reference electrode 11, a working electrode 12 (12a), a counter electrode 13, and the signal processing circuit board 14. Note that in the present specification, for ease of understanding the "electroplating solution analyzing apparatus", the reference electrode 11, the working electrode 12 (12a), and the counter electrode 13 are illustrated with the same form and the same size and detailed description of the configurations of the electrodes 11, 12 (12a), and 13 is omitted. In reality, electrodes of various shapes, sizes, and configurations are used as the electrodes 11, (12a), and 13 in accordance with the type of the electroplating solution Xa to be measured (that is, to be analyzed by the electroplating solution analyzing system 1), the material of the plated object, and the like.

The casing 10 is a vessel formed of a chemically-resistant resin material (as examples, various engineering plastics such as PEEK (polyether ether ketone) resin and PTFE (polytetrafluoroethylene) resin). The electrodes 11, 12 (12a), and 13 are attached to the casing 10 and the signal processing circuit board 14 to which the electrodes 11, 12 (12a), and 13 are connected is housed inside the casing 10. The signal processing circuit board 14 is a circuit board on which a potentiostat, I/V conversion circuit and the like are mounted, and is connected via a signal cable 2c to the measurement apparatus body 2b. Note that the signal processing circuit board 14 may be configured as a component element on the measuring apparatus body 2b side.

In the present embodiment, as described later, as one example, when carrying out various analysis on an electroplating solution Xa that is capable of a plating process that plates nickel as one example of a "metal" on copper as one example of the "plated object", "measurement value acquiring processes 1a and 1b" that use a working electrode 12 (one example of a "first electrode") with an electrode surface formed of platinum (one example of a "first material") that has an extremely high level of insolubility in the electroplating solution Xa and "measurement value acquiring processes 2a and 2b" that use a working electrode 12a (one example of a "second electrode") with an electrode surface formed of copper (one example of a "second material") that is the same as the plated object are executed. Also, the working electrodes 12 and 12a are formed so that the respective electrode surfaces have the same area which is set equal to or smaller than the area of the electrode surfaces of the counter electrode 13 (as one example, the areas of the electrode surfaces of the working electrodes 12 and 12a and the counter electrode 13 are the same).

In addition, the working electrodes 12 and 12a are formed so that the respective lengths are the same and that the forms and thicknesses of end portions that are inserted into the casing 10 are the same. By doing so, with the electroplating solution analyzing system 1 (the electrochemical measuring apparatus 2) according to the present embodiment, as described later, by attaching the working electrode 12 to the casing 10 and connecting to the signal processing circuit board 14 when executing the "measurement value acquiring processes 1a and 1b" and by attaching the working electrode 12a to the casing 10 and connecting to the signal processing circuit board 14 when executing the "measurement value acquiring processes 2a and 2b", it is possible to make common use of component elements aside from the working electrodes 12 and 12a in the electrochemical sensor 2a during both types of "measurement value acquiring processes".

The measuring apparatus body 2b is equipped with an operation unit 21, a display unit 22, a processing unit 23, and a storage unit 24. The operation unit 21 is equipped with operation switches that are capable of a variety of operations, such as setting operations for measurement conditions, start/stop instructions for a measurement process, and instructions to transmit measurement results to the analyzing apparatus 3, and outputs operation signals corresponding to such operations to the processing unit 23. Under the control of the processing unit 23, the display unit 22 displays information such as measurement results of an electrochemical measurement process calculated by the processing unit 23.

The processing unit 23 carries out overall control of the electrochemical measuring apparatus 2. More specifically, the processing unit 23 carries out an electrochemical measurement process (one example of a "measurement process") in accordance with an operation signal from the operation unit 21. The processing unit 23 calculates measurement values based on a sensor signal outputted from the electrochemical sensor 2a, generates measurement value data D0 in which calculation results (measurement values) are recorded and stores the measurement value data D0 in the storage unit 24 (part of the "measurement value acquiring process"). In addition, the processing unit 23 reads the measurement value data D0 from the storage unit 24 in accordance with an operation signal from the operation unit 21 (or a control signal from the analyzing apparatus 3) and outputs the measurement value data D0 to the analyzing apparatus 3.

Here, together with the signal processing circuit board 14 of the electrochemical sensor 2a and a processing unit 33 of the analyzing apparatus 3 (described later), the processing unit 23 configures a "processing unit", and, in the electrochemical measurement process described above, carries out a process that applies a voltage between the reference electrode 11 and the working electrode 12 (12a) that have been placed in contact with the electroplating solution Xa to be analyzed and calculates the current value of the current that flows between the counter electrode 13 and the working electrode 12 (12a) that have been placed in contact with the electroplating solution Xa as a measurement value to generate the measurement value data D0. The storage unit 24 stores an operation program of the processing unit 23, the measurement value data D0 described above, and the like.

On the other hand, as one example, the analyzing apparatus 3 is constructed of a personal computer in which an analysis program for the electroplating solution analyzing system 1 has been installed, and is equipped with an operation unit 31, a display unit 32, the processing unit 33, and a storage unit 34. The operation unit 31 is constructed by a keyboard and a pointing device such as a mouse or a touch pad and outputs an operation signal in accordance with operation of such elements to the processing unit 33. The display unit 32 displays results (analysis results) of the "analysis process" carried out by the processing unit 33.

As mentioned earlier, the processing unit 33 constructs a "processing unit" together with the processing unit 23 of the electrochemical measuring apparatus 2 (the measuring apparatus body 2*b*) and executes (another part of the "measurement value acquiring process") that has the measurement value data D0 in which measurement values are recorded transmitted from the electrochemical measuring apparatus 2 (the measuring apparatus body 2*b*) and stored in the storage unit 34. Also, by analyzing the measurement value data D0 transmitted from the electrochemical measuring apparatus 2, the processing unit 33 analyzes the state of the electroplating solution Xa for each factor to be analyzed, described later, has the analysis results displayed on the display unit 32, generates analysis result data D1, in which the analysis results are recorded, and stores the analysis result data D1 in the storage unit 34 (one example of an "analysis process"). The storage unit 34 stores the analysis program described above, the measurement value data D0 transmitted from the electrochemical measuring apparatus 2, the analysis result data D1 generated by the processing unit 33, and the like.

First Embodiment

When analyzing the state of the electroplating solution Xa using the electroplating solution analyzing system 1 described above, first, the electrochemical measuring apparatus 2 is transported to the installed location of the plating solution tank X in which the electroplating solution Xa is held. In this case, in the electroplating solution analyzing system 1 according to the present embodiment, as described above, the electrochemical measuring apparatus 2 that executes the "measurement process" of the "measurement value acquiring process" and the analyzing apparatus 3 that executes the "analysis process" based on the measurement values acquired by the "measurement value acquiring process" are separately constructed. By doing so, with the electroplating solution analyzing system 1 according to the present embodiment, by taking only the electrochemical measuring apparatus 2 that has been separated from the analyzing apparatus 3 to the installed location of the plating solution tank X in which the electroplating solution Xa is held, it is possible to execute part (i.e., the measurement process) of the "measurement value acquiring process" using the electrochemical measuring apparatus 2 on its own.

Next, the electrochemical sensor 2*a* is assembled. Here, although it is possible to store the electrochemical sensor 2*a* in a state where the working electrode 12 (12*a*) and/or the counter electrode 13 is/are attached to the casing 10, when an electrode with a fluid path (such as a "silver/silver chloride electrode") is used as the reference electrode 11, it is necessary to carry out an operation where the reference electrode 11, which is stored by being immersed in a protective liquid to prevent volatilization of the liquid that forms the electrolyte path and changes in the amount of ions, is taken out of the protective liquid and attached to the casing 10. As another example, when executing the "measurement value acquiring process" in the order of the "measurement value acquiring process 1*a*" and the "measurement value acquiring process 2*a*", the working electrode 12 is attached to the casing 10. By doing so, a state is produced where the electrodes 11, 12, and 13 are attached to the casing 10 and connected to the signal processing circuit board 14 inside the casing 10. Next, by connecting the electrochemical sensor 2*a* to the measuring apparatus body 2*b* via the signal cable 2*c*, preparation for the start of the electrochemical measurement process by the electrochemical measuring apparatus 2 is carried out. Note that it is assumed that the setting operation for the conditions (measurement conditions) of the measurement processes described below has already been completed.

Next, as shown in FIG. 1, after the electrodes 11, 12, and 13 of the electrochemical sensor 2*a* have been immersed in the electroplating solution Xa in a state where the electrode surfaces contact the electroplating solution Xa, the measurement start switch of the measuring apparatus body 2*b* is operated and the "measurement value acquiring process 1*a*" as the "measurement value acquiring process" is started. In this case, in the electroplating solution analyzing system 1 (the electrochemical measuring apparatus 2), when the start of processing has been indicated, the processing unit 23 executes, as the "measurement value acquiring process", a "deposition-dissolution process" that executes the "process 1A (a process that obtains measurement values while depositing metal on the working electrode 12: deposition process)" and the "process 2A (a process that obtains measurement values while dissolving the metal deposited on the working electrode 12 into the electroplating solution)" in that order a plurality of times while changing the voltage value of the voltage applied between both electrodes 11 and 12 during the "process 1A".

Figure 2:
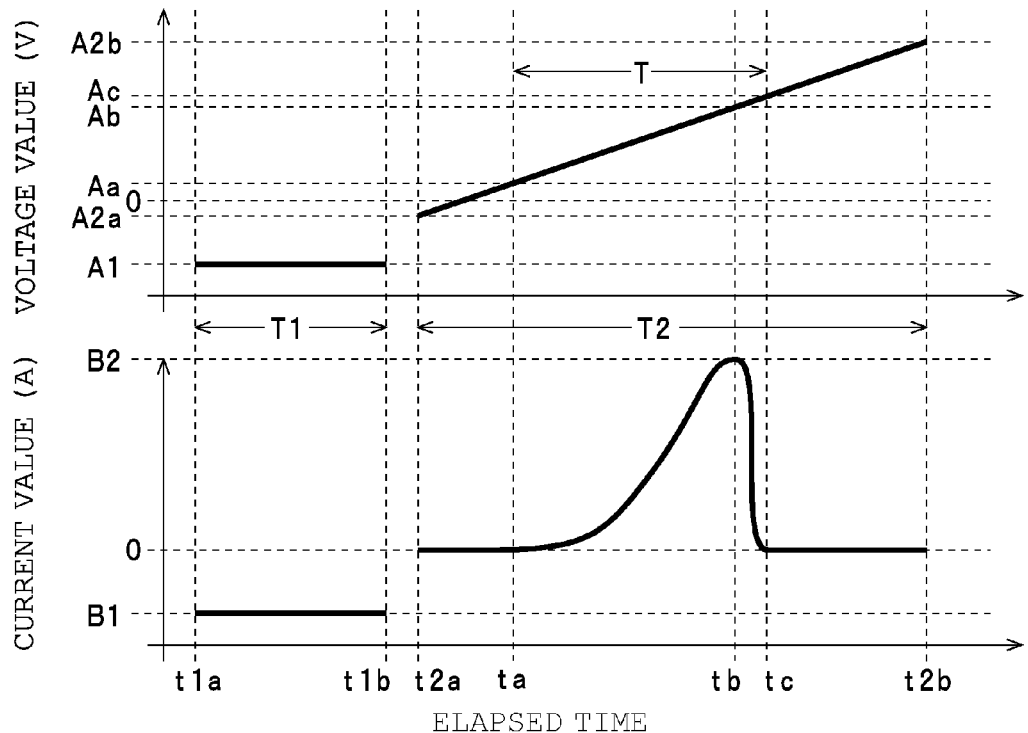
FIG. 2 is a diagram useful in explaining the relationship between a voltage value of a voltage applied between a reference electrode and a working electrode in a measurement value acquiring process and a current value of a current flowing between a counter electrode and the working electrode.

More specifically, as shown in FIG. 2, as the "process 1A" described above, the processing unit 23 applies a voltage (the potential of the working electrode 12 with respect to the reference electrode 11: one example of a "first voltage") with a voltage value A1 set in advance between the reference electrode 11 and the working electrode 12 for a period T1 (one example of a "first period": for example, 60 s) set in advance so as to deposit metal on the electrode surface of the working electrode 12 and measures a current value B1 of a current (one example of a "first current") that flows between the counter electrode 13 and the working electrode 12 with a cycle set in advance (the same cycle as the cycle for measuring current values during the "process 2A" described later: as one example, intervals of 10 ms).

In this case, during the "process 1A", since a fixed voltage (a voltage with the voltage value A1) is applied between the reference electrode 11 and the working electrode 12, as shown in the drawing, the measured current value B1 will be a constant value for the period T1 from time t1*a* to time t1*b*. Accordingly, for the "process 1A", instead of measuring the current value with a cycle set in advance, it is possible to use a configuration that measures the current value B1 only once during the period T1 (i.e., from time t1*a* to time t1*b*) where a voltage with the voltage value A1 is applied between the reference electrode 11 and the working electrode 12.

Also, as the "process 2A" mentioned above, the processing unit 23 applies a voltage (the potential of the working electrode 12 relative to the reference electrode 11: in the illustrated example, a voltage whose voltage value changes in a range of the voltage values A2*a* to A2*b*: one example of a "second voltage") whose voltage value changes with a rate of change (as one example, 10 mV/s) set in advance for a period T2 (one example of the "second period") set in advance between the reference electrode 11 and the working electrode 12 and measures the current value (in the illustrated example, a current value that changes in a range of the current values 0 to B2) of the current (one example of the "second current") flowing between the counter electrode 13 and the working electrode 12 with a cycle set in advance (as one example, 10 ms intervals) while dissolving the metal that was deposited onto the working electrode 12 during the "process 1A" described above into the electroplating solution Xa.

In this case, with the electroplating solution analyzing system 1 (the electrochemical measuring apparatus 2)

according to the present embodiment, whenever a "deposition-dissolution process" like that described above is executed, the voltage value A1 of the voltage applied between both electrodes 11 and 12 during the "process 1A" is changed in steps of 0.2V. As a specific example, when analyzing electroplating solution for nickel plating as the electroplating solution Xa to be analyzed, fifteen iterations of the "deposition-dissolution process" are successively executed while the voltage value A1 of the voltage applied between both electrodes 11 and 12 during the "process 1A" is increased in steps of 0.2V in a range of −3.4V to −0.6V, for example.

Note that the changed amount of the voltage value in each "process 1A" described above and the minimum value (in the above example, −3.4V) and the maximum value (in the above example, −0.6V) of the voltage applied during the "process 1A" are not limited to the example described above. Here, the voltage value of the voltage applied during the "process 1A" is changed in a range of voltage values set so as to produce a current density of the working electrode 12 within a current density range set in advance. More specifically, the minimum value of the applied voltage is set at a voltage value in accordance with the type of electroplating solution Xa so that during an actual plating process that uses the electroplating solution Xa, a current density that is sufficiently lower than a lower limit on the current density that is capable of depositing metal on the plated object is produced, and the maximum value of the applied voltage is set at a voltage value so that during an actual plating process that uses the electroplating solution Xa, a current density that is sufficiently higher than an upper limit on the current density that is capable of depositing metal on the plated object is produced. Note that as one example, favorable values for the "lower limit" and "upper limit" can be specified by executing processes (the "process 1A", the "process 2A" and "processes Ca and Da" described later) that are the same as the present embodiment on an unused electroplating solution Xa.

With the electroplating solution analyzing system 1 (electrochemical measuring apparatus 2) according to the present embodiment, each "deposition-dissolution process" is executed so that the voltage value range (voltage values A2a to A2b in FIG. 2) of the voltage applied between the reference electrode 11 and the working electrode 12 during the "process 2A" and the rate of change are the same voltage value range and rate of change. More specifically, as one example, when analyzing an electroplating solution for nickel plating as the electroplating solution Xa to be analyzed, in each "deposition-dissolution process", the voltage values A2a to A2b of the voltage applied between the reference electrode 11 and the working electrode 12 during the "process 2A" are changed at a rate of change of 10 mV/s in a range of −0.5 to 1.0V, for example.

Note that the minimum value (in the above example, −0.5V) and the maximum value (in the above example, 1.0V) and the rate of change (in the above example, 10 mV/s) of the voltage applied between both electrodes 11 and 12 during the "process 2A" are not limited to the example described above. In this case, the voltage value range of the voltage applied during the "process 2A" is set so that the current density of the working electrode 12 is within a current density range that is set in advance. More specifically, for the minimum value of the applied voltage (the lower limit value of the voltage value range), a voltage value that produces a current density that is sufficiently lower than the lower limit value of the current density that dissolves metal that has been deposited on the working electrode 12 by the "process 1A" into the electroplating solution Xa and also does not deposit metal (in the present embodiment, nickel) onto the working electrode 12 is set in accordance with the type of electroplating solution Xa, and for the maximum value of the applied voltage (the upper limit value of the voltage value range), a voltage value that produces a current density that is sufficiently higher than the upper limit value of the current density that dissolves metal that was deposited on the working electrode 12 by the "process 1A" into the electroplating solution Xa is set.

In this case, during the "process 2A" executed after metal has been deposited on the working electrode 12 by the "process 1A", the metal that was deposited on the working electrode 12 is dissolved back into the electroplating solution Xa by applying a voltage in the voltage value range described above between both electrodes 11 and 12 and when doing so, the current value of the current flowing between both electrodes 13 and 12 changes in accordance with the voltage value of the voltage applied between both electrodes 11 and 12. More specifically, in the example in FIG. 2 where metal is deposited on the working electrode 12 by applying a voltage with the voltage value A1 between both electrodes 11 and 12 for the period T1 from time t1a to time t1b during the "process 1A", when a voltage whose voltage value changes with a rate of change of 10 mV/s between both electrodes 11 and 12 for the period T2 from time t2a to time t2b during the "process 2A", a current flows between both electrodes 11 and 12 for the period T (one example of a "second period") from times ta to tc due to the metal deposited on the working electrode 12 being dissolved into the electroplating solution Xa.

Also, in the example shown in FIG. 2, when a voltage in a voltage value range from the voltage value A2a applied between both electrodes 11 and 12 at time t2a to the voltage value Aa applied between both electrodes 11 and 12 at time ta is applied between both electrodes 11 and 12, a current does not flow between both electrodes 12 and 13. That is, with the electroplating solution Xa in the illustrated example, when a voltage in the voltage value range of the voltage values A2a to Aa is applied between both electrodes 11 and 12, a state is produced where there is no deposition of metal onto the working electrode 12 and no dissolution of deposited metal into the electroplating solution Xa.

In addition, in the example shown in FIG. 2, the current value B2 of the current flowing between both electrodes 13 and 12 when a voltage with the voltage value Ab is applied between both electrodes 11 and 12 at the time tb reaches a maximum value, and when a voltage in the voltage value range from the voltage value Ac applied between both electrodes 11 and 12 at time tc to the voltage value A2b applied between both electrodes 11 and 12 at time t2b is applied between both electrodes 11 and 12, a current does not flow between both electrodes 12 and 13. That is, if the "process 1A" described above was executed using the electroplating solution Xa in the illustrated example, the metal deposited on the working electrode 12 is dissolved with the highest efficiency into the electroplating solution Xa when a voltage with the voltage value Ab is applied between both electrodes 11 and 12, all of the metal deposited on the working electrode 12 during the "process 1A" will have been dissolved into the electroplating solution Xa (a state where the electrode surface of the working electrode 12 is in direct contact with the electroplating solution Xa) at the time tc when a voltage with the voltage value Ac is applied between both electrodes 11 and 12, and after this, when a voltage in the voltage value range of the voltage values Ac to A2b is then applied between both electrodes 11 and 12, a state is produced where metal to be dissolved into the electroplating solution Xa is no longer present.

This means that by applying a voltage with a voltage value of the voltage value Ab or above to both electrodes 11 and 12 during the "process 2A" for a period that is sufficiently longer than the period from time tb to time tc, at the time t2b, the "deposition-dissolution process" will end in a state where metal is not deposited on the working electrode 12. Accordingly, in the electroplating solution analyzing system 1 according to the present embodiment, during the "process 2A" in each "deposition-dissolution process", by applying a voltage in a sufficiently wide voltage value range from the voltage value A2a that is sufficiently lower than the voltage value Aa described above and at which metal is not deposited onto the working electrode 12 to the voltage value A2b that is sufficiently higher than the voltage value Ab described above, it is possible, during the "deposition-dissolution process" executed following the present "deposition-dissolution process" to start the "process 1A" in a state where metal has not been deposited on the working electrode 12. By doing so, it is possible to execute the "deposition-dissolution process" consecutively for a plurality of iterations without carrying out an operation that removes metal from the working electrode 12 every time the "deposition-dissolution process" is executed or an operation that replaces the working electrode 12 every time the "deposition-dissolution process" is executed.

More specifically, in the present embodiment that analyzes the state of the electroplating solution Xa for nickel plating, as processing in a first iteration out of the fifteen iterations of the "deposition-dissolution process":

the "process 1A" that measures the current value B1 of the current flowing between the counter electrode 13 and the working electrode 12 while applying a voltage where the voltage value A1=−3.4V between the reference electrode 11 and the working electrode 12 for the period T1 from time t1a to time t1b; and the "process 2A" that measures the current value of the current flowing between the counter electrode 13 and the working electrode 12 while applying a voltage whose voltage value gradually increases in a range of −0.5V to 1.0V at a rate of change of 10 mV/s between the reference electrode 11 and the working electrode 12 for the period T2 from time t2a to t2b, are executed in that order.

Figure 3:
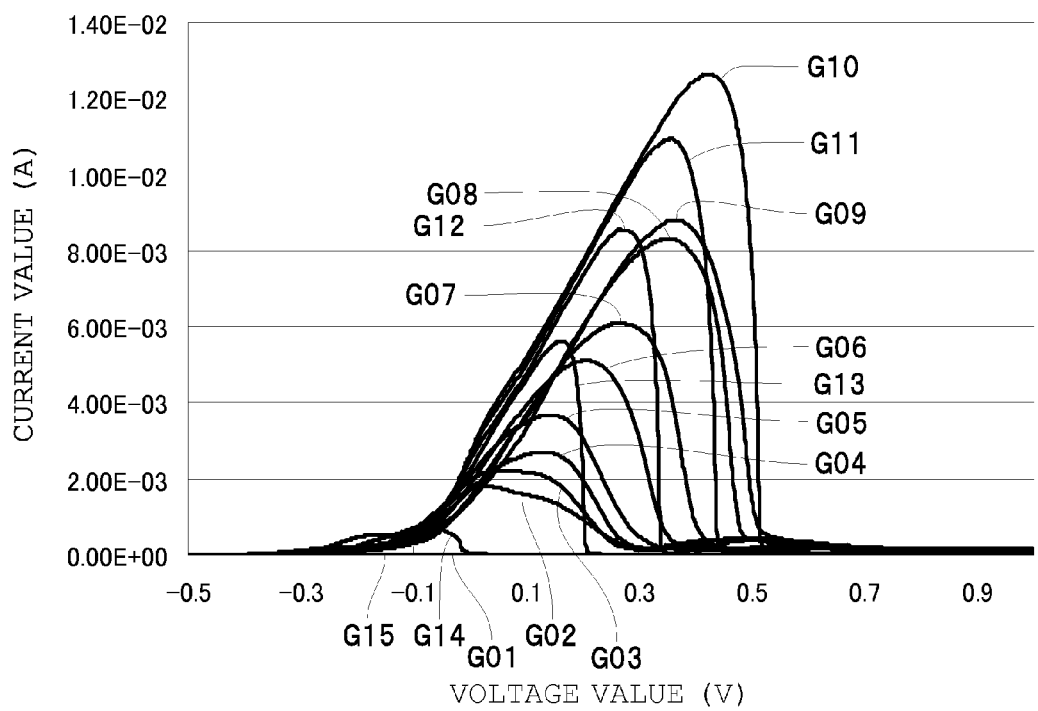
FIG. 3 is a diagram useful in explaining the relationship between a voltage value of a voltage applied between the reference electrode and the working electrode during processes 2A and 2B and a current value of a current flowing between a counter electrode and the working electrode during the processes 2A and 2B.

During the "process 2A" of the first iteration of the "deposition-dissolution process", as one example, current values shown by the graph G01 in FIG. 3 (in this example, a current value that hardly changes in the period T2) are measured. Accordingly, the processing unit 23 records the current value measured during the "process 1A" as part of the measurement value data D0 for the first iteration of the "deposition-dissolution process" in association with the voltage value A1=−3.4V of the voltage applied between both electrodes 11 and 12 and records a current value measured in a cycle set in advance (in the present embodiment, at 10 ms intervals) during the "process 2A" as another part of the measurement value data D0 for the first "deposition-dissolution process" in association with the voltage value of the voltage applied between both electrodes 11 and 12 when such measurements are made.

As the processing of the second iteration out of the fifteen iterations of the "deposition-dissolution process", the processing unit 23 executes the "process 1A" that measures the current value B1 of the current flowing between both electrodes 13 and 12 while applying a voltage where the voltage value A1=−3.2V between both electrodes 11 and 12 and the "process 2A" that measures the current value of the current flowing between both electrodes 13 and 12 while applying a voltage whose voltage value gradually increases in a range of −0.5V to 1.0V at a rate of change of 10 mV/s to both electrodes 11 and 12. At this time, during the "process 2A" of the second iteration of the "deposition-dissolution process", current values shown by the graph G02 are measured. Accordingly, the processing unit 23 records a current value measured during the "process 1A" as part of the measurement value data D0 for the second iteration of the "deposition-dissolution process" in association with the voltage value A1=−3.2V of the voltage applied between both electrodes 11 and 12 and records current values measured with a cycle set in advance during the "process 2A" as another part of the measurement value data D0 for the first "deposition-dissolution process" in association with the voltage value of the voltage applied between both electrodes 11 and 12 when such measurements are made.

After this, in the third and subsequent iterations of the "deposition-dissolution process", the voltage value of the voltage applied between both electrodes 11 and 12 during the "process 1A" is increased in steps of 0.2V in the manner of −3.0V, −2.8V, . . . and the current values shown in the graphs G03, G04, . . . are measured during the "process 2A". By doing so, when the fifteenth iteration of the "deposition-dissolution process" has been completed, a total of fifteen sets of measurement value data D0 for the fifteen iterations of the "deposition-dissolution processes" from the first to the fifteen iterations will have been stored in the storage unit 24. By doing so, the "measurement value acquiring process 1a" is completed.

Next, the "measurement value acquiring process 2a" is executed. More specifically, the electrochemical sensor 2a is pulled out from the plating solution tank X and the working electrode 12a is attached to the casing 10 in place of the working electrode 12. Next, various conditions such as the "first period" and the "voltage value of the first voltage" during the "process 1A" and the "second period", the "voltage value of the second voltage", and the "rate of change of the voltage value of the second voltage" during the "process 2A" as set in the same way as during the "measurement value acquiring process 1a", and fifteen iterations of the "deposition-dissolution process" are executed with the same procedure as during the "measurement value acquiring process 1a". By doing so, the "measurement value acquiring process 2a" is completed in a state where fifteen sets of measurement value data D0 are stored in the storage unit 24.

Note that in the following description, to distinguish between the sets of measurement value data D0 acquired by the "measurement value acquiring process 1a" that uses the working electrode 12 and the sets of measurement value data D0 acquired by the "measurement value acquiring process 2a" that uses the working electrode 12a, sets of measurement value data D0 acquired by the "measurement value acquiring process 2a" are referred to as the measurement value data D0a. By carrying out the above processing, all of the processing to be executed by the electrochemical measuring apparatus 2 is completed. Note that in the processing executed at the electrochemical measuring apparatus 2, in place of the example described above, it is also possible to execute the "measurement value acquiring process" in the order of the "measurement value acquiring process 2a" then the "measurement value acquiring process 1a".

Next, after the electrochemical sensor 2a has been pulled out from the plating solution tank X and the electrodes 11, 12a (12), and 13 have been removed from the casing 10 and housed in a case for storage purposes, the electrochemical measuring apparatus 2 is transported to the location where the analyzing apparatus 3 is installed and the measuring apparatus body 2*b* is connected to the analyzing apparatus 3 via a signal cable 4 (see FIG. 1). After this, by operating the operation unit 21 of the electrochemical measuring apparatus 2 (the measuring apparatus body 2*b*), the measurement value data D0 and D0*a* stored in the storage unit 24 are transmitted to the analyzing apparatus 3. In accordance with this, at the analyzing apparatus 3, the processing unit 33 stores the measurement value data D0 and D0*a* transmitted from the electrochemical measuring apparatus 2 in the storage unit 34. Note that the transmission of the measurement value data D0 and D0*a* from the electrochemical measuring apparatus 2 to the analyzing apparatus 3 is not limited to the above example of operating the operation unit 21 of the electrochemical measuring apparatus 2 and it is also possible to have the measurement value data D0 and D0*a* transmitted from the electrochemical measuring apparatus 2 to the analyzing apparatus 3 by operating the operation unit 31 of the analyzing apparatus 3 to transmit a transmission request signal from the analyzing apparatus 3 to the electrochemical measuring apparatus 2. By doing so, a state where the measurement value data D0 and D0*a* necessary for analyzing the electroplating solution Xa are stored in the storage unit 34 of the analyzing apparatus 3 is produced and the "measurement value acquiring process" is completed.

Next, the "analysis process" is executed at the analyzing apparatus 3. Here, in the electroplating solution analyzing system 1 according to the present embodiment, as described above, when a plurality of iterations (in the present embodiment, fifteen iterations) of the "deposition-dissolution process" are executed during each "measurement value acquiring process" (the "measurement value acquiring process 1*a*" and the "measurement value acquiring process 2*a*") described above using the electrochemical measuring apparatus 2, during the "process 1A" in each "deposition-dissolution process", the voltage value of the voltage applied between the reference electrode 11 and the working electrode 12 (12*a*) is changed and metal is deposited on the working electrode 12 (12*a*). For this reason, by respectively executing the "deposition-dissolution process" for the fifteen iterations described above and obtaining the measurement value data D0 and D0*a*, it is possible to analyze the state of the electroplating solution Xa based on the measurement value data D0 and D0*a* acquired by executing the deposition-dissolution process without having to fabricate a plurality of types of samples that have been plated using a different voltage value of the voltage applied between the electrode and the sample.

More specifically, in the electroplating solution analyzing system 1 (analyzing apparatus 3) according to the present embodiment, the processing unit 33 executes an analysis process (a process that analyzes the state of the electroplating solution Xa) during the "processes Aa to Ga" described later based on the measurement value data D0 and D0*a* of each "deposition-dissolution process", displays the analysis results on the display unit 32, generates the analysis result data D1 showing the analysis results, and stores the analysis result data D1 in the storage unit 34. Note that although it is possible to execute the analysis processes aside from the "process Ga" using only the measurement value data D0*a* acquired by the "measurement value acquiring process 2*a*" that uses the working electrode 12*a* or using both the measurement value data D0 and D0*a*, for ease of understanding the configuration of the "electroplating solution analyzing apparatus", an example will be described where the analysis processing during the "processes Aa to Fa" is executed using only the measurement value data D0.

First, as the "process Aa", a process that analyzes the state of the relationship between the voltage (current density) applied between the plated object (cathode) and the electrode (anode) during the plating process that uses the electroplating solution Xa to be analyzed and the amount of metal deposited per unit time on the plated object is executed based on the sets of measurement value data D0 described above acquired by the "measurement value acquiring process".

Here, the surface area of the plated object on which metal (in the present embodiment, nickel) is to be deposited (in an actual plating process) using the electroplating solution Xa to be analyzed differs to the electrode area of the working electrode 12 on which metal (in the present embodiment, nickel) is deposited in the "measurement value acquiring process" described above. This means that even if a voltage with a voltage value that is the same as the voltage applied between both electrodes 11 and 12 during the "process 1A" described above using the electrochemical sensor 2*a* (the working electrode 12) is applied to the plated object and the electrode (anode), the amount of metal deposited per unit area, the magnitude of the charge that contributes to deposition of metal, and the like will differ to the "process 1A" that uses the electrochemical sensor 2*a*. Accordingly, in the electroplating solution analyzing system 1 according to the present embodiment, a configuration is used that calculates, in place of the voltage value of the voltage applied when depositing metal, the current density corresponding to the voltage value of the applied voltage (the current density of the cathode), associates the calculated current density and the parameters of the factors to be analyzed to produce the analysis results of the "analysis process".

More specifically, in the "process Aa", first, based on the current value of a "second current" and a "second period" where the "second current" flows between the counter electrode 13 and the working electrode 12 during the "process 2A", a process that calculates the "second charge" applied to the electroplating solution Xa during the "process 2A" is executed for each "deposition-dissolution process", and the "first current density" is calculated for each "deposition-dissolution process" based on the electrode area of the working electrode 12 and the current value of the "first current".

More specifically, as one example, for the example of the "deposition-dissolution process" shown in FIG. 2, the charge (second charge) applied to the electroplating solution Xa during the "process 2A" is calculated based on an integrated value (an integrated current value) for the current values (current values sampled at 10 ms intervals) that changed from the current value 0 to the current value B2 for the period T from time ta to time tc and the period T where a current flowed between both electrodes 13 and 12. Also, the current density (first current density) of the working electrode 12 is calculated based on the electrode area of the working electrode 12 and the integrated value (integrated current value) of the current value B1 (each current value B1 that is sampled at 10 ms intervals in the present embodiment) of the current that flows between both electrodes 13 and 12 in a state where a voltage is applied between both electrodes 11 and 12 for the period T1 from time t1*a* to t1*b*. This calculation process is individually executed for each set of measurement value data D0 of the fifteen iterations of the "deposition-dissolution process".

Next, the state of the electroplating solution Xa is analyzed based on the calculated values of the "second charge" and the "first current density". More specifically, the analysis concludes that the electroplating solution Xa to be analyzed is in a state where the amount of metal deposited per unit time on the plated object increases as the plating process is carried out under conditions that produce the "first current density" during a "deposition-dissolution process" that has a large "second charge" calculated based on the measurement value data D0, and where the amount of metal deposited per unit time on the plated object decreases as the plating process is carried out under conditions that produce the "first current density" during a "deposition-dissolution process" that has a small "second charge". Accordingly, based on the analysis results (the analysis result data D1) of the "process Aa", it is possible to specify the "current density" that is capable of depositing a desired amount of metal per unit time on the plated object during a plating process that uses the electroplating solution Xa to be analyzed.

Also, as the "process Ba", a process that analyzes the state of the relationship between the current density in a plating process that uses the electroplating solution Xa to be analyzed and the amount of charge that does not contribute to deposition of metal on the plated object out of the charge applied to the electroplating solution Xa (the analysis process that relates to "current efficiency: cathode efficiency") is executed based on the measurement value data D0 described above acquired by the "measurement value acquiring process".

More specifically, in the "process Ba", first the "first charge" applied to the electroplating solution Xa during the "process 1A" is calculated for each "deposition-dissolution process" based on the current value of the "first current" and the "first period", the "second charge" is calculated for each "deposition-dissolution process" based on the current value of the "second current" and the "second period", the difference between the "first charge" and the "second charge" is calculated for each "deposition-dissolution process", and the "first current density" is calculated for each "deposition-dissolution process" based on the electrode area of the working electrode 12 and the current value of the "first current".

More specifically, in the example of the "deposition-dissolution process" shown in FIG. 2, based on the integrated value of the current value B1 of the current flowing between both electrodes 13 and 12 in a state where a voltage is applied between both electrodes 11 and 12 for the period T1 from time t1a to t1b (in the present embodiment, current values B1 sampled at 10 ms intervals) and the period T1 for which a current flowed between both electrodes 13 and 12, the charge (first charge) applied to the electroplating solution Xa during the "process 1A" is calculated. Also, the charge (second charge) applied to the electroplating solution Xa during the "process 2A" is calculated based on the integrated value of the current value that changes from the current value 0 to the current value B2 during the period T from time ta to time tc (the current values sampled at 10 ms intervals) and the period T for which a current flowed between both electrodes 13 and 12. In addition, the difference between the "first charge" and the "second charge" described above is calculated. Also, the current density (first current density) at the working electrode 12 is calculated based on the electrode area of the working electrode 12 and the integrated value of the current value B1 (in the present embodiment, the current values B1 sampled at 10 ms interval) of the current that flows between both electrodes 13 and 12 in a state where a voltage is applied between both electrodes 11 and 12 during the period T1 from time t1a to time t1b. This calculation process is executed for each measurement value data D0 of the fifteen iterations of the "deposition-dissolution process".

Next, the state of the electroplating solution Xa is analyzed based on the calculated values of the "first charge", the "second charge" and the "first current density". More specifically, the analysis concludes that the electroplating solution Xa to be analyzed is in a state where the charge that does not contribute to the deposition of metal on the plated object decreases (i.e., the "current efficiency: cathode efficiency" improves) as the plating process is carried out under conditions that produce the "first current density" during a "deposition-dissolution process" where the "difference in charge" calculated based on the measurement value data D0 was small, and where the charge that does not contribute to the deposition of metal on the plated object increases (i.e., the "current efficiency: cathode efficiency" worsens) as the plating process is carried out under conditions that produce the "first current density" during a "deposition-dissolution process" where the "difference in charge" was large. Accordingly, based on the analysis results (the analysis result data D1) of the "process Ba", it is possible to specify the "current density" that enables the desired amount of metal to be deposited on the plated object with a desired "current efficiency: cathode efficiency" during a plating process that uses the electroplating solution Xa to be analyzed.

In addition, as the "process Ca", a process (an analysis process relating to "critical current density (lower limit value)", "uniform electrodeposition (lower limit)" and "covering power") that specifies, based on the sets of measurement value data D0 described above that have been acquired by the "measurement value acquiring process", a lower limit value ("current density lower limit value) of the current density that is capable of depositing at least an amount of metal set in advance on the plated object during a plating process that uses the electroplating solution Xa to be analyzed is executed.

More specifically, in the "process Ca", first the "second charge" is calculated for each "deposition-dissolution process" based on the current value of the "second current" and the "second period", the amount of metal deposited on the working electrode 12 during the "process 1A" is calculated for each "deposition-dissolution process" based on each "second charge", and the "first current density" is calculated for each "deposition-dissolution process" based on the electrode area of the working electrode 12 and the current value of the "first current".

Here, the larger the amount of metal deposited on the working electrode 12 during the "process 1A" described earlier, the higher the charge applied to the electroplating solution Xa during the "process 2A" to have such metal dissolved into the electroplating solution Xa, and the smaller the amount of metal deposited on the working electrode 12 during the "process 1A", the lower the charge applied to the electroplating solution Xa during the "process 2A" to have such metal dissolved into the electroplating solution Xa. Accordingly, by calculating the charge applied to the electroplating solution Xa during the "process 2A", it is possible to specify the amount of metal deposited on the working electrode 12 during the "process 1A". More specifically, it is possible to calculate the amount of metal deposited on the cathode according to "charge/(valence of metal×Faraday constant).

By doing so, as shown by the line graph G in FIG. 4, the relationship is specified between the "first current density"

(the voltage value of the "first voltage" applied between both electrodes 11 and 12 in FIG. 4) in each "deposition-dissolution process" and the amount of metal deposited on the working electrode 12 during each "deposition-dissolution process" (in FIG. 4, the charge applied to the electroplating solution Xa during the "process 2A": the charge required to dissolve the metal that was deposited on the working electrode 12 into the electroplating solution Xa).

Next, the state of the electroplating solution Xa is analyzed based on the calculated amount of metal and "first current density". More specifically, the "current density lower limit value" of the "first current density" that is capable of depositing at least an amount of metal set in advance on the working electrode 12 is specified and the analysis concludes that the electroplating solution Xa is in a state where it is not possible to deposit at least the amount of metal set in advance on the plated object when the plating process is carried out under conditions that produce a "first current density" that falls below the "current density lower limit value". Here, in the present embodiment, as shown in FIG. 4, the current density of the working electrode 12 during the first iteration of the "deposition-dissolution process" when the voltage value of the "first voltage" applied between both electrodes 11 and 12 during the "process 1A" is −3.4V is specified as the lower limit value of the "critical current density" and the analysis concludes that metal will not be deposited on the plated object when a plating process is carried out at a current density that falls below such current density. Note that "uniform electrodeposition (lower limit)" and "covering power" will be described later for the "process Da".

On the other hand, as the "process Da", a process (an analysis process relating to "critical current density (upper limit value)", "uniform electrodeposition (upper limit)" and "covering power") that specifies an upper limit value of the current density ("critical current density upper limit value") that is capable of depositing at least an amount of metal set in advance on the plated object during a plating process that uses the electroplating solution Xa to be analyzed based on the sets of measurement value data D0 described above acquired by the "measurement value acquiring process" is executed.

More specifically, in the "process Da", in the same way as the "process Ca" described above, the "second charge" is calculated for each "deposition-dissolution process" based on the current value of the "second current" and the "second period", the amount of metal deposited on the working electrode 12 during the "process 1A" is calculated for each "deposition-dissolution process" based on each "second charge", and the "first current density" is calculated for each "deposition-dissolution process" based on the electrode area of the working electrode 12 and the current value of the "first current".

Next, the state of the electroplating solution Xa is analyzed based on the calculated amount of metal and "first current density". More specifically, the "current density upper limit value" of the "first current density" that is capable of depositing at least an amount of metal set in advance on the working electrode 12 is specified and the analysis concludes that the electroplating solution Xa is in a state where it is not possible to deposit at least the amount of metal set in advance on the plated object when the plating process is carried out under conditions where the "first current density" exceeds the "current density upper limit value". Here, in the present embodiment, as shown in FIG. 4, the current density of the working electrode 12 during the fifteenth iteration of the "deposition-dissolution process" when the voltage value of the "first voltage" applied between both electrodes 11 and 12 during the "process 1A" is −0.6V is specified as the upper limit value of the "critical current density", and the analysis concludes that metal will not be deposited on the plated object when a plating process is carried out at a current density that exceeds such current density.

Next, the state of the electroplating solution Xa relating to "uniform electrodeposition" is analyzed from the calculation results of the "process Ca" and the "process Da" described above. Here, during a plating process that uses the electroplating solution Xa to be analyzed, the voltage value of the voltage applied between the plated object and the electrode may vary within a certain range, such as when equipment aside from the plating process apparatus is started or stopped. Accordingly, it is necessary to specify a current density range where there is no large variation in the amount of metal deposited on the plated object even when the voltage value of the voltage applied between the plated object and the electrode varies (i.e., a range where uniform electrodeposition is ensured).

As one example, as shown in FIG. 4, when it has been defined that "uniform electrodeposition" of the product is ensured by keeping the range in which charge applied to the electroplating solution Xa (that is, the amount of metal deposited on the working electrode 12) during the "process 2A" changes due to variation in the voltage value of the "first voltage" applied between both electrodes 11 and 12 during the "process 1A" to a range where the charge is Ca1 to Ca2, the analysis concludes that the plating process should be executed within a current density range corresponding to the range Ha with the voltage values Va1 to Va2. Note that the range of charge (the range of the amount of metal) analyzed as ensuring "uniform electrodeposition" of products is set in advance by the user.

Next, the state of the electroplating solution Xa relating to "covering power" is analyzed from the calculation results of the "process Ca" and the "process Da" described above. Here, as shown in FIG. 4, when it has been defined that the "covering power" for products is sufficient when an amount of metal that requires at least a charge of Cb as the charge applied to the electroplating solution Xa during the "process 2A" has been deposited, for example, the analysis concludes that it is sufficient to execute the plating process with a current density range corresponding to the range Hb with the voltage values Vb1 to Vb2. Note that the range of charge (the range of the amount of metal) analyzed as ensuring a sufficient "covering power" of products is also set in advance by the user.

In addition, as the "process Ea", a process that analyzes whether impurities are included in the electroplating solution Xa to be analyzed and when present, what amount of impurities is included is executed based on the sets of measurement value data D0 described above acquired by the "measurement value acquiring process". More specifically, based on the current value of the "second current" in each "deposition-dissolution process", the analysis concludes that impurities are included in the electroplating solution Xa when the current value of the "second current" is at least a reference current value that has been set in advance.

Figure 6:
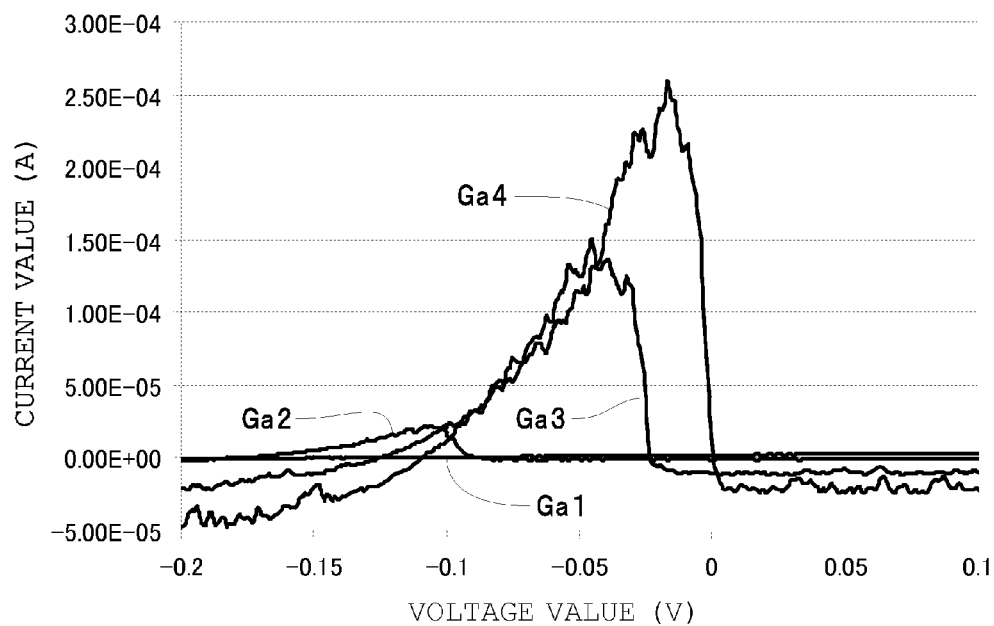
FIG. 6 is a diagram useful in explaining differences in the relationship between the voltage value of the voltage applied to the reference electrode and the working electrode during the processes 2A and 2B and the current value of the current flowing between the counter electrode and the working electrode during the processes 2A and 2B due to the presence of impurities (concentration of impurities)

More specifically, as shown in FIG. 6, if impurities are not mixed in the electroplating solution Xa in the "deposition-dissolution process" for which the voltage value of the "first voltage" applied between both electrodes 11 and 12 during the "process 1A" was −0.6V, for example, the current values of the "second current" flowing between both electrodes 13 and 12 during the "process 2A" are the values shown by the graph Ga1. However, when 100 ppm of copper sulfate are mixed into the electroplating solution Xa, the current values of the "second current" flowing between both electrodes 13 and 12 during the "process 2A" are the values shown by the graph Ga2, when 500 ppm of copper sulfate are mixed into the electroplating solution Xa, the current values of the "second current" flowing between both electrodes 13 and 12 during the "process 2A" are the values shown by the graph Ga3, and when 1000 ppm of copper sulfate are mixed into the electroplating solution Xa, the current values of the "second current" flowing between both electrodes 13 and 12 during the "process 2A" are the values shown by the graph Ga4. Accordingly, by comparing the current values shown by the graph Ga1 (current values measured in a state where no impurities such as copper sulfate are mixed in) and the current values actually measured during the "process 2A", it is possible to specify whether copper sulfate is mixed into the electroplating solution Xa.

Figure 7:
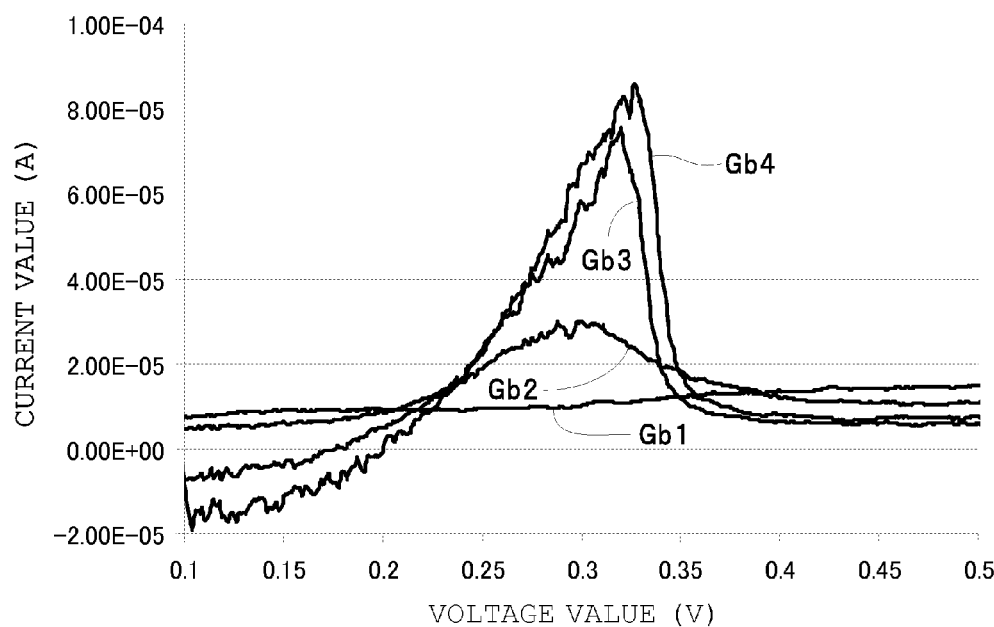
FIG. 7 is another diagram useful in explaining differences in the relationship between the voltage value of the voltage applied to the reference electrode and the working electrode during the processes 2A and 2B and the current value of the current flowing between the counter electrode and the working electrode during the processes 2A and 2B due to the presence of impurities (concentration of impurities)

In the same way, as shown in FIG. 7, if impurities are not mixed in the electroplating solution Xa in the "deposition-dissolution process" for which the voltage value of the "first voltage" applied between both electrodes 11 and 12 during the "process 1A" is −1.6V, for example, the current values of the "second current" flowing between both electrodes 13 and 12 during the "process 2A" are the values shown by the graph Gb1. However, when 100 ppm of copper sulfate are mixed into the electroplating solution Xa, the current values of the "second current" flowing between both electrodes 13 and 12 during the "process 2A" are the values shown by the graph Gb2, when 500 ppm of copper sulfate are mixed into the electroplating solution Xa, the current values of the "second current" flowing between both electrodes 13 and 12 during the "process 2A" are the values shown by the graph Gb3, and when 1000 ppm of copper sulfate are mixed into the electroplating solution Xa, the current values of the "second current" flowing between both electrodes 13 and 12 during the "process 2A" are the values shown by the graph Gb4. Accordingly, by also comparing the current values shown by the graph Gb1 (current values measured in a state where no impurities such as copper sulfate are mixed in) and the current values actually measured during the "process 2A", it is possible to specify whether copper sulfate is mixed into the electroplating solution Xa.

Here, the applicant has confirmed that the integrated current value of the current value flowing between both electrodes 13 and 12 during the "process 2A" and the concentration of copper sulfate included in the electroplating solution Xa are in a proportional relationship, and that such proportional relationship differs according to the voltage value applied between both electrodes 11 and 12 during the "process 1A". More specifically, like the example in FIG. 6, when the voltage value of the "first voltage" applied between both electrodes 11 and 12 during the "process 1A" is −0.6V, the relationship between the integrated current value and the concentration of copper sulfate during the "process 2A" is the relationship shown by the approximation line Ga in FIG. 5. Also, like the example in FIG. 7, when the voltage value of the "first voltage" applied between both electrodes 11 and 12 during the "process 1A" is −1.6V, the relationship between the integrated current value and the concentration of copper sulfate during the "process 2A" is the relationship shown by the approximation line Gb in FIG. 5.

Accordingly, in this example, it is possible to specify the concentration of copper sulfate mixed into the electroplating solution Xa based on either the integrated current value in the "process 2A" when the voltage value of the "first voltage" is −0.6V or the integrated current value in the "process 2A" when the voltage value of the "first voltage" is −1.6V. Here, as one example, when trying to specify the concentration of copper sulfate based on only the integrated current value in the "process 2A" when the voltage value of the "first voltage" is −0.6V, if a measurement error occurs during the "process 2A", there is the risk that the specified concentration of the copper sulfate will be inaccurate. Accordingly, by specifying the concentration of copper sulfate based on both integrated current values during the "process 2A" when the voltage value of the "first voltage" is −0.6V and when the voltage value of the "first voltage" is −1.6V, it is possible to specify an accurate concentration.

As the "process Fa", a process (another analysis process relating to "current efficiency: cathode efficiency") that analyzes, based on the sets of measurement value data D0 acquired by the measurement value acquiring process, the state of the relationship between the current density in a plating process that uses the electroplating solution Xa to be analyzed and the amount of charge that contributes to the deposition of metal on the plated object out of the charge applied to the electroplating solution Xa is executed.

Here, although the "process Fa" has an analysis procedure that resembles the "process Ba" described above which concludes that the charge that does not contribute to the deposition of metal decreases as the plating process is carried out under conditions that produce a current density where the difference between the "first charge" and the "second charge" is small, the analysis procedure of the "process Fa" differs to the "process Ba" by concluding that the charge that contributes to the deposition of metal increases when the plating process is carried out with conditions that produce a current density for which the ratio of the "third charge that contributes to dissolution of metal out of the second charge" to the "first charge" is high. More specifically, in the "process Fa" first, the "first charge" is calculated for each deposition-dissolution process based on the current value of the "first current" and the "first period", the "third charge" that contributes to the dissolution of metal out of the "second charge" is calculated for each deposition-dissolution process based on the current value of the "second current" and the "state of change in the current value during the second period", and the "first current density" is calculated for each "deposition-dissolution process" based on the electrode area of the working electrode 12 and the current value of the "first current".

Figure 8:
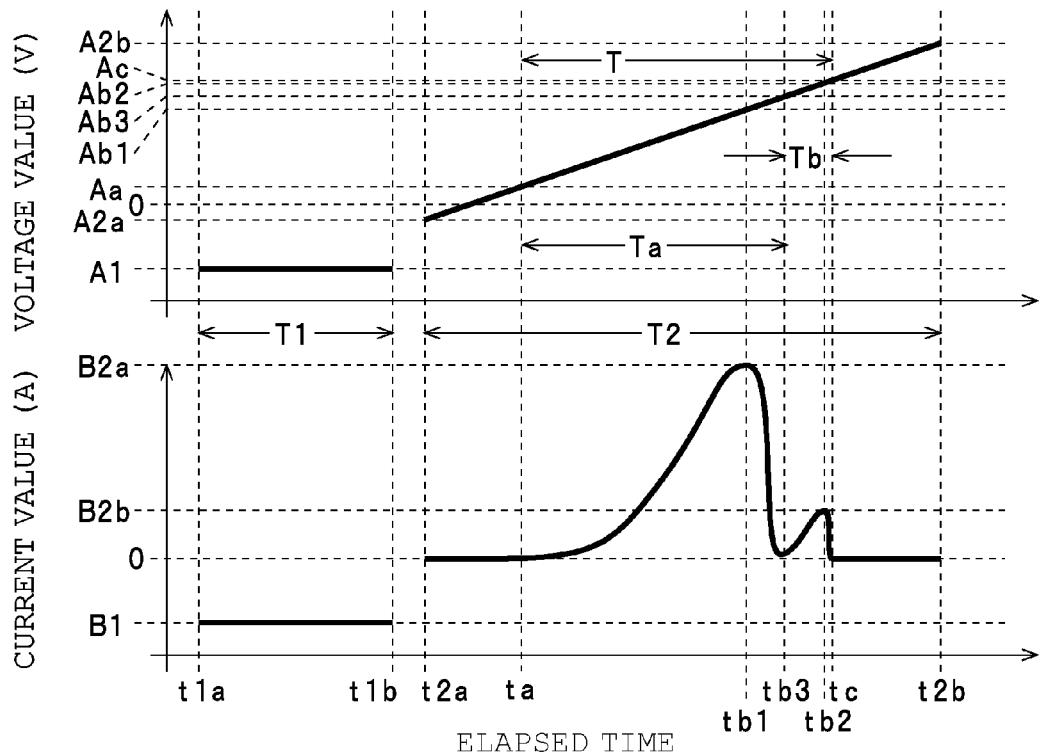
FIG. 8 is another diagram useful in explaining the relationship between the voltage value of the voltage applied between the reference electrode and the working electrode in the measurement value acquiring process and the current value of the current flowing between the counter electrode and the working electrode.

More specifically, in the example of the "deposition-dissolution process" shown in FIG. 8, in the same way as the "process Ba" described earlier, the current value (the first current density) during the "process 1A" is calculated and the charge (first charge) that is applied to the electroplating solution Xa for the period T1 during the "process 1A" is calculated. The "third charge" is also calculated based on the current values (current values sampled at 10 ms intervals) that change between the current value 0 to the current value B2a during the period T2 from time t2a to time t2b.

Note that the example in FIG. 8 shows an example where the "process 1A" and the "process 2A" have been executed for electroplating solution Xa that includes impurities. This means that in the example in FIG. 8, when a voltage whose voltage value changes with a rate of change of 10 mV/s for the period T1 from time t2a to time t2b during the "process 2A" is applied between both electrodes 11 and 12, a current that changes from the current value 0 to the current value B2a for the period Ta from time ta to time tb3 flows between both electrodes 13 and 12 due to the dissolution of metal deposited on the working electrode 12, and after this, a current that changes from the current value 0 to the current value B2b during the period Tb from time tb3 to time tc flows between both electrodes 13 and 12 due to the dissolution of impurities deposited on the working electrode 12.

Here, the voltage value at which impurities are dissolved into the electroplating solution Xa during the "process 2A" differs to the voltage value at which metal is dissolved into the electroplating solution Xa. For this reason, based on the state of changes in the current value (a current value sampled at 10 ms intervals) of the current flowing between both electrodes 13 and 12 for the period T from time ta to tc during the "process 2A", it is possible to specify a period for which a current flowed between both electrodes 13 and 12 due to the dissolution of metal and a period for which a current flowed between both electrodes 13 and 12 due to the dissolution of impurities.

More specifically, in the example in FIG. 8, the amount of metal dissolved from the working electrode 12 into the electroplating solution Xa reaches a maximum at the time tb1 when the voltage applied between both electrodes 11 and 12 reaches the voltage value Ab1 (where the current flowing between both electrodes 13 and 12 reaches the current value B2a), most of the metal deposited on the working electrode 12 will have been dissolved into the electroplating solution Xa at the time tb3 where the applied voltage reaches the voltage value Ab3, at the same time, dissolution of impurities from the working electrode 12 into the electroplating solution Xa starts, the amount of impurities dissolved from the working electrode 12 into the electroplating solution Xa reaches a maximum at the time tb2 when the applied voltage reaches the voltage value Ab2 (where the current flowing between both electrodes 13 and 12 reaches the current value B2b), and all of the impurities deposited on the working electrode 12 will have been dissolved into the electroplating solution Xa at the time tc where the applied voltage reaches the voltage value Ac.

Accordingly, in the example in FIG. 8, the charge (the third charge) that contributes to the "deposition of metal" out of the charge (the second charge) applied to the electroplating solution Xa during the "process 2A" is calculated based on the integrated value of the current value that changes from the current value 0 to the current value B2a (the current value of the current that flows between both electrodes 13 and 12 due to the dissolution of metal) for the period Ta from time ta to time tb3 and the period Ta for which a current flowed between both electrodes 13 and 12. This calculation process is executed for each set of measurement value data D0 of the fifteen iterations of the "deposition-dissolution process".

Next, the state of the electroplating solution Xa is analyzed based on the calculated values of the "first current density", the "first charge" and the "third charge". More specifically, the analysis concludes that the electroplating solution Xa to be analyzed is in a state such that the charge that contributes to deposition of metal onto the plated object increases (i.e., the "current efficiency: cathode efficiency" improves) as the plating process is carried out under conditions that produce the "first current density" during a "deposition-dissolution process" where the ratio of the "third charge" to the "first charge" is large (i.e., a value produced by dividing the value of the "third charge" by the "first charge" is large) and the charge that contributes to deposition of metal onto the plated object decreases (i.e., the "current efficiency: cathode efficiency" worsens) as the plating process is carried out under conditions that produce the "first current density" during a "deposition-dissolution process" where the ratio of the "third charge" to the "first charge" is small (i.e., a value produced by dividing the value of the "third charge" by the "first charge" is small). Accordingly, based on the analysis results (analysis result data D1) of the "process Fa", during a plating process that uses the electroplating solution Xa to be analyzed, it is possible to specify the "current density" that enables a desired amount of metal to be deposited on the plated object with the desired "current efficiency: cathode efficiency".

In addition, as the "process Ga", a process that analyzes the state of the relationship between the current density in the plating process that uses the electroplating solution Xa to be analyzed and the dissolution rate by which the plated object dissolves due to an oxidation reaction during the plating process is executed based on the sets of measurement value data D0 acquired by the "measurement value acquiring process".

Here, when a voltage is applied between the plated object (cathode) and the electrode (anode) to produce a set current density during the plating process, in addition to metal and impurities in the electroplating solution being deposited on the plated object due to a reduction reaction, the plated object also dissolves due to an oxidation reaction (dissolution of the plated object into the electroplating solution). The ratio between the charge that contributes to the reduction reaction and the charge that contributes to the oxidation reaction out of the charge applied to the electroplating solution during the plating process also differs according to the voltage value of the voltage applied between the plated object and the electrode. Accordingly, when the current density during the plating process is set in view only of the reduction reaction, there is the risk of the dissolved amount of the plated object exceeding a tolerated range, which would result in defective products being manufactured. For this reason, to set favorable manufacturing conditions, it is preferable to specify the relationship between the current density during the plating process and the rate of dissolution of the plated object in advance.

In this "process Ga", the state of the electroplating solution Xa is analyzed using both the measurement value data D0 acquired by the "measurement value acquiring process 1a" that uses the working electrode 12 with an electrode surface formed of platinum that is highly insoluble in the electroplating solution Xa and the measurement value data D0a acquired by the "measurement value acquiring process 2a" that uses the working electrode 12a with an electrode surface formed of copper in the same way as the plated object.

More specifically, first, the "first current density" is calculated for each "deposition-dissolution process" based on the electrode area of the working electrodes 12 and 12a and the current value of the "first current". Also, based on the current value of the "second current" during the "measurement value acquiring process 1a" (a current value specified based on the measurement value data D0) and the "second period" for which the "second current" flowed, the "fourth charge" that is applied to the electroplating solution Xa in the "process 2A" during the "measurement value acquiring process 1a" is calculated for each "deposition-dissolution process". Also, based on the current value of the "second current" during the "measurement value acquiring process 2a" (a current value specified based on the measurement value data D0a) and the state of change of such current value in the "second period", the "fifth charge" that contributes to dissolution of metal in the "process 2A" during the "measurement value acquiring process 2a" is calculated for each "deposition-dissolution process". In addition, for each "deposition-dissolution process" where the voltage value of the "first voltage" applied during the "process 1A" is equal, the "sixth charge" that is the difference between the "fourth charge" and the "fifth charge" is calculated.

Figure 9:
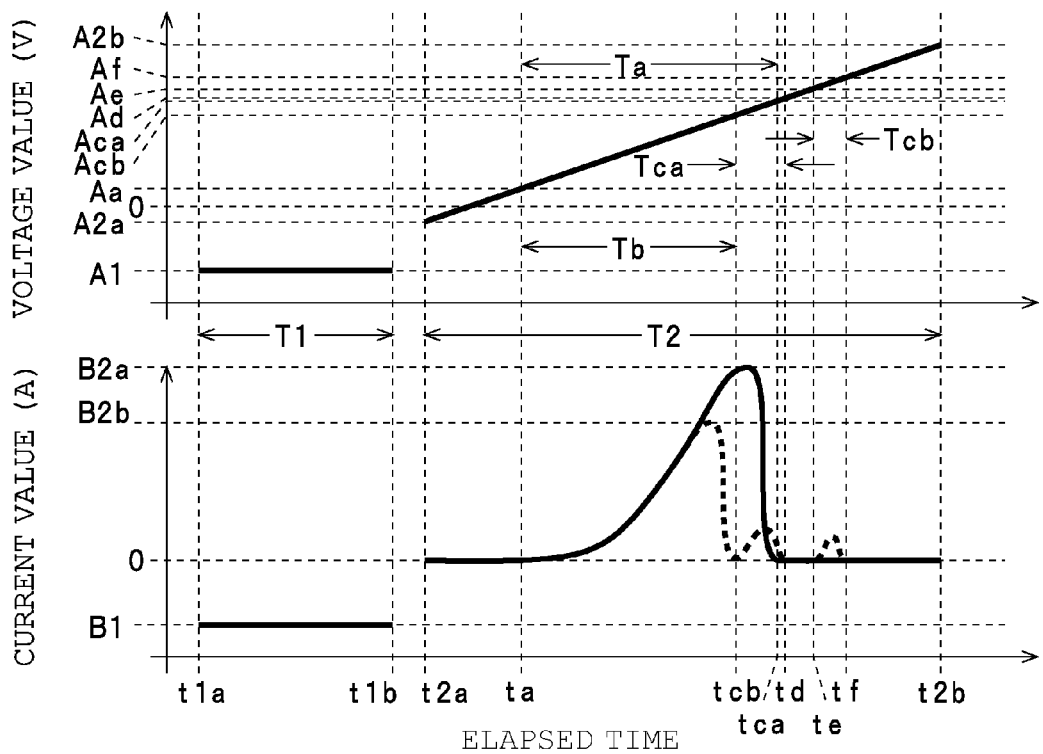
FIG. 9 is a diagram useful in explaining the relationship between the voltage value of the voltage applied between the reference electrode and the working electrode 12 in the measurement value acquiring processes 1$a$ and 1$b$ and the current value of the current flowing between the counter electrode and the working electrode 12, and also the relationship between the voltage value of the voltage applied between the reference electrode and the working electrode 12$a$ in the measurement value acquiring processes 2$a$ and 2$b$ and the current value of the current flowing between the counter electrode and the working electrode 12$a$.

More specifically, as one example, in the example of the "deposition-dissolution process" shown in FIG. 9, for the current values measured during the "process 2A", measurement values of the "measurement value acquiring process 1a" that uses the working electrode 12 are shown by the solid line and measurement values of the "measurement value acquiring process 2a" that uses the working electrode 12a are shown by the broken line. Here, since an oxidation reaction does not occur at the electrode surface during the "process 1A" of the "measurement value acquiring process 1a" that uses the working electrode 12 whose electrode surface is formed of platinum that is highly insoluble in the electroplating solution Xa, most of the "first charge" applied to the electroplating solution Xa contributes to deposition of metal and the like (the reduction reaction) and to electrolysis of the water included in the electroplating solution Xa. Since a large amount of metal is deposited on the electrode surface of the working electrode 12 as a result, during the "process 2A", the period Ta from time ta to time tca is required to dissolve such metal into the electroplating solution Xa.

On the other hand, during the "process 1A" of the "measurement value acquiring process 2a" that uses the working electrode 12a whose electrode surface is formed of copper in the same way as the plated object, since an oxidation reaction occurs at the electrode surface, the "first charge" applied to the electroplating solution Xa contributes not only to the deposition of metal (reduction reaction) and the like and to electrolysis of the water included in the electroplating solution Xa but also to dissolution of the copper of the working electrode 12a (i.e., dissolution into the electroplating solution Xa). For this reason, when a voltage with the voltage value A1 is applied between the reference electrode 11 and the working electrode 12a for the period T1 from time t1a to time t1b which is the same as the "process 1A" where the working electrode 12 is used, the amount of metal deposited onto the electrode surface of the working electrode 12a is smaller than the amount of metal deposited onto the surface of the working electrode 12 during the "measurement value acquiring process 1a".

Also, during the "process 2A" of the "measurement value acquiring process 2a" that uses the working electrode 12a, after the metal deposited onto the electrode surface of the working electrode 12a has been dissolved into the electroplating solution Xa (a state where the electrode surface of the working electrode 12a has become exposed), the electrode surface itself of the working electrode 12a is dissolved into the electroplating solution Xa due to an oxidation reaction at the electrode surface. As one example, in the example shown in FIG. 9, when a voltage whose voltage value changes at a rate of change of 10 mV/s during the period T2 from time t2a to time t2b is applied between both electrodes 11 and 12a, the metal (in the present embodiment, nickel) deposited on the electrode surface of the working electrode 12a by the "process 1A" starts to be dissolved into the electroplating solution Xa from time to when the voltage between both electrodes 11 and 12a reaches the voltage value Aa and becomes almost completely dissolved in the electroplating solution Xa at time tcb where the voltage value reaches Acb (a state where the electrode surface of the working electrode 12a is exposed).

For this reason, the copper that constructs the electrode surface of the working electrode 12a starts to be dissolved into the electroplating solution Xa, and for the period Tca until the time td where the voltage between both electrodes 11 and 12a reaches the voltage value Ad, dissolution of the copper constructing the electrode surface into the electroplating solution Xa continues. In addition, at the time to where the voltage between both electrodes 11 and 12 reaches the voltage value Ae, the copper that constructs the electrode surface of the working electrode 12a again starts to be dissolved into the electroplating solution Xa and for the period Tcb until the time tf where the voltage between both electrodes 11 and 12a reaches the voltage value Af, dissolution of the copper constructing the electrode surface into the electroplating solution Xa continues. Here, as in the illustrated example, the voltage value at which the metal (nickel) is dissolved into the electroplating solution Xa during the "process 2A" and the voltage value at which the copper constructing the electrode surface of the working electrode 12a is dissolved into the electroplating solution Xa differ. This means that based on the state of change in the current value (a current value sampled at 10 ms intervals) of the current that flowed between both electrodes 13 and 12 from time ta to time tf during the "process 2A", it is possible to specify the period for which a current flowed between both electrodes 13 and 12a due to the dissolution of metal and the period for which a current flowed between both electrodes 13 and 12a due to the dissolution of copper.

Accordingly, in the illustrated example, based on the integrated value of the current value (the current value of a current flowing between both electrodes 13 and 12a due to the dissolution of metal) that changes from the current value 0 to the current value B2 during the period Tb from time ta to time tcb and the period Tb for which a current flowed between both electrodes 13 and 12a, the charge (fifth charge) that contributes to the "deposition of metal") out of the charge applied to the electroplating solution Xa during the "process 2A" is calculated. The processing that calculates the "fifth charge" is executed for each "process 2A" in each "measurement value acquiring process 2a". Note that since the processing that calculates the "fourth charge" is the same as the calculation process of the "first charge" in the "process Ba" described earlier, detailed description thereof is omitted here. Next, the "sixth charge" that is the difference between the "fourth charge" and the "fifth charge" is calculated for each of the fifteen iterations of the "deposition-dissolution process".

After this, the state of the electroplating solution Xa is analyzed based on the calculated values of the "first current density" and the "sixth charge". More specifically, the analysis concludes that the electroplating solution Xa is in a state where the rate of dissolution (dissolution efficiency) per unit time of the plated object falls as the plating process is carried out under conditions that produce a "first current density" for which the "sixth charge" is small and the rate of dissolution (dissolution efficiency) per unit time of the plated object rises as the plating process is carried out under conditions that produce a "first current density" for which the "sixth charge" is large. Accordingly, based on the analysis results (analysis result data D1) of the "process Ga", it is possible to specify a "current density" capable of depositing metal on the plated object without causing excessive dissolution of the plated object during a plating process that uses the electroplating solution Xa to be analyzed.

After the "processes Aa to Ga" have been sequentially executed, the processing unit 33 generates the analysis result data D1 in which the analysis results are recorded, stores the analysis result data D1 in the storage unit 34, and displays graphs and analysis values showing the analysis results on the display unit 32. By doing so, the "analysis process" is completed. After this, the user refers to the analysis results displayed on the display unit 32 and arbitrarily sets the processing conditions for a plating process that uses the electroplating solution Xa that has been analyzed. By doing so, it is possible to execute the plating process under favorable conditions for the state of the electroplating solution Xa, and as a result, it is possible to manufacture favorable products (plated products).

Note that although an example has been described where the series of processes (the "measurement value acquiring process" and the "analysis process") described above are executed to set the processing conditions of a plating process that uses the electroplating solution Xa to be analyzed, as one example, it is also possible to set the processing conditions of the plating process by executing the processes described above when new electroplating solution Xa (i.e., unused electroplating solution Xa) has been introduced into the plating solution tank X, to store the analysis result data D1 stored in the storage unit 34 at such time as "reference values", and to specify changes in the state of the electroplating solution Xa by comparing analysis result data D1 obtained by executing the same processes (the "measurement value acquiring process" and the "analysis process") as the processes described above at arbitrary timing (for example, when the plating process has been carried out for a number of iterations set in advance) with the analysis result data D1 as the "reference values". By doing so, it is possible, when the electroplating solution Xa held in the plating solution tank X has deteriorated to a state where it is difficult to execute a desired plating process, to change the processing conditions of the plating process and/or specify a replacement schedule for the electroplating solution Xa, without having defects manufactured.

In this way, according to the electroplating solution analyzing system 1 and the electroplating solution analyzing method used by such system, when analyzing the state of the electroplating solution Xa by executing the "measurement value acquiring process" that executes a measurement process that measures the current value of the current flowing between the counter electrode 13 and the working electrode 12 (12*a*) while applying a voltage between the reference electrode 11 and the working electrode 12 (12*a*) to acquire measurement values (the measurement value data D0 and D0*a*) and the "analysis process" that analyzes the state of the electroplating solution Xa based on the acquired measurement values, the "deposition-dissolution process", in which the "process 1A" that measures the current value of the "first current" flowing between both electrodes 13 and 12 (12*a*) as a measurement value while applying the "first voltage" to both electrodes 11 and 12 (12*a*) for the "first period" to deposit metal on the working electrode 12 (12*a*) and the "process 2A" that measures, with a cycle set in advance, the current value of the "second current" that flows between both electrodes 13 and 12 (12*a*) as measurement values while causing metal that was deposited on the working electrode 12 (12*a*) during the "process 1A" to be dissolved into the electroplating solution Xa by applying the "second voltage" whose voltage value changes with a rate of change set in advance to both electrodes 11 and 12 (12*a*) during the "second period", are executed in that order is executed a plurality of times while changing the voltage value of the "first voltage" in a voltage value range set so as to produce a current density in a current density range set in advance.

In this way, according to the electroplating solution analyzing system 1 and the electroplating solution analyzing method used by such system, unlike a convention analysis method that analyzes the state of electroplating solution by executing a deposition process a plurality of times with different voltage values of the voltage applied between the sample and the electrode and measures the deposited state of metal on each sample, it is possible, in the same way as when fabricating a plurality of samples while changing the voltage value of the voltage applied when depositing metal, to acquire measurement values in keeping with the deposited state of metal in each deposition process and analyze the state of the electroplating solution Xa. When doing so, by dissolving the metal deposited on the working electrode 12 (12*a*) during the "process 1A" in the electroplating solution Xa during the "process 2A" of each "deposition-dissolution process", it is possible to produce a state where metal is not deposited on the working electrode 12 (12*a*) by the time the next "deposition-dissolution process" starts, which means that it is possible to continuously execute the "deposition-dissolution process" a plurality of times without replacing the working electrode 12 (12*a*) numerous times and/or removing metal deposited on the working electrode 12 (12*a*). By doing so, it is possible, compared to the conventional analysis method where it is necessary to provide a plurality of samples and to execute the deposition process and the measurement process a plurality of times, to analyze the state of the electroplating solution Xa easily and at low cost.

Also, according to the electroplating solution analyzing system 1 and the electroplating solution analyzing method used by such system, at least one process out of:

the process Aa that concludes, based on the "second charge" and the ""first current density" calculated based on the measurement values (the measurement value data D0) acquired in the "measurement value acquiring process", that the electroplating solution Xa is in a state where the amount of metal deposited per unit time on the plated object increases as the plating process is carried out under conditions that produce the "first current density" during a "deposition-dissolution process" that has a large "second charge" and where the amount of metal deposited per unit time on the plated object decreases as the plating process is carried out under conditions that produce the "first current density" during a "deposition-dissolution process" that has a small "second charge";

the process Ba that concludes, based on the "first charge", the "second charge", and the "first current density" calculated based on the measurement values acquired in the "measurement value acquiring process", that the electroplating solution Xa is in a state where the charge that does not contribute to the deposition of metal on the plated object decreases as the plating process is carried out under conditions that produce the "first current density" during a "deposition-dissolution process" where the "difference in charge" was small, and where the charge that does not contribute to the deposition of metal on the plated object increases as the plating process is carried out under conditions that produce the "first current density" during a "deposition-dissolution process" where the "difference in charge" was large;

the process Ca that specifies, based on the "amount of metal" and the "first current density" calculated based on the measurement values acquired in the "measurement value acquiring process", a "current density lower limit value" for the "first current density" that is capable of depositing at least an amount of metal set in advance onto the working electrode 12, and concludes that the electroplating solution Xa is in a state where it is not possible to deposit at least the amount of metal set in advance on the plated object when the plating process is carried out under conditions that produce a "first current density" that falls below the "current density lower limit value";

the process Da that specifies, based on the "amount of metal" and the "first current density" calculated based on the measurement values acquired in the "measurement value acquiring process", a "current density upper limit value" for the "first current density" that is capable of depositing at least an amount of metal set in advance onto the working electrode 12, and concludes that the electroplating solution Xa is in a state where it is not possible to deposit at least the amount of metal set in advance on the plated object when the plating process is carried out under conditions where the "first current density" exceeds the "current density upper limit value";

the process Ea that concludes, based on the current value of the "second current" in each "deposition-dissolution process", that the electroplating solution Xa is in a state where impurities are included in the electroplating solution Xa when the current value of the "second current" is at least equal to a reference current value set in advance; and the process Fa that concludes, based on the "first current density", the "first charge", and the "third charge" acquired in the "measurement value acquiring process", that the electroplating solution Xa is in a state where the charge that contributes to the deposition of metal on the plated object increases as the plating process is carried out under conditions that produce the "first current density" during a "deposition-dissolution process" where the ratio of the "third charge" to the "first charge" is large, and where the charge that contributes to the deposition of metal on the plated object decreases as the plating process is carried out under conditions that produce the "first current density" during a "deposition-dissolution process" where the ratio of the "third charge" to the "first charge" is small, is executed as the "analysis process".

Accordingly, according to the electroplating solution analyzing system 1 and the electroplating solution analyzing method used by such system, unlike the conventional analysis method that fabricates a plurality of samples with different conditions (carries out a plating process) and measures the amount of metal or the like deposited on the respective materials, it is possible, by executing a process (any of the processes Aa to Fa) in keeping with the desired factors to be analyzed, to accurately and easily analyze the state of the electroplating solution Xa, even for a user unused to analyzing electroplating solution.

In addition, according to the electroplating solution analyzing system 1 and the electroplating solution analyzing method used by such system, the "process Ga" that executes:

the "measurement value acquiring process 1*a*" that uses the working electrode 12 whose electrode surface is formed of a "first material (in the present embodiment, platinum)" with at least a preset level of insolubility in the electroplating solution Xa; and the "measurement value acquiring process 2*a*" that uses the working electrode 12*a* whose electrode surface has the same area as the electrode surface of the working electrode 12 and whose electrode surface is formed by a "second material (in the present embodiment, copper) that is the same as the plated object on which metal is to be deposited by a plating process and sets the "first period" and the voltage value of the "first voltage" during the "process 1A" and the "second period", and the voltage value and rate of change of the voltage value of the "second voltage" during the "process 2A" at the same values as during the "measurement value acquiring process 1*a*", as the "measurement value acquiring process", and concludes, based on the "first current density" and the "sixth charge", that the electroplating solution Xa is in a state where the rate of dissolution per unit time of the plated object falls as the plating process is carried out under conditions that produce a "first current density" for which the "sixth charge" is small and the rate of dissolution per unit time of the plated object rises as the plating process is carried out under conditions that produce a "first current density" for which the "sixth charge" is large, as the "analysis process".

Accordingly, according to the electroplating solution analyzing system 1 and the electroplating solution analyzing method used by such system, it is possible to easily and accurately analyze the extent to which the electroplating solution Xa to be analyzed will dissolve the plated object due to an oxidation reaction during the plating process.

Second Embodiment

Next, another embodiment of an electroplating solution analyzing apparatus will be described with reference to the attached drawings. Note that the component elements in the electroplating solution analyzing system 1 used in the second embodiment that are the same as in the electroplating solution analyzing system 1 used in the first embodiment described earlier have been assigned the same reference numerals and duplicated description thereof is omitted.

When monitoring the state of the electroplating solution Xa using the electroplating solution analyzing system 1, as one example, the series of analysis processes described below are executed after new electroplating solution Xa has been introduced into the plating solution tank X to set the processing conditions when executing the electroplating process using an electroplating solution Xa and to acquire "reference values" for grasping a state of changes in the electroplating solution Xa.

More specifically, first, the electrochemical measuring apparatus 2 is transported to the installed location of the plating solution tank X into which the new electroplating solution Xa has been introduced and the electrochemical sensor 2*a* is assembled. Here, as one example, when the "measurement value acquiring process" is executed in the order of the "measurement value acquiring process 1*b*" then the "measurement value acquiring process 2*b*", the working electrode 12 is attached to the working electrode 12. By doing so, the electrodes 11, 12, and 13 are attached to the casing 10 and become connected to the signal processing circuit board 14 inside the casing 10. After this, by connecting the electrochemical sensor 2*a* to the measuring apparatus body 2*b* via the signal cable 2*c*, the preparation for an electrochemical measurement process carried out by the electrochemical measuring apparatus 2 to start is completed. Note that it is assumed that a setting operation for conditions (measurement conditions) of the respective measurement processes described below has already been completed.

Next, as shown in FIG. 1, after the electrodes 11, 12, and 13 of the electrochemical sensor 2*a* have been immersed in the electroplating solution Xa so that the electrode surfaces are in contact with the electroplating solution Xa, a measurement start switch of the measuring apparatus body 2*b* is operated to start the "measurement value acquiring process 1*b*" as the "measurement value acquiring process". Here, in the electroplating solution analyzing system 1 (the electrochemical measuring apparatus 2), when the start of processing has been indicated, the processing unit 23 starts the "deposition-dissolution process" that executes a "process 1B (a process that obtains measurement values while depositing metal onto the working electrode 12: deposition process)" and a "process 2B (a process that obtains measurement values while dissolving the metal deposited on the working electrode 12 into the electroplating solution: dissolution process)" in that order as the "measurement value acquiring process". Note that in the "measurement value acquiring process" that has one object of setting the processing conditions of an electroplating process, during the "process 1B" described above the "deposition-dissolution process" is carried out a plurality of times while changing the voltage value of the voltage applied between both electrodes 11 and 12.

More specifically, as shown in FIG. 2, as the "process 1B" described above, the processing unit 23 applies a voltage (the potential of the working electrode 12 with respect to the reference electrode 11: one example of a "first voltage") with a voltage value A1 set in advance between the reference electrode 11 and the working electrode 12 for a period T1 (one example of a "first period": for example, 60 s) set in advance so as to deposit metal on the electrode surface of the working electrode 12 and measures a current value B1 of a current (one example of a "first current") that flows between the counter electrode 13 and the working electrode 12 with a cycle set in advance (the same cycle as the cycle for measuring current values during the "process 2B" described later: as one example, intervals of 10 ms).

In this case, during the "process 1B", since a fixed voltage (a voltage with the voltage value A1) is applied between the reference electrode 11 and the working electrode 12, as shown in the drawing, the measured current value B1 will be a constant value for the period T1 from time t1$a$ to time t1$b$. Accordingly, for the "process 1B", instead of measuring the current value with a cycle set in advance, it is possible to use a configuration that measures the current value B1 only once during the period T1 (i.e., from time t1$a$ to time t1$b$) where a voltage with the voltage value A1 is applied between the reference electrode 11 and the working electrode 12.

Also, as the "process 2B" mentioned above, the processing unit 23 applies a voltage (the potential of the working electrode 12 relative to the reference electrode 11: in the illustrated example, a voltage whose voltage value changes in a range of the voltage values A2$a$ to A2$b$: one example of a "second voltage") whose voltage value changes with a rate of change (as one example, 10 mV/s) set in advance for a period T2 (one example of the "second period") set in advance between the reference electrode 11 and the working electrode 12 and measures the current value (in the illustrated example, a current value that changes in a range of the current values 0 to B2) of the current (one example of the "second current") flowing between the counter electrode 13 and the working electrode 12 with a cycle set in advance (as one example, 10 ms intervals) while dissolving the metal that was deposited onto the working electrode 12 during the "process 1B" described above into the electroplating solution Xa.

In this case, as described earlier, in the "measurement value acquiring process" that has one object of setting the processing conditions of the electroplating process, every time a "deposition-dissolution process" such as that described above is executed, the voltage value A1 of the voltage applied to both electrodes 11 and 12 during the "process 1B" is changed in steps of 0.2V. More specifically, as one example, when analyzing an electroplating solution for nickel plating as the electroplating solution Xa to be analyzed, fifteen iterations of the "deposition-dissolution process" are sequentially executed while changing the voltage value A1 of the voltage applied to both electrodes 11 and 12 during the "process 1B" in steps of 0.2V in a range of −3.4V to 0.6V for example. Note that the change in the voltage value during each "process 1B", the minimum value (in the example described above, −3.4V) and the maximum value (in the example described above, −0.6V) of the voltage applied during the "process 1B" are not limited to the examples described above and it is possible to set such values at arbitrary values in a voltage value range such that the current density at the working electrode 12 is in a current density range set in advance.

In this case, the area that contacts the electroplating solution differs between the working electrode 12 on which metal is deposited during analysis by the electroplating solution analyzing system 1 and the part (product) where a metal film is formed during the manufacturing of products. This means that the amount of metal deposited per unit time when a voltage with the same voltage value is applied will differ between the "process 1B (deposition process)" carried out by the electroplating solution analyzing system 1 (the electrochemical measuring apparatus 2) and the electroplating process during the manufacturing of products. Accordingly, when specifying favorable manufacturing conditions (the voltage value of the voltage to be applied, and the like) using the electroplating solution analyzing system 1 (the electrochemical measuring apparatus 2), by executing the "analysis process" described later, the current density during the electroplating process that is capable of depositing the required amount of metal per unit time on the working electrode 12 is calculated and the voltage value of the voltage to be applied to the product (cathode) and the anode during the electroplating process and the like are calculated based on the calculated current density and the area of the product on which metal is to be deposited.

On the other hand, when carrying out the analysis process for the first time on the electroplating solution Xa, the range of the current density described above (the voltage value range of the voltage value to be applied) capable of depositing the required amount of metal per unit time is yet to be specified. For this reason, as the minimum value of the voltage value of the voltage to be applied during the "process 1B" described above, as one example a voltage value that produces a current density that is sufficiently lower than the lower limit value, which is assumed to be a current density capable of depositing metal on the plated object, during an actual plating process that uses the electroplating solution Xa is set in keeping with the type of electroplating solution Xa, and as the maximum value of the voltage to be applied, a voltage value that produces a current density that is sufficiently higher than the upper limit value assumed as the current density capable of depositing metal on the plated object during an actual plating process that uses the electroplating solution Xa is set. As a result, in the present embodiment, the voltage value A1 of the voltage applied between both electrodes 11 and 12 during each "process 1B" is set in a voltage value range so as to increase in steps of 0.2V in a range of −3.4V to −0.6V.

With the electroplating solution analyzing system 1 (electrochemical measuring apparatus 2) according to the present embodiment, each "deposition-dissolution process" is executed so that the voltage value range (voltage values A2$a$ to A2$b$ in FIG. 2) of the voltage applied between the reference electrode 11 and the working electrode 12 during the "process 2B" and the rate of change are the same voltage value range and rate of change. More specifically, as one example, when analyzing an electroplating solution for nickel plating as the electroplating solution Xa to be analyzed, in each "deposition-dissolution process", the voltage values A2$a$ to A2$b$ of the voltage applied between the reference electrode 11 and the working electrode 12 during the "process 2B" are changed at a rate of change of 10 mV/s in a range of −0.5 to 1.0V, for example.

Note that the minimum value (in the above example, −0.5V) and the maximum value (in the above example, 1.0V) and the rate of change (in the above example, 10 mV/s) of the voltage applied between both electrodes 11 and 12 during the "process 2B" are not limited to the example described above. In this case, the voltage value range of the voltage applied during the "process 2B" is set so that the current density of the working electrode 12 is within a current density range that is set in advance. More specifically, for the minimum value of the applied voltage (the lower limit value of the voltage value range), a voltage value that produces a current density that is sufficiently lower than the lower limit value of the current density that dissolves metal that has been deposited on the working electrode 12 by the "process 1B" into the electroplating solution Xa and also does not deposit metal (in the present embodiment, nickel) onto the working electrode 12 is set in accordance with the type of electroplating solution Xa, and for the maximum value of the applied voltage (the upper limit value of the voltage value range), a voltage value that produces a current density that is sufficiently higher than the upper limit value of the current density that dissolves metal that was deposited on the working electrode 12 by the "process 1B" into the electroplating solution Xa is set. As a result, in the present embodiment, the voltage value and rate of change of the voltage applied to both electrodes 11 and 12 in each "process 2B" are set in a range of −0.5V to 1.0V with a rate of change of 10 mV/s.

In this case, during the "process 2B" executed after metal has been deposited on the working electrode 12 by the "process 1B", the metal that was deposited on the working electrode 12 is dissolved back into the electroplating solution Xa by applying a voltage in the voltage value range described above between both electrodes 11 and 12 and when doing so, the current value of the current flowing between both electrodes 13 and 12 changes in accordance with the voltage value of the voltage applied between both electrodes 11 and 12. More specifically, in the example in FIG. 2 where metal is deposited on the working electrode 12 by applying a voltage with the voltage value A1 between both electrodes 11 and 12 for the period T1 from time t1$a$ to time t1$b$ during the "process 1B", when a voltage whose voltage value changes with a rate of change of 10 mV/s between both electrodes 11 and 12 for the period T2 from time t2$a$ to time t2$b$ during the "process 2B", a current flows between both electrodes 11 and 12 for the period T (one example of a "second period") from times ta to tc due to the metal deposited on the working electrode 12 being dissolved into the electroplating solution Xa.

Also, in the example shown in FIG. 2, when a voltage in a voltage value range from the voltage value A2$a$ applied between both electrodes 11 and 12 at time t2$a$ to the voltage value Aa applied between both electrodes 11 and 12 at time ta is applied between both electrodes 11 and 12, a current does not flow between both electrodes 12 and 13. That is, with the electroplating solution Xa in the illustrated example, when a voltage in the voltage value range of the voltage values A2$a$ to Aa is applied between both electrodes 11 and 12, a state is produced where there is no deposition of metal onto the working electrode 12 and no dissolution of deposited metal into the electroplating solution Xa.

In addition, in the example shown in FIG. 2, the current value B2 of the current flowing between both electrodes 13 and 12 when a voltage with the voltage value Ab is applied between both electrodes 11 and 12 at the time tb reaches a maximum value, and when a voltage in the voltage value range from the voltage value Ac applied between both electrodes 11 and 12 at time tc to the voltage value A2$b$ applied between both electrodes 11 and 12 at time t2$b$ is applied between both electrodes 11 and 12, a current does not flow between both electrodes 12 and 13. That is, if the "process 1B" described above was executed using the electroplating solution Xa in the illustrated example, the metal deposited on the working electrode 12 is dissolved with the highest efficiency into the electroplating solution Xa when a voltage with the voltage value Ab is applied between both electrodes 11 and 12, all of the metal deposited on the working electrode 12 during the "process 1B" will have been dissolved into the electroplating solution Xa (a state where the electrode surface of the working electrode 12 is in direct contact with the electroplating solution Xa) at the time tc when a voltage with the voltage value Ac is applied between both electrodes 11 and 12, and after this, when a voltage in the voltage value range of the voltage values Ac to A2$b$ is then applied between both electrodes 11 and 12, a state is produced where metal to be dissolved into the electroplating solution Xa is no longer present.

This means that by applying a voltage with the voltage value of at least the voltage value Ab to both electrodes 11 and 12 during the "process 2B" for a period that is sufficiently longer than the period from time tb to time tc, the "deposition-dissolution process" ends at the time t2$b$ in a state where metal has not been deposited on the working electrode 12. Accordingly, when the "deposition-dissolution process" is repeatedly executed a plurality of times, by applying, during the "process 2B" in each "deposition-dissolution process", a voltage in a sufficiently wide voltage value range from the voltage value A2$a$ that is sufficiently lower than the voltage value Aa described above and where metal is not deposited on the working electrode 12 to the voltage value A2$b$ that is sufficiently higher than the voltage value Ab described above to both electrodes 11 and 12, it is possible, when executing a "deposition-dissolution process" that is follows the present "deposition-dissolution process", to start the "process 1B" in a state where metal has not been deposited onto the working electrode 12. By doing so, it is possible to repeatedly execute the "deposition-dissolution process" a plurality of times without carrying out a task of removing metal from the working electrode 12 whenever the "deposition-dissolution process" is carried out or a task of replacing the working electrode 12 whenever the "deposition-dissolution process" is carried out.

For this reason, when executing the measurement value acquiring process that has an object of setting the processing conditions of the electroplating process and acquiring reference values, as one example, as the processing of the first of fifteen iterations of the "deposition-dissolution process", the "process 1B" that measures the current value B1 of the current flowing between the counter electrode 13 and the working electrode 12 while applying a voltage with the voltage value A1=−3.4V between the reference electrode 11 and the working electrode 12 for the period T1 from time t1$a$ to time t1$b$ and the "process 2B" that measures the current value of the current flowing between the counter electrode 13 and the working electrode 12 while applying a voltage whose voltage value gradually increases at a rate of change of 10 mV/s within a range of −0.5V to 1.0V between the reference electrode 11 and the working electrode 12 for the period T2 from time t2$a$ to t2$b$ are executed in that order.

During the "process 2B" of the first iteration of the "deposition-dissolution process", as one example, current values shown by the graph G01 in FIG. 3 (in this example, a current value that hardly changes in the period T2) are measured. Accordingly, the processing unit 23 records the current value measured during the "process 1B" as part of the measurement value data D0 for the first iteration of the "deposition-dissolution process" in association with the voltage value A1=−3.4V of the voltage applied between both electrodes 11 and 12 and records a current value measured in a cycle set in advance (in the present embodiment, at 10 ms intervals) during the "process 2B" as another part of the measurement value data D0 for the first "deposition-dissolution process" in association with the voltage value of the voltage applied between both electrodes 11 and 12 when such measurements are made.

As the processing of the second iteration out of the fifteen iterations of the "deposition-dissolution process", the processing unit 23 executes the "process 1B" that measures the current value B1 of the current flowing between both electrodes 13 and 12 while applying a voltage where the voltage value A1=−3.2V between both electrodes 11 and 12 and the "process 2B" that measures the current value of the current flowing between both electrodes 13 and 12 while applying a voltage whose voltage value gradually increases in a range of −0.5V to 1.0V at a rate of change of 10 mV/s to both electrodes 11 and 12. At this time, during the "process 2B" of the second iteration of the "deposition-dissolution process", current values shown by the graph G02 are measured. Accordingly, the processing unit 23 records a current value measured during the "process 1B" as part of the measurement value data D0 for the second iteration of the "deposition-dissolution process" in association with the voltage value A1=−3.2V of the voltage applied between both electrodes 11 and 12 and records current values measured with a cycle set in advance during the "process 2B" as another part of the measurement value data D0 for the first "deposition-dissolution process" in association with the voltage value of the voltage applied between both electrodes 11 and 12 when such measurements are made.

After this, in the third and subsequent iterations of the "deposition-dissolution process", the voltage value of the voltage applied between both electrodes 11 and 12 during the "process 1B" is increased in steps of 0.2V in the manner of −3.0V, −2.8V, . . . and the current values shown in the graphs G03, G04, . . . are measured during the "process 2B". By doing so, when the fifteenth iteration of the "deposition-dissolution process" has been completed, a total of fifteen sets of measurement value data D0 for the fifteen iterations of the "deposition-dissolution processes" from the first to the fifteen iterations will have been stored in the storage unit 24. By doing so, the "measurement value acquiring process 1b" is completed.

Next, the "measurement value acquiring process 2b" is executed. More specifically, the electrochemical sensor 2a is pulled out from the plating solution tank X and the working electrode 12a is attached to the casing 10 in place of the working electrode 12. Next, various conditions such as the "first period" and the "voltage value of the first voltage" during the "process 1B" and the "second period", the "voltage value of the second voltage", and the "rate of change of the voltage value of the second voltage" during the "process 2B" as set in the same way as during the "measurement value acquiring process 1b", and fifteen iterations of the "deposition-dissolution process" are executed with the same procedure as during the "measurement value acquiring process 1b". By doing so, the "measurement value acquiring process 2b" is completed in a state where fifteen sets of measurement value data D0 are stored in the storage unit 24.

Note that in the following description, to distinguish between the sets of measurement value data D0 acquired by the "measurement value acquiring process 1b" that uses the working electrode 12 and the sets of measurement value data D0 acquired by the "measurement value acquiring process 2b" that uses the working electrode 12a, sets of measurement value data D0 acquired by the "measurement value acquiring process 2b" are referred to as the measurement value data D0a. By carrying out the above processing, all of the processing to be executed by the electrochemical measuring apparatus 2 is completed. Note that in the processing executed at the electrochemical measuring apparatus 2, in place of the example described above, it is also possible to execute the "measurement value acquiring process" in the order of the "measurement value acquiring process 2b" then the "measurement value acquiring process 1b".

Next, after the electrochemical sensor 2a has been pulled out from the plating solution tank X and the electrodes 11, 12a (12), and 13 have been removed from the casing 10 and housed in a case for storage purposes, the electrochemical measuring apparatus 2 is transported to the location where the analyzing apparatus 3 is installed and the measuring apparatus body 2b is connected to the analyzing apparatus 3 via a signal cable 4 (see FIG. 1). Note that as described later, when analysis of the state of changes in the electroplating solution Xa is carried out frequently, it is possible to leave the electrochemical sensor 2a installed on the plating solution tank X and separate the signal cable 2c from the measuring apparatus body 2b and transport only the measuring apparatus body 2b to the installed location of the analyzing apparatus 3 and connect the apparatuses 2 and 3 to one another, or to leave the measuring apparatus body 2b connected via the signal cable 2c to the electrochemical sensor 2a that is installed on the plating solution tank X and transport the analyzing apparatus 3 to the installed location of the plating solution tank X (the installed location of the electrochemical measuring apparatus 2) and connect the apparatuses 2 and 3 to one another.

After this, by operating the operation unit 21 of the electrochemical measuring apparatus 2 (the measuring apparatus body 2b), the measurement value data D0 and D0a stored in the storage unit 24 are transmitted to the analyzing apparatus 3. In accordance with this, at the analyzing apparatus 3, the processing unit 33 stores the measurement value data D0 and D0a transmitted from the electrochemical measuring apparatus 2 in the storage unit 34. Note that the transmission of the measurement value data D0 and D0a from the electrochemical measuring apparatus 2 to the analyzing apparatus 3 is not limited to the above example of operating the operation unit 21 of the electrochemical measuring apparatus 2 and it is also possible to have the measurement value data D0 and D0a transmitted from the electrochemical measuring apparatus 2 to the analyzing apparatus 3 by operating the operation unit 31 of the analyzing apparatus 3 to transmit a transmission request signal from the analyzing apparatus 3 to the electrochemical measuring apparatus 2. By doing so, a state where the measurement value data D0 and D0a necessary for analyzing the electroplating solution Xa are stored in the storage unit 34 of the analyzing apparatus 3 is produced and the "measurement value acquiring process" is completed.

Next, the "analysis process" is executed at the analyzing apparatus 3. Here, in the example described above where the "measurement value acquiring process" (the "measurement value acquiring process 1*b*" and the "measurement value acquiring process 2*b*") are executed with one object of setting the processing conditions of the electroplating process, when executing the "deposition-dissolution process" for a plurality of iterations (in the present embodiment, fifteen iterations), during the "process 1B" in each "deposition-dissolution process", metal is deposited on the working electrode 12 (12*a*) while changing the voltage value of the voltage applied between the reference electrode 11 and the working electrode 12 (12*a*). This means that by obtaining the measurement value data D0 and D0*a* by executing the "deposition-dissolution process" for the fifteen iterations described above, it is possible, without fabricating samples of a plurality of types of electroplating processes where the voltage value of the voltage applied between the electrode and the sample is changed, to analyze the electroplating solution Xa based on the measurement value data D0 and D0*a* acquired by executing the "deposition-dissolution process" and set the processing conditions for an actual electroplating process.

More specifically, in the electroplating solution analyzing system 1 (analyzing apparatus 3) according to the present embodiment, the processing unit 33 executes an analysis process (a process that analyzes the state of the electroplating solution Xa) during the "process Ab" to the "process Gb" described later based on the measurement value data D0 and D0*a* of each "deposition-dissolution process", displays the analysis results on the display unit 32, generates the analysis result data D1 showing the analysis results, and stores the analysis result data D1 in the storage unit 34. Note that although it is possible to execute the analysis processes aside from the "process Eb" using only the measurement value data D0*a* acquired by the "measurement value acquiring process 2*b*" that uses the working electrode 12*a* or using both the measurement value data D0 and D0*a*, for ease of understanding the configuration of the "electroplating solution analyzing apparatus", an example will be described where the analysis processing during the "processes Ab to Db, Fb, Gb" is executed using only the measurement value data D0.

First, as the "process Ab", a process that analyzes the state of the relationship between the voltage (current density) applied between the plated object (cathode) and the electrode (anode) during the plating process that uses the electroplating solution Xa to be analyzed and the amount of metal deposited per unit time on the plated object is executed based on the sets of measurement value data D0 described above acquired by the "measurement value acquiring process".

In this case, the surface area of the plated object (for the actual plating process) on which metal (in the present embodiment, nickel) is to be deposited using the electroplating solution Xa to be analyzed differs to the electrode area of the working electrode 12 on which metal (in the present embodiment, nickel) is deposited in the measurement value acquiring process described above. Accordingly, in the electroplating solution analyzing system 1 according to the present embodiment, as described earlier, a configuration is used where in place of the voltage value of the voltage applied when depositing metal, the current density (cathode current density) corresponding to the voltage value of the applied voltage is calculated and the calculated current density and parameters of the factors to be analyzed are associated to produce the analysis results of the "analysis process".

More specifically, in the "process Ab", first, a process that calculates the "second charge" applied to the electroplating solution Xa during the "process 2B" based on the current value of the "second current" and the "second period" for which the "second current" flows between the counter electrode 13 and the working electrode 12 during the "process 2B", and a process that calculates the "first current density" based on the electrode area of the working electrode 12 and the current value of the "first current" are respectively executed in each "deposition-dissolution process" (for each set of measurement value data D0).

More specifically, as one example, for the example of the "deposition-dissolution process" shown in FIG. 2, the charge (second charge) applied to the electroplating solution Xa during the "process 2B" is calculated based on an integrated value (an integrated current value) for the current values (current values sampled at 10 ms intervals) that changed from the current value 0 to the current value B2 for the period T from time ta to time tc and the period T where a current flowed between both electrodes 13 and 12. Also, the current density (first current density) of the working electrode 12 is calculated based on the electrode area of the working electrode 12 and the integrated value (integrated current value) of the current value B1 (each current value B1 that is sampled at 10 ms intervals in the present embodiment) of the current that flows between both electrodes 13 and 12 in a state where a voltage is applied between both electrodes 11 and 12 for the period T1 from time t1*a* to t1*b*. This calculation process is individually executed for each set of measurement value data D0 of the fifteen iterations of the "deposition-dissolution process".

Next, the state of the electroplating solution Xa is analyzed based on the calculated values of the "second charge" and the "first current density". More specifically, the analysis concludes that the electroplating solution Xa to be analyzed is in a state where the amount of metal deposited per unit time on the plated object increases as the plating process is carried out under conditions that produce the "first current density" during a "deposition-dissolution process" that has a large "second charge" calculated based on the measurement value data D0, and where the amount of metal deposited per unit time on the plated object decreases as the plating process is carried out under conditions that produce the "first current density" during a "deposition-dissolution process" that has a small "second charge". Accordingly, based on the analysis results (the analysis result data D1) of the "process Aa", it is possible to specify the "current density" that is capable of depositing a desired amount of metal per unit time on the plated object during a plating process that uses the electroplating solution Xa to be analyzed.

Also, as the "process Bb", a process that analyzes the state of the relationship between the current density in a plating process that uses the electroplating solution Xa to be analyzed and the amount of charge that does not contribute to deposition of metal on the plated object out of the charge applied to the electroplating solution Xa (the analysis process that relates to "current efficiency: cathode efficiency") is executed based on the measurement value data D0 described above acquired by the "measurement value acquiring process".

More specifically, in the "process Bb", first, a process that calculates the "first charge" applied to the electroplating solution Xa during the "process 1B" based on the current value of the "first current" and the "first period", calculates the "second charge" based on the current value of the "second current" and the "second period", and calculates the difference between the "first charge" and the "second charge", and a process that calculates the "first current density" based on the electrode area of the working electrode 12 and the current value of the "first current" are respectively executed for each "deposition-dissolution process" (for each set of measurement value data D0).

More specifically, in the example of the "deposition-dissolution process" shown in FIG. 2, based on the integrated value of the current value B1 of the current flowing between both electrodes 13 and 12 in a state where a voltage is applied between both electrodes 11 and 12 for the period T1 from time t1a to t1b (in the present embodiment, current values B1 sampled at 10 ms intervals) and the period T1 for which a current flowed between both electrodes 13 and 12, the charge (first charge) applied to the electroplating solution Xa during the "process 1B" is calculated. Also, the charge (second charge) applied to the electroplating solution Xa during the "process 2B" is calculated based on the integrated value of the current value that changes from the current value 0 to the current value B2 during the period T from time ta to time tc (the current values sampled at 10 ms intervals) and the period T for which a current flowed between both electrodes 13 and 12. In addition, the difference between the "first charge" and the "second charge" described above is calculated. Also, the current density (first current density) at the working electrode 12 is calculated based on the electrode area of the working electrode 12 and the integrated value of the current value B1 (in the present embodiment, the current values B1 sampled at 10 ms interval) of the current that flows between both electrodes 13 and 12 in a state where a voltage is applied between both electrodes 11 and 12 during the period T1 from time t1a to time t1b. This calculation process is executed for each measurement value data D0 of the fifteen iterations of the "deposition-dissolution process".

Next, the state of the electroplating solution Xa is analyzed based on the calculated values of the "first charge", the "second charge" and the "first current density". More specifically, the analysis concludes that the electroplating solution Xa to be analyzed is in a state where the charge that does not contribute to the deposition of metal on the plated object decreases (i.e., the "current efficiency: cathode efficiency" improves) as the plating process is carried out under conditions that produce the "first current density" during a "deposition-dissolution process" where the "difference in charge" calculated based on the measurement value data D0 was small, and where the charge that does not contribute to the deposition of metal on the plated object increases (i.e., the "current efficiency: cathode efficiency" worsens) as the plating process is carried out under conditions that produce the "first current density" during a "deposition-dissolution process" where the "difference in charge" was large. Accordingly, based on the analysis results (the analysis result data D1) of the "process Bb", it is possible to specify the "current density" that enables the desired amount of metal to be deposited on the plated object with a desired "current efficiency: cathode efficiency" during a plating process that uses the electroplating solution Xa to be analyzed.

In addition, as the "process Cb", a process that analyzes, based on the sets of measurement value data D0 acquired by the measurement value acquiring process, whether impurities are included in the electroplating solution Xa to be analyzed and, when impurities are included, the included amount of impurities is executed. More specifically, based on the current value of the "second current" in each "deposition-dissolution process", the analysis concludes that impurities are included in the electroplating solution Xa when the current value of the "second current" is at least equal to a reference current value set in advance.

More specifically, as shown in FIG. 6, in the "deposition-dissolution process" where the voltage value of the "first voltage" applied between both electrodes 11 and 12 during the "process 1B" is −0.6V, for example, when no impurities are mixed into the electroplating solution Xa, the current values of the "second current" flowing between both electrodes 13 and 12 during the "process 2B" are the values shown by the graph Ga1. Also, when 100 ppm of copper sulfate are mixed into the electroplating solution Xa, the current values of the "second current" flowing between both electrodes 13 and 12 during the "process 2B" are the values shown by the graph Ga2, when 500 ppm of copper sulfate are mixed into the electroplating solution Xa, the current values of the "second current" flowing between both electrodes 13 and 12 during the "process 2B" are the values shown by the graph Ga3, and when 1000 ppm of copper sulfate are mixed into the electroplating solution Xa, the current values of the "second current" flowing between both electrodes 13 and 12 during the "process 2B" are the values shown by the graph Ga4. Accordingly, by comparing the current values shown in the graph Ga1 (current values measured in a state where no impurities such as copper sulfate are mixed in) and the current values actually measured during the "process 2B", it is possible to specify whether copper sulfate is mixed into the electroplating solution Xa.

Also, as shown in FIG. 7, in the "deposition-dissolution process" where the voltage value of the "first voltage" applied between both electrodes 11 and 12 during the "process 1B" is −1.6V, for example, when impurities are not mixed into the electroplating solution Xa, the current values of the "second current" flowing between both electrodes 13 and 12 during the "process 2B" are the values shown by the graph Gb1. Also, when 100 ppm of copper sulfate are mixed into the electroplating solution Xa, the current values of the "second current" flowing between both electrodes 13 and 12 during the "process 2B" are the values shown by the graph Gb2, when 500 ppm of copper sulfate are mixed into the electroplating solution Xa, the current values of the "second current" flowing between both electrodes 13 and 12 during the "process 2B" are the values shown by the graph Gb3, and when 1000 ppm of copper sulfate are mixed into the electroplating solution Xa, the current values of the "second current" flowing between both electrodes 13 and 12 during the "process 2B" are the values shown by the graph Gb4. Accordingly, by comparing the current values shown in the graph Gb1 (current values measured in a state where no impurities such as copper sulfate are mixed in) and the current values actually measured during the "process 2B", it is possible to specify whether copper sulfate is mixed into the electroplating solution Xa.

Here, the applicant has confirmed that the integrated current value of the current value flowing between both electrodes 13 and 12 during the "process 2B" and the concentration of copper sulfate included in the electroplating solution Xa are in a proportional relationship, and that such proportional relationship differs according to the voltage value applied between both electrodes 11 and 12 during the "process 1B". More specifically, like the example in FIG. 6, when the voltage value of the "first voltage" applied between both electrodes 11 and 12 during the "process 1B" is −0.6V, the relationship between the integrated current value during the "process 2B" and the concentration of copper sulfate is the relationship shown by the approximation line Ga in FIG. 5. Also, like the example in FIG. 7, when the voltage value of the "first voltage" applied between both electrodes 11 and 12 during the "process 1B" is −1.6V, the relationship between the integrated current value during the "process 2B" and the concentration of copper sulfate is the relationship shown by the approximation line Gb in FIG. 5.

Accordingly, in this example, it is possible to specify the concentration of copper sulfate included in the electroplating solution Xa based on either the integrated current value during the "process 2B" when the voltage value of the "first voltage" is −0.6V or the integrated current value during the "process 2B" when the voltage value of the "first voltage" is −1.6V. Here, as one example, when trying to specify the concentration of copper sulfate based on only the integrated current value during the "process 2B" when the voltage value of the "first voltage" is −0.6V, if a measurement error occurs during the "process 2B", there is the risk that the specified concentration of the copper sulfate will be inaccurate. Accordingly, by specifying the concentration of copper sulfate based on both integrated current values during the "process 2B" when the voltage value of the "first voltage" is −0.6V and when the voltage value of the "first voltage" is −1.6V, it is possible to specify an accurate concentration.

In addition, as the "process Db", a process (another analysis process relating to "current efficiency: cathode efficiency") that analyzes, based on the sets of measurement value data D0 acquired by the measurement value acquiring process, the state of the relationship between the current density in a plating process that uses the electroplating solution Xa to be analyzed and the amount of charge that contributes to the deposition of metal on the plated object out of the charge applied to the electroplating solution Xa is executed.

Here, although the "process Db" has an analysis procedure that resembles the "process Bb" described above which concludes that the charge that does not contribute to the deposition of metal decreases as the plating process is carried out under conditions that produce a current density where the difference between the "first charge" and the "second charge" is small, the analysis procedure of the "process Db" differs to the "process Bb" by concluding that the charge that contributes to the deposition of metal increases as the plating process is carried out under conditions that produce a current density for which the ratio of the "third charge that contributes to dissolution of metal out of the second charge" to the "first charge" is high. More specifically, in the "process Db" first, the "first charge" is calculated for each "deposition-dissolution process" based on the current value of the "first current" and the "first period", the "third charge" that contributes to the dissolution of metal out of the "second charge" is calculated for each deposition-dissolution process based on the current value of the "second current" and the "state of change in the current value during the second period", and the "first current density" is calculated for each "deposition-dissolution process" based on the electrode area of the working electrode 12 and the current value of the "first current".

More specifically, in the example of the "deposition-dissolution process" shown in FIG. 8, in the same way as the "process Bb" described earlier, the current value (the first current density) of the "process 1B" and the charge (first charge) that is applied to the electroplating solution Xa for the period T1 during the "process 1B" is calculated. The "third charge" is also calculated based on the current values (current values sampled at 10 ms intervals) that change between the current value 0 to the current value B2a during the period T2 from time t2a to time t2b.

Note that the example in FIG. 8 shows an example where the "process 1B" and the "process 2B" have been executed for electroplating solution Xa that includes impurities. This means that in the example in FIG. 8, when a voltage whose voltage value changes with a rate of change of 10 mV/s during the period T2 from time t2a to time t2b during the "process 2B" is applied between both electrodes 11 and 12, a current that changes from the current value 0 to the current value B2a for the period Ta from time ta to time tb3 flows between both electrodes 13 and 12 due to the dissolution of metal deposited on the working electrode 12, and after this, a current that changes from the current value 0 to the current value B2b for the period Tb from time tb3 to time tc flows between both electrodes 13 and 12 due to the dissolution of metal deposited on the working electrode 12.

Here, the current value at which impurities are dissolved into the electroplating solution Xa during the "process 2B" differs to the voltage value at which metal is dissolved into the electroplating solution Xa. For this reason, based on the state of changes in the current value (a current value sampled at 10 ms intervals) of the current flowing between both electrodes 13 and 12 for the period T for time ta to tc during the "process 2B", it is possible to specify a period for which a current flowed between both electrodes 13 and 12 due to the dissolution of metal and a period for which a current flowed between both electrodes 13 and 12 due to the dissolution of impurities.

More specifically, in the example in FIG. 8, the amount of metal dissolved from the working electrode 12 into the electroplating solution Xa reaches a maximum at the time tb1 when the voltage applied between both electrodes 11 and 12 reaches the voltage value Ab1 (where the current flowing between both electrodes 13 and 12 reaches the current value B2a), most of the metal deposited on the working electrode 12 will have been dissolved into the electroplating solution Xa at the time tb3 where the applied voltage reaches the voltage value Ab3, at the same time, dissolution of impurities from the working electrode 12 into the electroplating solution Xa starts, the amount of impurities dissolved from the working electrode 12 into the electroplating solution Xa reaches a maximum at the time tb2 when the applied voltage reaches the voltage value Ab2 (where the current flowing between both electrodes 13 and 12 reaches the current value B2b), and all of the impurities deposited on the working electrode 12 will have been dissolved into the electroplating solution Xa at the time tc where the applied voltage reaches the voltage value Ac.

Accordingly, in the example in FIG. 8, the charge (the third charge) that contributes to the "deposition of metal" out of the charge (the second charge) applied to the electroplating solution Xa during the "process 2B" is calculated based on the integrated value of the current value that changes from the current value 0 to the current value B2a (the current value of the current that flows between both electrodes 13 and 12 due to the dissolution of metal) for the period Ta from time ta to time tb3 and the period Ta for which a current flowed between both electrodes 13 and 12. This calculation process is executed for each set of measurement value data D0 of the fifteen iterations of the "deposition-dissolution process".

Next, the state of the electroplating solution Xa is analyzed based on the calculated values of the "first current density", the "first charge" and the "third charge". More specifically, the analysis concludes that the electroplating solution Xa to be analyzed is in a state such that the charge that contributes to deposition of metal onto the plated object increases (i.e., the "current efficiency: cathode efficiency" improves) as the plating process is carried out under conditions that produce the "first current density" during a "deposition-dissolution process" where the ratio of the "third charge" to the "first charge" is large (i.e., a value produced by dividing the value of the "third charge" by the "first charge" is large) and the charge that contributes to deposition of metal onto the plated object decreases (i.e., the "current efficiency: cathode efficiency" worsens) as the plating process is carried out under conditions that produce the "first current density" during a "deposition-dissolution process" where the ratio of the "third charge" to the "first charge" is small (i.e., a value produced by dividing the value of the "third charge" by the "first charge" is small). More specifically, the analysis concludes that the electroplating solution Xa to be analyzed is in a state such that the charge that contributes to deposition of metal onto the plated object (i.e., the "current efficiency: cathode efficiency") increases when the plating process is carried out under conditions where the "first current density" during the "deposition-dissolution process" is such that the ratio of the "third charge" to the "first charge" is large (a value produced by dividing the value of the "third charge" by the "first charge" is large) and the charge that contributes to deposition of metal onto the plated object (i.e., the "current efficiency: cathode efficiency") decreases when the plating process is carried out under conditions where the "first current density" during the "deposition-dissolution process" is such that the ratio of the "third charge" to the "first charge" is small (a value produced by dividing the value of the "third charge" by the "first charge" is small). Accordingly, based on the analysis results (analysis result data D1) of the "process Db", during a plating process that uses the electroplating solution Xa to be analyzed, it is possible to specify the "current density" that enables a desired amount of metal to be deposited on the plated object with the desired "current efficiency: cathode efficiency".

In addition, as the "process Eb", a process that analyzes the state of the relationship between the current density of the plating process that uses the electroplating solution Xa to be analyzed and the dissolution rate by which the plated object dissolves due to an oxidation reaction during the plating process is executed based on the sets of measurement value data D0 acquired by the "measurement value acquiring process".

Here, when a voltage is applied between the plated object (cathode) and the electrode (anode) to produce a set current density during the plating process, in addition to metal and impurities in the electroplating solution being deposited on the plated object due to a reduction reaction, the plated object also dissolves due to an oxidation reaction (dissolution of the plated object into the electroplating solution). The ratio between the charge that contributes to the reduction reaction and the charge that contributes to the oxidation reaction out of the charge applied to the electroplating solution during the plating process also differs according to the voltage value of the voltage applied between the plated object and the electrode. Accordingly, when the current density during the plating process is set in view only of the reduction reaction, there is the risk of the dissolved amount of the plated object exceeding a tolerated range, resulting in defective products being manufactured. For this reason, to set favorable manufacturing conditions, it is preferable to specify the relationship between the current density during the plating process and the rate of dissolution of the plated object in advance.

In this "process Eb", the state of the electroplating solution Xa is analyzed using both the measurement value data D0 acquired by the "measurement value acquiring process 1b" that uses the working electrode 12 with an electrode surface formed of platinum that is highly insoluble in the electroplating solution Xa and the measurement value data D0a acquired by the "measurement value acquiring process 2b" that uses the working electrode 12a with an electrode surface formed of copper in the same way as the plated object.

More specifically, first, the "first current density" is calculated for each "deposition-dissolution process" based on the electrode area of the working electrodes 12 and 12a and the current value of the "first current". Also, based on the current value of the "second current" during the "measurement value acquiring process 1b" (a current value specified based on the measurement value data D0) and the "second period" for which the "second current" flowed, the "fourth charge" that is applied to the electroplating solution Xa during the "process 2B" during the "measurement value acquiring process 1b" is calculated for each "deposition-dissolution process". Also, based on the current value of the "second current" during the "measurement value acquiring process 2b" (a current value specified based on the measurement value data D0a) and the state of change in the "second period" for such current value, the "fifth charge" that contributes to dissolution of metal during the "process 2B" during the "measurement value acquiring process 2b" is calculated for each "deposition-dissolution process". In addition, for each "deposition-dissolution process" where the voltage value of the "first voltage" applied during the "process 1B" is equal, the "sixth charge" that is the difference between the "fourth charge" and the "fifth charge" is calculated.

More specifically, as one example, in the example of the "deposition-dissolution process" shown in FIG. 9, for the current values measured during the "process 2B", measurement values of the "measurement value acquiring process 1b" that uses the working electrode 12 are shown by the solid line and measurement values of the "measurement value acquiring process 2b" that uses the working electrode 12a are shown by the broken line. Here, since an oxidation reaction does not occur at the electrode surface during the "process 1B" of the "measurement value acquiring process 1b" that uses the working electrode 12 whose electrode surface is formed of platinum that is highly insoluble in the electroplating solution Xa, most of the "first charge" applied to the electroplating solution Xa contributes to deposition of metal and the like (the reduction reaction) and to electrolysis of the water included in the electroplating solution Xa. Since a large amount of metal is deposited on the electrode surface of the working electrode 12 as a result, during the "process 2B", the period Ta from time ta to time tca is required to dissolve such metal into the electroplating solution Xa.

On the other hand, during the "process 1B" of the "measurement value acquiring process 2b" that uses the working electrode 12a whose electrode surface is made of copper in the same way as the plated object, since an oxidation reaction occurs at the electrode surface, the "first charge" applied to the electroplating solution Xa contributes not only to the deposition of metal (reduction reaction) and the like and to electrolysis of the water included in the electroplating solution Xa but also to dissolution of the copper of the working electrode 12a (i.e., dissolution into the electroplating solution Xa). For this reason, when a voltage with the voltage value A1 is applied between the reference electrode 11 and the working electrode 12a for the period T1 from time t1a to time t1b which is the same as the "process 1B" where the working electrode 12 is used, the amount of metal deposited onto the electrode surface of the working electrode 12a is smaller than the amount of metal deposited onto the surface of the working electrode 12 during the "measurement value acquiring process 1*b*".

Also, during the "process 2B" of the "measurement value acquiring process 2*b*" that uses the working electrode 12*a*, after the metal deposited onto the electrode surface of the working electrode 12*a* has dissolved into the electroplating solution Xa (a state where the electrode surface of the working electrode 12*a* has become exposed), the electrode surface itself of the working electrode 12*a* is dissolved into the electroplating solution Xa due to an oxidation reaction at the electrode surface. As one example, in the example shown in FIG. 9, when a voltage whose voltage value changes at a rate of change of 10 mV/s during the period T2 from time t2a to time t2b is applied between both electrodes 11 and 12*a*, the metal (in the present embodiment, nickel) deposited on the electrode surface of the working electrode 12*a* by the "process 1B" starts to be dissolved into the electroplating solution Xa from time to when the voltage between both electrodes 11 and 12 reaches the voltage value Aa and becomes almost completely dissolved in the electroplating solution Xa at time tcb where the voltage value reaches Acb (a state where the electrode surface of the working electrode 12*a* is exposed).

For this reason, the copper that constructs the electrode surface of the working electrode 12*a* starts to be dissolved into the electroplating solution Xa, and for the period Tca until the time td where the voltage between both electrodes 11 and 12*a* reaches the voltage value Ad, dissolution of the copper constructing the electrode surface into the electroplating solution Xa continues. In addition, at the time to where the voltage between both electrodes 11 and 12*a* reaches the voltage value Ae, the copper that constructs the electrode surface of the working electrode 12*a* again starts to be dissolved into the electroplating solution Xa and for the period Tcb until the time tf where the voltage between both electrodes 11 and 12*a* reaches the voltage value Af, dissolution of the copper constructing the electrode surface into the electroplating solution Xa continues. Here, as in the illustrated example, the voltage value at which the metal (nickel) is dissolved into the electroplating solution Xa during the "process 2B" and the voltage value at which the copper constructing the electrode surface of the working electrode 12*a* is dissolved into the electroplating solution Xa differ. This means that based on the state of change in the current value (a current value sampled at 10 ms intervals) of the current between both electrodes 13 and 12*a* from time ta to time tf during the "process 2B", it is possible to specify the time for which a current flowed between both electrodes 13 and 12*a* due to the dissolution of metal and the time for which a current flowed between both electrodes 13 and 12*a* due to the dissolution of copper.

Accordingly, in the illustrated example, based on the integrated value of the current value (the current value of a current flowing between both electrodes 13 and 12*a* due to the dissolution of metal) that changes from the current value 0 to the current value B2 during the period Tb from time ta to time tcb and the period Tb for which the current flows between both electrodes 13 and 12*a*, the charge (fifth charge) that contributes to the "deposition of metal") out of the charge applied to the electroplating solution Xa during the "process 2B" is calculated. The processing that calculates the "fifth charge" is executed for each "process 2B" in each "measurement value acquiring process 2*b*". Note that since the processing that calculates the "fourth charge" is the same as the calculation process of the "first charge" during the "process Bb" described earlier, detailed description thereof is omitted here. Next, the "sixth charge" that is the difference between the "fourth charge" and the "fifth charge" is calculated for each of the fifteen iterations of the "deposition-dissolution process".

After this, the state of the electroplating solution Xa is analyzed based on the calculated values of the "first current density" and the "sixth charge". More specifically, the analysis concludes that the electroplating solution Xa is in a state where the rate of dissolution (dissolution efficiency) per unit time of the plated object falls as the plating process is carried out under conditions that produce a "first current density" for which the "sixth charge" is small and the rate of dissolution (dissolution efficiency) per unit time of the plated object rises as the plating process is carried out under conditions that produce a "first current density" for which the "sixth charge" is large. Accordingly, based on the analysis results (analysis result data D1) of the "process Eb", it is possible to specify a "current density" capable of depositing metal on the plated object without causing excessive dissolution of the plated object during a plating process that uses the electroplating solution Xa to be analyzed.

In addition, as the "process Fb", a process (an analysis process relating to "critical current density (lower limit value)", "uniform electrodeposition (lower limit)" and "covering power") that specifies, based on the sets of measurement value data D0 described above that have been acquired by the "measurement value acquiring process", a lower limit value ("current density lower limit value) of the current density that is capable of depositing at least an amount of metal set in advance on the plated object during a plating process that uses the electroplating solution Xa to be analyzed is executed.

More specifically, in the "process Fb", first the "second charge" is calculated for each "deposition-dissolution process" based on the current value of the "second current" and the "second period", the amount of metal deposited on the working electrode 12 during the "process 1B" is calculated for each "deposition-dissolution process" based on each "second charge", and the "first current density" is calculated for each "deposition-dissolution process" based on the electrode area of the working electrode 12 and the current value of the "first current".

Here, the larger the amount of metal deposited on the working electrode 12 during the "process 1B" described earlier, the higher the charge applied to the electroplating solution Xa during the "process 2B" to have such metal dissolved into the electroplating solution Xa, and the smaller the amount of metal deposited on the working electrode 12 during the "process 1B", the lower the charge applied to the electroplating solution Xa during the "process 2B" to have such metal dissolved into the electroplating solution Xa. Accordingly, by calculating the charge applied to the electroplating solution Xa during the "process 2B", it is possible to specify the amount of metal deposited on the working electrode 12 during the "process 1B". More specifically, it is possible to calculate the amount of metal deposited on the cathode according to "charge/(valence of metal×Faraday constant).

By doing so, as shown by the line graph G in FIG. 4, the relationship is specified between the "first current density" (the voltage value of the "first voltage" applied between both electrodes 11 and 12 in FIG. 4) in each "deposition-dissolution process" and the amount of metal deposited on the working electrode 12 during each "deposition-dissolution process" (in FIG. 4, the charge applied to the electroplating solution Xa during the "process 2B": the charge required to dissolve the metal that was deposited on the working electrode 12 into the electroplating solution Xa).

Next, the state of the electroplating solution Xa is analyzed based on the calculated amount of metal and "first current density". More specifically, the "current density lower limit value" of the "first current density" that is capable of depositing at least an amount of metal set in advance on the working electrode 12 is specified and the analysis concludes that the electroplating solution Xa is in a state where it is not possible to deposit at least the amount of metal set in advance on the plated object when the plating process is carried out under conditions that produce a "first current density" that falls below the "current density lower limit value". Here, in the present embodiment, as shown in FIG. 4, the current density of the working electrode 12 during the first iteration of the "deposition-dissolution process" when the voltage value of the "first voltage" applied between both electrodes 11 and 12 during the "process 1B" is −3.4V is specified as the lower limit value of the "critical current density" and the analysis concludes that metal will not be deposited on the plated object when a plating process is carried out at a current density that falls below such current density. Note that "uniform electrodeposition (lower limit)" and "covering power" will be described later for the "process Gb".

On the other hand, as the "process Gb", a process (an analysis process relating to "critical current density (upper limit value)", "uniform electrodeposition (upper limit)" and "covering power") that specifies an upper limit value of the current density ("critical current density upper limit value") that is capable of depositing at least an amount of metal set in advance on the plated object during a plating process that uses the electroplating solution Xa to be analyzed based on the sets of measurement value data D0 described above acquired by the "measurement value acquiring process" is executed.

More specifically, in the "process Gb", in the same way as the "process Fb" described above, the "second charge" is calculated for each "deposition-dissolution process" based on the current value of the "second current" and the "second period", the amount of metal deposited on the working electrode 12 during the "process 1B" is calculated for each "deposition-dissolution process" based on each "second charge", and the "first current density" is calculated for each "deposition-dissolution process" based on the electrode area of the working electrode 12 and the current value of the "first current".

Next, the state of the electroplating solution Xa is analyzed based on the calculated amount of metal and "first current density". More specifically, the "current density upper limit value" of the "first current density" that is capable of depositing at least an amount of metal set in advance on the working electrode 12 is specified and the analysis concludes that the electroplating solution Xa is in a state where it is not possible to deposit at least the amount of metal set in advance on the plated object when the plating process is carried out under conditions where the "first current density" exceeds the "current density upper limit value". Here, in the present embodiment, as shown in FIG. 4, the current density of the working electrode 12 during the fifteenth iteration of the "deposition-dissolution process" when the voltage value of the "first voltage" applied between both electrodes 11 and 12 during the "process 1B" is −0.6V is specified as the upper limit value of the "critical current density", and the analysis concludes that metal will not be deposited on the plated object when a plating process is carried out at a current density that exceeds such current density.

Next, the state of the electroplating solution Xa relating to "uniform electrodeposition" is analyzed from the calculation results of the "process Fb" and the "process Gb" described above. Here, during a plating process that uses the electroplating solution Xa to be analyzed, the voltage value of the voltage applied between the plated object and the electrode may vary within a certain range, such as when equipment aside from the plating process apparatus is started or stopped. Accordingly, it is necessary to specify a current density range where there is no large variation in the amount of metal deposited on the plated object even when the voltage value of the voltage applied between the plated object and the electrode varies (i.e., a range where uniform electrodeposition is ensured).

As one example, as shown in FIG. 4, when it has been defined that "uniform electrodeposition" of the product is ensured by keeping the range in which charge applied to the electroplating solution Xa (that is, the amount of metal deposited on the working electrode 12) during the "process 2B" changes due to variation in the voltage value of the "first voltage" applied between both electrodes 11 and 12 during the "process 1B" to a range where the charge is Ca1 to Ca2, the analysis concludes that the plating process should be executed within a current density range corresponding to the range Ha with the voltage values Va1 to Va2. Note that the range of charge (the range of the amount of metal) analyzed as ensuring "uniform electrodeposition" of products is set in advance by the user.

Next, the state of the electroplating solution Xa relating to "covering power" is analyzed from the calculation results of the "process Fb" and the "process Gb" described above. Here, as shown in FIG. 4, when it has been defined that the "covering power" for products is sufficient when an amount of metal that requires at least a charge of Cb as the charge applied to the electroplating solution Xa during the "process 2B" has been deposited, for example, the analysis concludes that it is sufficient to execute the plating process with a current density range corresponding to the range Hb with the voltage values Vb1 to Vb2. Note that the range of charge (the range of the amount of metal) analyzed as ensuring a sufficient "covering power" of products is also set in advance by the user.

After the "processes Ab to Gb" have been sequentially executed, the processing unit 33 generates the analysis result data D1 in which the analysis results are recorded, stores the analysis result data D1 in the storage unit 34, and displays graphs and analysis values showing the analysis results on the display unit 32. By doing so, the "analysis process" for setting the processing conditions of the electroplating process that uses the electroplating solution Xa in the plating solution tank X is completed.

After this, the user refers to the analysis results displayed on the display unit 32 and arbitrarily sets the processing conditions for a plating process that uses the electroplating solution Xa that has been analyzed. Here, when the results of the analysis during the "process Cb" conclude that more than a tolerated amount of impurities are included in the electroplating solution Xa in the plating solution tank X, the electroplating solution Xa in the plating solution tank X is replaced with new electroplating solution Xa that does not include impurities and analysis processes are executed again in the same way as the series of analysis processes described above. Also, when the results of the analysis during the "process Cb" described above conclude that impurities are not included in the electroplating solution Xa or the amount of impurities included in the electroplating solution Xa is equal to or less than the tolerated amount, the user specifies a current density capable of favorably depositing a sufficient amount of metal that has low power consumption and does not cause excessive dissolution of the plated object based on the results of the analysis in the "processes Ab, Bb, and Db to Gb".

After this, in keeping with the area of the product to be manufactured, the thickness of the metal film to be formed, and the like, the voltage value of the voltage applied between the product (cathode) and the anode is decided so as to produce the current density specified by the analysis results described above, and an electroplating process is executed on products. At this time, on determining that it is possible to manufacture favorable products by executing the electroplating process with the same current density as the "process 1B" where the voltage value A1 of the voltage applied between the electrodes is −1.6V out of the "process 1B" in each of the fifteen iterations of the "deposition-dissolution process" described above, the voltage value of the voltage applied between the product (cathode) and anode to produce such current density (i.e., the "process conditions") is decided. By doing so, it is possible to carry out the plating process with favorable conditions that are suited to the electroplating solution Xa inside the plating solution tank X, and as a result, it is possible to manufacture favorable products (plated products).

Also, by operating the analyzing apparatus 3, the measurement value data D0 and D0a acquired by the "deposition-dissolution process" when the voltage value A1 applied between both electrodes 11 and 12 (12a) during the "process 1B" is −1.6V out of the fifteen iterations of the "deposition-dissolution process" described above are designated as the "reference values" for subsequently monitoring the state of electroplating solution Xa in the plating solution tank X.

Note that to distinguish between the measurement value data D0 and D0a designated by the user as the "reference values" and the measurement value data D0 and D0a generated by the other fourteen iterations of the "deposition-dissolution process" and the measurement value data D0 and D0a generated by the "measurement value acquiring process" executed thereafter to analyze the state of changes in the electroplating solution Xa, the measurement value data D0 acquired by the "deposition-dissolution process" when the voltage value A1 of the voltage applied during the "process 1B" is −1.6V and designated as the "reference values" is also referred to as the "reference value data DC" and the measurement value data D0a acquired by the "deposition-dissolution process" when the voltage value A1 of the voltage applied during the "process 1B" is −1.6V and designated as the "reference values" is also referred to as the "reference value data DCa".

On the other hand, even when favorable processing conditions for the electroplating process have been set by the series of analysis processes described above, as described earlier, in keeping with an increase in the total usage period of the electroplating solution (the number of iterations of the electroplating process), the state of the electroplating solution Xa in the plating solution tank X will change due to the mixing of impurities into the electroplating solution Xa, evaporation of electrolyte, and the like, so that the amount of metal deposited per unit time and the dissolution amount of the plated object per unit time when a voltage of a predetermined voltage value is applied between the plated object (cathode) and the anode will change. Accordingly, to avoid the manufacturing of defective products, it is necessary, whenever a number of iterations set in advance (a usage period set in advance) has been executed, it is necessary to analyze the state of the electroplating solution Xa in the plating solution tank X and to change the processing conditions and/or to replace with new electroplating solution Xa as necessary.

More specifically, as one example, when the number of executions of the electroplating process that uses the electroplating solution Xa in the plating solution tank X has reached a number of iterations set in advance, the "measurement value acquiring process" (the measurement value acquiring process 1b and the measurement value acquiring process 2b) and the "analysis process" described above are executed and the state of changes in the electroplating solution Xa is analyzed by comparing with the reference value data DC and DCa. Note that since the assembly work of the electrochemical measuring apparatus 2, installation work on the plating solution tank X, and the work of connecting the electrochemical measuring apparatus 2 to the analyzing apparatus 3 after the "measurement process" has been completed and transmitting the measurement value data D0 and D0a are the same as when the processes described earlier are executed, detailed description thereof is omitted here. Also, for the processes described below, detailed description is omitted for processes that are the same as the processes described above that are carried out with the object of setting the processing conditions and acquiring the reference values.

In the measurement value acquiring process (the "measurement value acquiring process 1b" and the "measurement value acquiring process 2b") that have an object of analyzing the state of changes in the electroplating solution Xa, as one example, the "deposition-dissolution process" is carried out by setting the voltage value A1 of the voltage applied between both electrodes 11 and 12 (12a) during the "process 1B" described above at −1.6V and setting the voltage value range and rate of change of the voltage applied between both electrodes 11 and 12 (12a) during the "process 2B" in the same way in as each "process 2B" described earlier. By doing so, a state is produced where the measurement value data D0 and D0a that can be used to analyze the state of changes in the electroplating solution Xa are stored in the storage unit 24. Next, the measurement value data D0 and D0a are transmitted from the electrochemical measuring apparatus 2 to the analyzing apparatus 3. By doing so, the "measurement value acquiring process" is completed and a state where the measurement value data D0 and D0a that make it possible to specify the state of the electroplating solution Xa at that time are stored in the storage unit 34.

After this, the "analysis process" is executed at the analyzing apparatus 3. When doing so, in the electroplating solution analyzing system 1 (the analyzing apparatus 3) according to the present embodiment, the processing unit 33 executes the same processing as the analysis processes in "process Ab to Eb" described earlier based on the measurement value data D0 and D0a acquired from the electrochemical measuring apparatus 2 and the reference value data DC and DCa stored in the storage unit 34, analyzes how the electroplating solution Xa in the plating solution tank X has changed and by how much, generates the analysis result data D1 that shows the analysis results, and stores the analysis result data D1 in the storage unit 34.

In this case, during the "process Ab" in the "analysis process" that analyzes the state of changes in the electroplating solution Xa, as one example, a process that analyzes how the relationship between the voltage (current density) applied between the plated object (cathode) and the electrode (anode) during a plating process that uses the electroplating solution Xa to be analyzed and the amount of metal deposited per unit time on the plated object is executed based on the reference value data DC stored in the storage unit 34 as reference values and the measurement value data D0 acquired by the "measurement value acquiring process" described above.

More specifically, during the "process Ab", first, the "second charge" applied to the electroplating solution Xa during the "process 2B" is calculated based on the current value of the "second current" specified based on the measurement value data D0 and the "second period" for which the "second current" flowed between the counter electrode 13 and the working electrode 12 during the "process 2B" when the measurement value data D0 was acquired. In the same way, the "second charge (one example of the "reference values A") applied to the electroplating solution Xa during the "process 2B" is calculated based on the current value of the "second current" specified based on the reference value data DC and the "second period" for which the "second current" flowed between the counter electrode 13 and the working electrode 12 during the "process 2B" when the reference value data DC was acquired.

After this, the state of the electroplating solution Xa is analyzed based on both calculated values of the "second charge". More specifically, as one example, when measurement values such as those shown in the graph G10a were obtained during the "process 2B" of the "measurement value acquiring process" described above for an electroplating solution Xa for which measurement values such as those shown in the graph G10 shown in FIG. 10 were obtained during the "process 2B" when acquiring the reference value data DC (reference values), the "second charge" calculated based on the measurement value data D0 will be larger than the "second charge (reference values A)" calculated based on the reference value data DC. At this time, the analysis by the processing unit 33 concludes that the electroplating solution Xa in the plating solution tank X has changed to a state where the amount of metal deposited per unit time during the plating process is larger than a state where the reference value data DC (reference values A) is capable of being acquired (in the present embodiment, a state where the electroplating solution Xa in the plating solution tank X is new: one example of a "reference state A").

On the other hand, when measurement values such as those shown in the graph G10b were obtained during the "process 2B" of the "measurement value acquiring process" described above for an electroplating solution Xa for which measurement values such as those shown in the graph G10 were obtained during the "process 2B" when acquiring the reference value data DC (reference values), the "second charge" calculated based on the measurement value data D0 will be smaller than the "second charge (reference values A)" calculated based on the reference value data DC. At this time, the analysis by the processing unit 33 concludes that the electroplating solution Xa in the plating solution tank X has changed to a state where the amount of metal deposited per unit time during the plating process is smaller than the "reference state A" described above. Accordingly, based on the analysis results (the analysis result data D1) of the "process Ab", it is possible to specify whether the electroplating solution Xa to be analyzed is in a state capable of depositing the desired amount of metal per unit time on the plated object and as necessary to change the current density during the plating process and/or replace with new electroplating solution Xa.

Also, in the "process Bb" of the "analysis process" that analyzes changes to the electroplating solution Xa, as one example a process that analyzes how the relationship between the current density in the plating process that uses the electroplating solution Xa to be analyzed and the amount of charge that does not contribute to the deposition of metal on the plated object out of the charge applied to the electroplating solution Xa has changed (an analysis process relating to the state into which the "current efficiency: cathode efficiency") has changed) is executed based on the reference value data DC stored in the storage unit 34 as reference values and the measurement value data D0 acquired by the "measurement value acquiring process" described above.

More specifically, in the "process Bb", first, the "first charge" applied to the electroplating solution Xa during the "process 1B" is calculated based on the current value of the "first current" and the "first period" specified based on the measurement value data D0, the "second charge" is calculated based on the current value of the "second current" and the "second period" specified based on the measurement value data D0, and the difference between the "first charge" and the "second charge" is calculated. In the same way, the "first charge" applied to the electroplating solution Xa during the "process 1B" is calculated based on the current value of the "first current" and the "first period" specified based on the reference value data DC, the "second charge" is calculated based on the current value of the "second current" and the "second period" specified based on the reference value data DC, and the difference (one example of a "reference value B") between the "first charge" and the "second charge" is calculated.

Next, the state of the electroplating solution Xa is analyzed based on both calculated values of the "difference in charge". More specifically, when the "difference in charge calculated based on the measurement value data D0 is smaller than the "difference in charge (the reference value B)" calculated based on the reference value data DC, the analysis concludes that the electroplating solution Xa in the plating solution tank X has changed to a state where the charge that does not contribute to the deposition of metal during the plating process has decreased compared to a state capable of acquiring the reference value data DC (the reference values B) (in the present embodiment, a state where the electroplating solution Xa in the plating solution tank X is new: one example of a "reference state B").

Also, when the "difference in charge" calculated based on the measurement value data D0 is larger than the "difference in charge (the "reference value B")" calculated based on the reference value data DC, the analysis by the processing unit 33 concludes that the electroplating solution Xa in the plating solution tank X has changed to a state where the charge that does not contribute to the deposition of metal during the plating process has increased compared to the "reference state B" described above. Accordingly, based on the analysis results (the analysis result data D1) of this "process Bb", it is possible to specify whether the electroplating solution Xa to be analyzed is in a state capable of depositing the desired amount of metal on the plated object with the desired "current efficiency: cathode efficiency" and as necessary to change the current density during the plating process and/or replace with new electroplating solution Xa.

In addition, in the "process Cb" in the "analysis process" that analyzes the state of changes in the electroplating solution Xa, a process that analyzes, based on the reference value data DC stored in the storage unit 34 as reference values and the measurement value data D0 acquired by the "measurement value acquiring process" described above, whether impurities are included in the electroplating solution Xa to be analyzed and when included, the amount of included impurities.

More specifically, in this "process Cb", the current value of the "second current" specified based on the measurement value data D0 and the current value of the "second current (one example of the reference values C)" specified based on the reference value data DC are compared. Here, when the current value of the "second current" specified based on the measurement value data D0 is larger than the current value (the reference value C) of the "second current" specified based on the reference value data DC, the analysis concludes that the amount of impurities included in the electroplating solution Xa in the plating solution tank X is larger than a state capable of acquiring the reference value data DC (the reference value C) (in the present embodiment, a state where the electroplating solution Xa in the plating solution tank X is new: one example of a "reference state C").

Also, when the current value of the "second current" specified based on the measurement value data D0 is smaller than the current value (the reference value C) of the "second current" specified based on the reference value data DC, the analysis concludes that the amount of impurities included in the electroplating solution Xa in the plating solution tank X has changed to a state that is smaller than the "reference state C" described above. Accordingly, based on the analysis results (the analysis result data D1) of the "process Cb", it is possible to specify whether impurities are mixed into the electroplating solution Xa (or whether the concentration of impurities has changed) and to replace with new electroplating solution Xa as necessary.

Also, in the process "Db" in the "analysis process" that analyzes the state of changes in the electroplating solution Xa, as one example a process (another analysis process relating to how the "current efficiency: cathode efficiency" has changed) that analyzes how the relationship between the current density in the plating process that uses the electroplating solution Xa to be analyzed and the amount of charge that contributes to the deposition of metal on the plated object out of the charge applied to the electroplating solution Xa has changed is executed based on the reference value data DC stored in the storage unit 34 as reference values and the measurement value data D0 acquired by the "measurement value acquiring process" described above.

More specifically, in the "process Db", the "first charge" applied to the electroplating solution Xa during the "process 1B" is calculated based on the current value of the "first current" and the "first period" specified based on the measurement value data D0, the "third charge" that contributes to dissolution of metal out of the "second charge" is calculated based on the current value of the "second current" and "state of changes in the current value during the second period" specified based on the measurement value data D0, and the ratio of the "third charge" to the "first charge" is calculated. In the same way, the "first charge" applied to the electroplating solution Xa during the "process 1B" is calculated based on the current value of the "first current" and the "first period" specified based on the reference value data DC, the "third charge" that contributes to dissolution of metal out of the "second charge" is calculated based on the current value of the "second current" and "state of changes in the current value during the second period" specified based on the reference value data DC, and the ratio (one example of the "reference value D") of the "third charge" to the "first charge" is calculated.

Next, the state of the electroplating solution Xa is analyzed based on both calculated values of the "ratio of the third charge to the first charge". More specifically, when the "ratio of the third charge to the first charge (a value produced by dividing the "third charge" by the "first charge")" cal- culated based on the measurement value data D0 is larger than the ratio of the "third charge to the first charge (a value produced by dividing the "third charge" by the "first charge")" calculated based on the reference value data DC, the analysis concludes that the electroplating solution Xa in the plating solution tank X has changed to a state where the charge that contributes to the deposition of metal during the plating process is larger than a state where reference value data DC capable of calculating the "reference value D" described above can be obtained by the "measurement value acquiring process" (in the present embodiment, a state where the electroplating solution Xa in the plating solution tank X is new: one example of a "reference state D").

Also, when the "ratio of the third charge to the first charge" calculated based on the measurement value data D0 is smaller than the "ratio of the third charge to the first charge" calculated based on the reference value data DC, the analysis concludes that the electroplating solution Xa in the plating solution tank X has changed to a state where the charge that contributes to the deposition of metal during the plating process is smaller than a state (the "reference state D") where reference value data DC capable of calculating the "reference value D" described above can be obtained by the "measurement value acquiring process". Accordingly, it is possible to specify, based on the analysis results (analysis result data D1) of the "process Db", whether the electroplating solution Xa to be analyzed is in a state that is capable of depositing the desired amount of metal on the plated object with the desired "current efficiency: cathode efficiency" and as necessary to change the current density during the plating process and/or replace with new electroplating solution Xa.

In addition, in the "process Eb" in the "analysis process" that analyzes the state of changes in the electroplating solution Xa, a process that analyzes how the relationship between the current density during a plating process that uses the electroplating solution Xa to be analyzed and the rate of dissolution of the plated object due to an oxidation reaction during the plating process has changed is executed based on the reference value data DC and DCa stored in the storage unit 34 as reference values and the measurement value data D0 and D0*a* acquired by the "measurement value acquiring process" described above.

More specifically, first, the "fourth charge" applied to the electroplating solution Xa during the "process 2B" in the "measurement value acquiring process 1*b*" is calculated based on the current value (a current value specified based on the measurement value data D0) of the "second current" during the "measurement value acquiring process 1*b*" that acquired the measurement value data D0 and the "second period" for which the "second current" flowed. Also, the "fifth charge" that contributes to the dissolution of metal during the "process 2B" in the "measurement value acquiring process 2*b*" is calculated based on the current value (a current value specified based on the measurement value data D0*a*) of the "second current" during the "measurement value acquiring process 2*b*" that acquired the measurement value data D0*a* and the state of changes in the current value during the "second period". In addition, the "sixth charge" that is the difference between the calculated "fourth charge" and "fifth charge" is calculated.

In the same way, the "fourth charge" applied to the electroplating solution Xa during the "process 2B" in the "measurement value acquiring process 1*b*" is calculated based on the current value (a current value specified based on the reference value data DC) of the "second current" during the "measurement value acquiring process 1*b*" that acquired the measurement value data D0 as the reference value data DC and the "second period" for which the "second current" flowed. Also, the "fifth charge" that contributes to the dissolution of metal during the "process 2B" in the "measurement value acquiring process 2b" is calculated based on the current value (a current value specified based on the reference value data DCa) of the "second current" during the "measurement value acquiring process 2b" that acquired the measurement value data D0a as the reference value data DCa and the state of changes in the current value during the "second period". In addition, the "sixth charge" (one example of the "reference value E") that is the difference between the calculated "fourth charge" and "fifth charge" is calculated.

After this, the state of the electroplating solution Xa is analyzed based on both calculated values of the "sixth charge". More specifically, when the "sixth charge" calculated based on the measurement value data D0 and D0a is smaller than the "sixth charge (the reference value E)" calculated based on the reference value data DC and DCa, the analysis concludes that the electroplating solution Xa in the plating solution tank X has changed to a state where the rate of dissolution per unit time of the plated object is lower than a state (one example of a "reference state E") capable of calculating a "sixth charge" that is equal to the reference value E based on the measurement value data D0 and D0a acquired by the "measurement value acquiring process 1b" and the "measurement value acquiring process 2b".

Also, when the "sixth charge" calculated based on the measurement value data D0 and D0a is larger than the "sixth charge (the reference value E)" calculated based on the reference value data DC and DCa, the analysis concludes that the electroplating solution Xa in the plating solution tank X has changed to a state where the rate of dissolution per unit time of the plated object is higher than a state (one example of the "reference state E") capable of calculating a "sixth charge" that is equal to the reference value E based on the measurement value data D0 and D0a acquired by the "measurement value acquiring process 1b" and the "measurement value acquiring process 2b". Accordingly, it is possible to specify, based on the analysis results (the analysis result data D1) of the "process Eb", whether the electroplating solution Xa to be analyzed is in a state capable of depositing metal on the plated object during the plating process without the plated object excessively dissolving, and as necessary to change the current density during the plating process and/or replace with new electroplating solution Xa.

After the "processes Ab to Eb" described above have been sequentially executed, the processing unit 33 generates the analysis result data D1 in which the analysis results are recorded, stores the analysis result data D1 in the storage unit 34, and displays graphs and analysis values showing the analysis results on the display unit 32. By doing so, the "analysis process" that analyzes how the state of the electroplating solution Xa inside the plating solution tank X has changed is completed.

On the other hand, when the number of executions of the electroplating process that uses the electroplating solution Xa in the plating solution tank X has again reached a number of iterations set in advance, the same processing as the "measurement value acquiring process" and the "analysis process" described above is again executed with the object of analyzing the state of changes in the electroplating solution Xa. By doing so, the state to which the electroplating solution Xa inside the plating solution tank X has changed from the new state is analyzed. Note that in the second and subsequent "analysis process" carried out with the object of analyzing the state of changes in the electroplating solution Xa, in place of the reference value data DC and DCa acquired by the first "measurement value acquiring process" that has an object of setting the processing conditions of the electroplating process, as one example it is possible to use the measurement value data D0 and D0a acquired in the immediately preceding "measurement value acquiring process" as the "reference values". In this case, the manner and extent of change in the electroplating solution Xa inside the plating solution tank X from the immediately preceding analysis are analyzed.

In this way, according to the electroplating solution analyzing system 1 and the electroplating solution analyzing method used by such system, when executing the "measurement value acquiring process" that executes a measurement process that measures the current value of the current flowing between both electrodes 13 and 12 (12a) while applying a voltage between both electrodes 11 and 12 (12a) to acquire the measurement values (measurement value data D0 and D0a) and the "analysis process" that analyzes the state of the electroplating solution Xa based on the acquired measurement values, the "process 1B" that measures, as measurement values, the current value of the "first current" flowing between both electrodes 13 and 12 (12a) while depositing metal on the working electrode 12 (12a) by applying the "first voltage" between both electrodes 11 and 12 (12a) for the "first period", and the "process 2B" that measures, as measurement values, the current value of the "second current" flowing between both electrodes 13 and 12 (12a) with a cycle set in advance while dissolving the metal, which was deposited on the working electrode (12a) during the "process 1B", into the electroplating solution Xa by applying the "second voltage" whose voltage value changes with a rate of change set in advance for the "second period", are executed in that order as the "measurement value acquiring process", and the state of the electroplating solution Xa is analyzed in the "analysis process" based on the measurement values acquired by the "measurement value acquiring process" and the reference values (the reference value data DC and DCa).

Accordingly, according to the electroplating solution analyzing system 1 and the electroplating solution analyzing method used by such system, unlike the conventional analysis method where a deposition process is carried out on samples for analysis purposes using the electroplating solution to be analyzed and the state of the electroplating solution is analyzed by measuring the deposited state of the metal on such samples, it is possible to easily analyze the state of changes in the electroplating solution Xa based on reference values that are values showing the state of the electroplating solution Xa before the changes and measurement values that are values showing the state of changes in the electroplating solution Xa, and when doing so, it is possible, by dissolving the metal that was deposited on the working electrode 12 (12a) during the "process 1B" into the electroplating solution Xa during the "process 2B", to produce a state where no metal is deposited on the working electrode 12 (12a) at the start of the next "deposition-dissolution process". This means that it is possible to immediately start the next "deposition-dissolution process" and analyze the state of changes in the electroplating solution Xa without replacing the working electrode 12 (12a) numerous times or removing the metal deposited on the working electrode 12 (12a). By doing so, compared to the conventional analysis method where it is necessary to discard samples every time the state of changes in the electroplating solution Xa is analyzed, it is possible to analyze the state of changes in the electroplating solution Xa easily and at low cost.

Also, according to the electroplating solution analyzing system 1 and the electroplating solution analyzing method used by such system, at least one of:

the "process Ab" that calculates the "second charge" applied to the electroplating solution Xa during the "process 2B" based on the current value of the "second current" and the "second period" and concludes from analysis that the electroplating solution Xa has changed to a state where the amount of metal deposited per unit time is larger than the "reference state A" when the "second charge" is larger than the reference value A and concludes from analysis that the electroplating solution Xa has changed to a state where the amount of metal deposited per unit time is smaller than the "reference state A" when the "second charge" is smaller than the reference value A;

the "process Bb" that calculates the "first charge" applied to the electroplating solution Xa during the "process 1B" based on the current value of the "first current" and the "first period", calculates the "second charge" based on the current value of the "second current" and the "second period", concludes from analysis that the electroplating solution Xa has changed to a state where the charge that does not contribute to the deposition of metal during a plating process is less than the "reference state B" when the difference between the "first charge" and the "second charge" is smaller than the "reference value B", and concludes from analysis that the electroplating solution Xa has changed to a state where the charge that does not contribute to the deposition of metal during the plating process is more than the "reference state B" when the difference between the "first charge" and the "second charge" is larger than the "reference value B";

the "process Cb" that concludes from analysis that the amount of impurities included in the electroplating solution Xa has changed to a state that is larger than the "reference state C" when the current value of the "second current" is larger than the reference value C and concludes from analysis that the amount of impurities included in the electroplating solution Xa has changed to a state that is smaller than the "reference state C" when the current value of the "second current" is smaller than the reference value C; and the "process Db" that calculates the "first charge" based on the current value of the "first current" and the "first period", calculates the "third charge" that contributes to dissolution of metal out of the "second charge" based on the current value of the "second current" and the state of changes in the current value during the "second period", concludes from analysis when the ratio of the "third charge" to the "first charge" is larger than the "reference value D" that the electroplating solution Xa has changed to a state where the charge that contributes to the deposition of metal during the plating process is larger than the "reference state D" where the "reference value D" is capable of being acquired by the "measurement value acquiring process", and concludes from analysis when the ratio of the "third charge" to the "first charge" is smaller than the "reference value D" that the electroplating solution Xa has changed to a state where the charge that contributes to the deposition of metal during the plating process is smaller than the "reference state D", is executed as the "analysis process".

Accordingly, according to the electroplating solution analyzing system 1 and the electroplating solution analyzing method used by such system, unlike the conventional analysis method that executes an analysis process on samples for analysis purposes and measures the deposited state of metal, by executing a process (any of the processes Ab to Db) in keeping with the desired factors to be analyzed, it is possible, even for a user who is unused to analysis of the electroplating solution Xa, to easily and accurately analyze the state of changes in the electroplating solution Xa.

In addition, according to the electroplating solution analyzing system 1 and the electroplating solution analyzing method used by such system, the process "Eb" in which the "measurement value acquiring process 1b" that uses the working electrode 12 whose electrode surface is formed by a "first material (in the present embodiment, platinum)" with at least a preset level of insolubility in the electroplating solution Xa as the "working electrode", and the "measurement value acquiring process 2b" that uses, as the "working electrode", the working electrode 12a whose electrode surface is formed by a "second material (in the present embodiment, copper)" that is the same as the plated object onto which metal is to be deposited by the plating process and whose electrode surface has the same area as the electrode surface of the working electrode 12 and sets the "first period" and voltage value of the "first voltage" during the "process 1B" and "the second period" and the voltage value and rate of change of the "second voltage" during the "second period" as the same as during the "measurement value acquiring process 1b", are respectively executed as the "measurement value acquiring process", and as the "analysis process", calculates the "fourth charge" applied to the electroplating solution Xa during the "process 2B" in the "measurement value acquiring process 1b" based on the current value of the "second current" and the "second period" for which the "second current" flowed in the "measurement value acquiring process 1b", calculates the "fifth charge" that contributes to dissolution of metal during the "process 2B" in the "measurement value acquiring process 2b" based on the current value of the "second current" in the "measurement value acquiring process 2b" and the state of the changes in the current value during the "second period", calculates the "sixth charge" that is the difference between the "fourth charge" and the "fifth charge", concludes, when the "sixth charge" is smaller than the "reference value E", that the electroplating solution Xa has changed to a state where the rate of dissolution per unit time of the plated object is lower than the "reference state E" that is capable of calculating a "sixth charge" that is equal to the "reference value E" based on the measurement values acquired by the "measurement value acquiring process 1b" and the "measurement value acquiring process 2b", and concludes, when the "sixth charge" is larger than the "reference value E", that the electroplating solution Xa has changed to a state where the rate of dissolution per unit time of the plated object is higher than the "reference state E".

Accordingly, according to the electroplating solution analyzing system 1 and the electroplating solution analyzing method used by such system, it is possible to easily and accurately analyze the extent to which the electroplating solution Xa to be analyzed has changed to a state that dissolves the plated object due to an oxidation reaction during the plating process.

Note that the configuration of an "electroplating solution analyzing apparatus" is not limited to the example configuration of the electroplating solution analyzing system 1 described above. As one example, a configuration that executes three-electrode measurement using all three of the reference electrode 11, the working electrode 12 and the counter electrode 13 or all three of the reference electrode 11, the working electrode 12*a*, and the counter electrode 13 during the "deposition-dissolution process" in the "measurement value acquiring process" has been described above as an example, instead of such configuration, it is possible to use a configuration that executes two-electrode measurement using both of the reference electrode 11 and the working electrode 12 or both of the reference electrode 11 and the working electrode 12*a* during the "deposition-dissolution process" in the "measurement value acquiring process". Note that when such configuration is used, since the only difference is that the currents (other examples of the "first current" and the "second current") flowing between the working electrode 12 (12*a*) and the reference electrode 11 are measured in place of measuring the currents (the "first current" and the "second current") flowing between the counter electrode 13 and the working electrode 12 (12*a*) in the "deposition-dissolution process", drawings and description relating to such configuration are omitted.

Also, although an example configuration where a plurality of sets of measurement value data D0 and D0*a* are acquired by a plurality of iterations of the "deposition-dissolution process" in order to set the processing conditions during an electroplating process that uses the electroplating solution Xa when new electroplating solution Xa is introduced in the plating solution tank X, and the reference value data DC and DCa as the "reference values" for subsequently analyzing the state of changes in the electroplating solution Xa are acquired out of a plurality of sets of measurement value data D0 and D0*a* has been described, in place of such configuration, as examples it is also possible to use values (values given in documentation such as a catalog) indicated by the manufacturer of the electroplating solution Xa or values arbitrarily decided by the user as the "reference values".

In addition, during the "process 1B" in the "measurement value acquiring process" for analyzing the state of changes in the electroplating solution Xa, it is also possible to apply a "first voltage" that produces a different current density to the actual electroplating process that uses the electroplating solution Xa between both electrodes 11 and 12 (12*a*). Also, although an example where, in the "measurement value acquiring process 1*b*" as the "measurement value acquiring process" for analyzing the state of changes in the electroplating solution Xa, the measurement value data D0 is acquired by a single execution of the "deposition-dissolution process" where the voltage value of the "first voltage" applied between both electrodes 11 and 12 is set at −1.6V, in the "measurement value acquiring process 2*b*" as the "measurement value acquiring process" for analyzing the state of changes in the electroplating solution Xa, the measurement value data D0*a* is acquired by a single execution of the "deposition-dissolution process" where the voltage value of the "first voltage" applied between both electrodes 11 and 12*a* is set at −1.6V, and the processing in the "processes Ab to Gb" is executed based on the acquired measurement value data D0 and D0*a* and the corresponding reference value data DC and DCa, it is also possible to use a configuration that separately acquires a plurality of sets of measurement value data D0 and D0*a* with different voltage values of the "first voltage" during the "process 1B" as the measurement values for executing the processing in the "processes Ab to Gb".

Also, although an example has been described where the voltage (the second voltage: the potential of the working electrode 12 (12*a*) relative to the reference electrode 11) applied between both electrodes 11 and 12 (12*a*) is changed so as to increase from −0.5V to 1.0V during the "process 2A" and the "process 2B" of each "deposition-dissolution process", in place of such configuration, it is also possible to use a configuration that changes so as to decrease from 1.0V to −0.5V. When such configuration is used, by setting a voltage value range so that the potential of the working electrode 12 (12*a*) relative to the reference electrode 11 is a potential such that metal is not deposited on the working electrode 12 (12*a*), a state where metal is not deposited on the working electrode 12 (12*a*) will be produced at the end of each "deposition-dissolution process". For this reason, in the same way as the example configuration described above, it is possible to execute a plurality of iterations of the "deposition-dissolution process" continuously, and in the same way as the example configuration described above, it is possible to immediately start the next "deposition-dissolution process" and analyze the state of the electroplating solution Xa without replacing the working electrode 12 (12*a*) numerous times or removing metal deposited on the working electrode 12 (12*a*).

In addition, although an example has been described where the working electrode 12 whose electrode surface is formed of platinum is used as the "first electrode where at least the electrode surface is formed of a first material that has at least a preset level of insolubility in the electroplating solution, the "first material" that forms the electrode surface of the "first electrode" is not limited to platinum and it is possible to use various materials, such as iridium, ruthenium, and titanium, that are highly insoluble in the electroplating solution.

Also, although an example has been described where various analysis is carried out using only the measurement value data D0 acquired by the "measurement value acquiring processes 1*a* and 1*b*" during processing aside from the "processes Ga and Eb" in the "analysis process", it is also possible to carry out various analysis using only the measurement value data D0*a* acquired in the "measurement value acquiring processes 2*a* and 2*b*" during processing aside from the "processes Ga and Eb". Here, since the electrode surface of the working electrode 12*a* dissolves due to an oxidation reaction during the "processes 1A and 1B" and the "processes 2A and 2B" in the "measurement value acquiring processes 2*a* and 2*b*", it is necessary to calculate the "charge that contributes to the deposition of metal" in view of the charge that contributes to the dissolution of the electrode surface.

In addition, although a configuration where all of the "processes Aa to Ga" are executed during the "analysis process" was described as the "first embodiment", it is also possible to use a configuration that does not execute one or more of the "processes Aa to Ga" when such processes are not necessary. In the same way, although a configuration where all of the "processes Ab to Eb" and the process "Fb" and the process Gb" are executed during the "analysis process" was described as the "second embodiment", it is also possible to use a configuration that does not execute one or more of the "processes Ab to Gb" when such processes are not necessary.

Also, as one example, it is possible to execute an analysis process that specifies, in addition to any of the processes "processes Aa to Ga" described above, the relationship between the current density and parameters such as the "volume", "density", and "thickness" of the metal in each "deposition-dissolution process" for the amount of metal deposited on the working electrode 12 (12*a*). Note that since the relationship between the "amount of metal" and the "volume", "density", and "thickness" of the metal specified in each of the processes described above is known, detailed description thereof is omitted.

In addition, although the electroplating solution analyzing system 1 has been described by way of an example configured with the electrochemical measuring apparatus 2, which executes part of the "measurement value acquiring process" (i.e., generation of the measurement value data D0 and D0a), and the analyzing apparatus 3, which executes the other part of the "measurement value acquiring process" (i.e., reception of the measurement value data D0 and D0a from the electrochemical measuring apparatus 2) and the "analysis process", are separately constructed, it is possible to use an "electroplating solution analyzing apparatus" (not illustrated) where the electrochemical measuring apparatus 2 and the analyzing apparatus 3 of the electroplating solution analyzing system 1 are integrated to analyze the electroplating solution Xa.

What is claimed is:

1. An electroplating solution analyzing apparatus comprising:
    a measurer configured to execute a measurement process that measures a current value of a current flowing between a counter electrode and a working electrode that have been placed in contact with an electroplating solution to be analyzed while applying a voltage to a reference electrode and the working electrode that have been placed in contact with an electroplating solution; and
    a processor configured to execute a measurement value acquiring process which controls the measurer to execute the measurement process and acquires measurement values and an analysis process that analyzes a state of the electroplating solution based on the acquired measurement values, the acquired measurement values including a first set of measurement values and a second set of measurement values,
    wherein the processor executes, as the measurement value acquiring process,
    a deposition-dissolution process configured to execute:
    a process 1A that measures a current value of a first current that flows between the counter electrode and the working electrode as the first set of measurement values while depositing metal on the working electrode by applying a first voltage with a voltage value set in advance between the reference electrode and the working electrode for a first period set in advance; and
    a process 2A that measures with a cycle set in advance, as the second set of measurement values, a current value of a second current that flows between the counter electrode and the working electrode while dissolving the metal that was deposited on the working electrode in the process 1A into the electroplating solution by applying a second voltage whose voltage value changes with a rate of change set in advance between the reference electrode and the working electrode for a second period set in advance,
    repeating process 1A and process 2A in that order a plurality of times while changing the voltage value of the first voltage in a voltage value range set so as to produce a current density within a current density range set in advance,
    and the processor analyzes, in the analysis process, the state of the electroplating solution based on the first set of measurement values and the second set of measurement values acquired by the measurement value acquiring process.

2. The electroplating solution analyzing apparatus according to claim 1,
    wherein, in the analysis process, the processor executes at least one of:
    a process Aa that calculates, for each deposition-dissolution process, a second electrical charge applied to the electroplating solution during the process 2A based on the current value of the second current and a second period for which the second current flowed between the counter electrode and the working electrode in the process 2A,
    calculates, for each deposition-dissolution process, a first current density based on the electrode area of the working electrode and the current value of the first current, and
        concludes from analysis, based on the calculated second charge and first current density, that the electroplating solution is in a state where the amount of metal deposited on a plated object per unit time increases as a plating process is carried out under conditions that produce the first current density in a deposition-dissolution process for which the second charge is large and where the amount of metal deposited on the plated object per unit time decreases as the plating process is carried out under conditions that produce the first current density in a deposition-dissolution process for which the second charge is small;
    a process Ba that calculates, for each deposition-dissolution process, a first electrical charge applied to the electroplating solution during the process 1A based on the current value of the first current and the first period,
    calculates, for each deposition-dissolution process, the second charge based on the current value of the second current and the second period,
    calculates a difference between the first charge and the second charge for each deposition-dissolution process,
    calculates the first current density for each deposition-dissolution process based on an electrode area of the working electrode and the current value of the first current, and
    concludes from analysis, based on the calculated first charge, second charge, and first current density, that the electroplating solution is in a state where charge that does not contribute to deposition of metal on the plated object decreases as a plating process is carried out under conditions that produce the first current density in a deposition-dissolution process where the difference in charge is small and where the charge that does not contribute to the deposition of metal on the plated object increases as the plating process is carried out under conditions that produce the first current density in a deposition-dissolution process where the difference in charge is large;
    a process Ca that calculates, for each deposition-dissolution process, the second charge based on the current value of the second current and the second period,
    calculates, for each deposition-dissolution process, the amount of metal deposited on the working electrode during the process 1A based on the second charge,
    calculates, for each deposition-dissolution process, the first current density based on the electrode area of the working electrode and the current value of the first current,
    specifies, based on the calculated amount of metal and first current density, a current density lower limit value for the first current density capable of depositing at least an amount of metal set in advance on the working electrode, and concludes from analysis that the electroplating solution is in a state where it is not possible to deposit at least the amount of metal set in advance on the plated object when a plating process is carried out under conditions that produce a first current density that falls below the current density lower limit value;

a process Da that calculates, for each deposition-dissolution process, the second charge based on the current value of the second current and the second period, calculates, for each deposition-dissolution process, the amount of metal deposited on the working electrode during the process 1A based on the second charge, calculates, for each deposition-dissolution process, the first current density based on the electrode area of the working electrode and the current value of the first current, specifies, based on the calculated amount of metal and first current density, a current density upper limit value for the first current density capable of depositing at least an amount of metal set in advance on the working electrode, and concludes from analysis that the electroplating solution is in a state where it is not possible to deposit at least the amount of metal set in advance on the plated object when a plating process is carried out under conditions that produce a first current density that exceeds the current density upper limit value;

a process Ea that concludes from analysis, based on the current value of the second current in each deposition-dissolution process, that impurities are included in the electroplating solution when the current value of the second current is at least a reference current value set in advance; and a process Fa that calculates, for each deposition-dissolution process, the first charge based on the current value of the first current and the first period, calculates, for each deposition-dissolution process, a third charge that does not contribute to dissolution of the metal out of the second charge, based on the current value of the second current and a state of changes in the current value of the second current in the second period, calculates, for each deposition-dissolution process, the first current density based on the electrode area of the working electrode and the current value of the first current, and concludes from analysis, based on the first current density, the first charge, and the third charge, that the electroplating solution is in a state where charge that contributes to the deposition of metal on the plated object increases as a plating process is carried out under conditions that produce the first current density during a deposition-dissolution process for which the ratio of the third charge to the first charge is large and where the charge that contributes to the deposition of metal on the plated object decreases as the plating process is carried out under conditions that produce the first current density during a deposition-dissolution process for which the ratio of the third charge to the first charge is small.

3. The electroplating solution analyzing apparatus according to claim 1,
wherein, in the measurement value acquiring process, the processor executes:

a measurement value acquiring process 1a that uses, as the working electrode, a first electrode with at least an electrode surface formed of a first material with at least a preset level of insolubility in the electroplating solution; and a measurement value acquiring process 2a that uses, as the working electrode, a second electrode with at least an electrode surface formed by a second material that is the same as a plated object on which metal is to be deposited by the plating process and is configured such that an area of the electrode surface is the same as an area of the electrode surface of the first electrode, and sets the first period and the voltage value of the first voltage in the process 1A, and the second period, the voltage value and rate of change of the voltage value of the second voltage in the process 2A equal to the measurement value acquiring process 1a, and executes, as the analysis process, a process Ga that calculates, for each deposition-dissolution process, a fourth electrical charge applied to the electroplating solution during the process 2A in the measurement value acquiring process 1a based on the current value of the second current and the second period for which the second current flowed in the measurement value acquiring process 1a, calculates, for each deposition-dissolution process, a fifth electrical charge that contributes to dissolution of the metal during the process 2A in the measurement value acquiring process 2a based on the current value of the second current and a state of changes in the current value in the second period during the measurement value acquiring process 2a, calculates a sixth electrical charge that is a difference between the fourth electrical charge and the fifth electrical charge for each deposition-dissolution process for which the voltage value of the first voltage applied during the process 1A is equal, calculates, for each deposition-dissolution process, the first current density based on the current value of the first current and the electrode area of a predetermined electrode out of the first electrode and the second electrode, and concludes from analysis, based on the calculated first current density and sixth electrical charge, that the electroplating solution is in a state where a rate of dissolution per unit time of the plated object decreases as the plating process is carried out under conditions that produce a first current density for which the sixth electrical charge is small and where the rate of dissolution per unit time of the plated object increases as the plating process is carried out under conditions that produce a first current density for which the sixth electrical charge is large.

4. The electroplating solution analyzing apparatus according to claim 2,
wherein, in the measurement value acquiring process, the processor executes:

a measurement value acquiring process 1a that uses, as the working electrode, a first electrode with at least an electrode surface formed of a first material with at least a preset level of insolubility in the electroplating solution; and a measurement value acquiring process 2a that uses, as the working electrode, a second electrode with at least an electrode surface formed by a second material that is the same as a plated object on which metal is to be deposited by the plating process, the second electrode configured such that an area of the electrode surface is the same as an area of the electrode surface of the first electrode, sets the first period and the voltage value of the first voltage in the process 1A, and the second period, the voltage value and rate of change of the voltage value of the second voltage in the process 2A equal to the measurement value acquiring process 1a, and executes, as the analysis process, a process Ga that calculates, for each deposition-dissolution process, a fourth charge applied to the electroplating solution during the process 2A in the measurement value acquiring process 1a based on the current value of the second current and the second period for which the second current flowed in the measurement value acquiring process 1a, calculates, for each deposition-dissolution process, a fifth charge that contributes to dissolution of the metal during the process 2A in the measurement value acquiring process 2a based on the current value of the second current and a state of changes in the current value in the second period during the measurement value acquiring process 2a, calculates a sixth charge that is a difference between the fourth charge and the fifth charge for each deposition-dissolution process for which the voltage value of the first voltage applied during the process 1A is equal, calculates, for each deposition-dissolution process, the first current density based on the current value of the first current and the electrode area of a predetermined electrode out of the first electrode and the second electrode, and concludes from analysis, based on the calculated first current density and sixth charge, that the electroplating solution is in a state where a rate of dissolution per unit time of the plated object decreases as the plating process is carried out under conditions that produce a first current density for which the sixth charge is small and where the rate of dissolution per unit time of the plated object increases as the plating process is carried out under conditions that produce a first current density for which the sixth charge is large.

5. An electroplating solution analyzing apparatus comprising:

a measurer configured to execute a measurement process that measures a current value of a current flowing between a counter electrode and a working electrode that have been placed in contact with an electroplating solution to be analyzed while applying a voltage to a reference electrode and the working electrode that have been placed in contact with an electroplating solution; and a processor configured to execute a measurement value acquiring process which controls the measurer to execute the measurement process and acquires measurement values and an analysis process that analyzes a state of the electroplating solution based on the acquired measurement values, the acquired measurement values including a first set of measurement values and a second set of measurement values, wherein the processor executes, as the measurement value acquiring process, a process 1B that measures a current value of a first current that flows between the counter electrode and the working electrode as the first set of measurement values while depositing metal on the working electrode by applying a first voltage with a voltage value set in advance between the reference electrode and the working electrode for a first period set in advance; and a process 2B that measures with a cycle set in advance, as the second set of measurement values, a current value of a second current that flows between the counter electrode and the working electrode while dissolving the metal that was deposited on the working electrode in the process 1B into the electroplating solution by applying a second voltage whose voltage value changes with a rate of change set in advance between the reference electrode and the working electrode for a second period set in advance, repeating process 1B and process 2B in that order, and analyzes, in the analysis process, the state of the electroplating solution based on the first set of measurement values and the second set of measurement values acquired by the measurement value acquiring process and reference values set in advance.

6. The electroplating solution analyzing apparatus according to claim 5, wherein, in the analysis process, the processor executes at least one of:

a process Ab that calculates a second electrical charge applied to the electroplating solution during the process 2B based on the current value of the second current and a second period for which the second current flowed between the counter electrode and the working electrode during the process 2B, and concludes from analysis, when the second electrical charge is larger than a reference value A as the reference values, that the electroplating solution has changed to a state where the amount of metal deposited per unit time in a plating process is larger than a reference state A for which the measurement value acquiring process is capable of acquiring the reference value A, and when the second electrical charge is smaller than the reference value A, that the electroplating solution has changed to a state where the amount of metal deposited per unit time in the plating process is less than the reference state A;

a process Bb that calculates a first electrical charge applied to the electroplating solution during the process 1B based on the current value of the first current and the first period, calculates the second electrical charge based on the current value of the second current and the second period, and concludes from analysis, when a difference between the first electrical charge and the second electrical charge is smaller than a reference value B as the reference values, that the electroplating solution has changed to a state where electrical charge that does not contribute to deposition of metal during the plating process is smaller than a reference state B for which the measurement value acquiring process is capable of acquiring the reference value B, and when the difference between the first electrical charge and the second electrical charge is larger than the reference value B, that the electroplating solution has changed to a state where electrical charge that does not contribute to deposition of metal during the plating process is larger than a reference state B;

a process Cb that concludes from analysis, when the current value of the second current is larger than a reference value C as the reference values, that an amount of impurities included in the electroplating solution has changed to a larger amount than a reference state C for which the measurement value acquiring process is capable of acquiring the reference value C, and when the current value of the second current is smaller than the reference value C, that the amount of impurities included in the electroplating solution has changed to a smaller amount than the reference state C; and a process Db that calculates the first electrical charge based on the current value of the first current and the first period, calculates a third electrical charge that contributes to dissolution of the metal out of the second electrical charge based on the current value of the second current and a state of changes in the current value of the second current during the second period, concludes from analysis, when the ratio of the third electrical charge to the first electrical charge is larger than a reference value D as the reference values, that the electroplating solution has changed to a state where electrical charge that contributes to deposition of metal during the plating process is larger than a reference state D where the measurement value acquiring process is capable of acquiring the reference value D, and when the ratio of the third electrical charge to the first electrical charge is smaller than the reference value D, that the electroplating solution has changed to a state where electrical charge that contributes to deposition of metal during the plating process is smaller than the reference state D.

7. The electroplating solution analyzing apparatus according to claim 6, wherein, in the measurement value acquiring process, the processor executes:

a measurement value acquiring process 1b that uses, as the working electrode, a first electrode with at least an electrode surface formed of a first material with at least a preset level of insolubility in the electroplating solution; and a measurement value acquiring process 2b that
uses, as the working electrode, a second electrode with at least an electrode surface formed by a second material that is the same as a plated object on which metal is to be deposited by the plating process, the second electrode configured such that an area of the electrode surface is the same as an area of the electrode surface of the first electrode, sets the first period and the voltage value of the first voltage in the process 1B, and the second period, the voltage value and rate of change of the voltage value of the second voltage in the process 2B equal to the measurement value acquiring process 1b, and executes, as the analysis process,
a process Eb that calculates a fourth charge applied to the electroplating solution during the process 2B in the measurement value acquiring process 1b based on the current value of the second current and the second period for which the second current flowed in the measurement value acquiring process 1b, calculates a fifth charge that contributes to dissolution of the metal during the process 2B in the measurement value acquiring process 2b based on the current value of the second current and a state of changes in the current value during the second period in the measurement value acquiring process 2b, calculates a sixth charge that is a difference between the fourth charge and the fifth charge, and concludes from analysis, when the sixth charge is smaller than a reference value E as the reference values, that the electroplating solution has changed to a state where a rate of dissolution per unit time of the plated object is lower than a reference state E capable of calculating the sixth charge that is equal to the reference value E based on the measurement values acquired by the measurement value acquiring process 1b and the measurement value acquiring process 2b, and when the sixth charge is larger than the reference value E, that the electroplating solution has changed to a state where a rate of dissolution per unit time of the plated object is higher than the reference state E.

8. The electroplating solution analyzing apparatus according to claim 5, wherein, in the measurement value acquiring process, the processor executes:

a measurement value acquiring process 1b that uses, as the working electrode, a first electrode with at least an electrode surface formed of a first material with at least a preset level of insolubility in the electroplating solution; and a measurement value acquiring process 2b that uses, as the working electrode, a second electrode with at least an electrode surface formed by a second material that is the same as a plated object on which metal is to be deposited by the plating process and is configured such that an area of the electrode surface is the same as an area of the electrode surface of the first electrode, and sets the first period and the voltage value of the first voltage in the process 1B, and the second period, the voltage value and rate of change of the voltage value of the second voltage in the process 2B equal to the measurement value acquiring process 1b, and executes, as the analysis process,
a process Eb that calculates a fourth electrical charge applied to the electroplating solution during the process 2B in the measurement value acquiring process 1b based on the current value of the second current and the second period for which the second current flowed in the measurement value acquiring process 1b, calculates a fifth electrical charge that contributes to dissolution of the metal during the process 2B in the measurement value acquiring process 2b based on the current value of the second current and a state of changes in the current value during the second period in the measurement value acquiring process 2b, calculates a sixth electrical charge that is a difference between the fourth electrical charge and the fifth electrical charge, and concludes from analysis, when the sixth electrical charge is smaller than a reference value E as the reference values, that the electroplating solution has changed to a state where a rate of dissolution per unit time of the plated object is lower than a reference state E capable of calculating the sixth electrical charge that is equal to the reference value E based on the measurement values acquired by the measurement value acquiring process 1b and the measurement value acquiring process 2b, and when the sixth electrical charge is larger than the reference value E, that the electroplating solution has changed to a state where a rate of dissolution per unit time of the plated object is higher than the reference state E.

* * * * *